US011608371B1

(12) United States Patent
Li et al.

(10) Patent No.: US 11,608,371 B1
(45) Date of Patent: Mar. 21, 2023

(54) THERAPEUTIC MOLECULES

(71) Applicant: PetMedix Ltd, Cambridge (GB)

(72) Inventors: Meng Amy Li, Cambridge (GB); Marco Bardelli, Cambridge (GB)

(73) Assignee: PETMEDIX LTD, Cambridge (GB)

( * ) Notice: Subject to any disclaimer, the term of this patent is extended or adjusted under 35 U.S.C. 154(b) by 0 days.

(21) Appl. No.: 17/506,876

(22) Filed: Oct. 21, 2021

(51) Int. Cl.

| | |
|---|---|
| *A61P 25/04* | (2006.01) |
| *C07K 14/705* | (2006.01) |
| *A61K 47/65* | (2017.01) |
| *A61K 38/00* | (2006.01) |

(52) U.S. Cl.
CPC ........ *C07K 14/70578* (2013.01); *A61K 47/65* (2017.08); *A61P 25/04* (2018.01); *A61K 38/00* (2013.01); *C07K 2319/00* (2013.01)

(58) Field of Classification Search
CPC ............ C07K 2317/52; C07K 2319/30; C07K 16/2863; C07K 14/70578; C07K 16/18; C07K 14/48; C07K 2319/00; C07K 14/71; C07K 16/22; C07K 14/475; C07K 16/46; A61K 38/00; A61K 38/177; A61K 38/18; A61K 38/1709; A61K 39/3955; A61K 47/6803; A61K 38/185; A61P 25/00; A61P 25/28; A61P 25/04; G01N 2800/28; G01N 2800/2842; G01N 2333/575; G01N 2333/71
See application file for complete search history.

(56) References Cited

U.S. PATENT DOCUMENTS

2016/0222082 A1 * 8/2016 Westbrook ....... C07K 14/70578

FOREIGN PATENT DOCUMENTS

| | | | |
|---|---|---|---|
| EP | 3046934 | B1 | 12/2018 |
| GB | 2542445 | A | 3/2017 |
| WO | 2013/136078 | A1 | 9/2013 |
| WO | 2016/009222 | A1 | 1/2016 |
| WO | 2016/146841 | A1 | 9/2016 |
| WO | WO2020142625 | A2 * | 7/2020 |
| WO | 2020/191289 | A1 | 9/2020 |

OTHER PUBLICATIONS

Zhu Feng, et al., Prokaryotic expression of recombinant human p75NTR-Fc fusion protein and its effect on the neurite outgrowth of dorsal root ganglia neuron, Journal of Medical Colleges of PLA 24 (2009) 1-9.

Christelle Langevin, et al. Mutations Conferring Resistance to Neutralization by a Soluble Form of the Neurotrophin Receptor (p75NTR) Map outside of the Known Antigenic Sites of the Rabies Virus Glycoprotein, Journal of Virology (Nov. 2002) vol. 76, No. 21, p. 10756-10765.

Search Report dated Apr. 20, 2022 , issued tn copending Application No. GB 2115098.2.

* cited by examiner

*Primary Examiner* — Aradhana Sasan
*Assistant Examiner* — Jia-Hai Lee
(74) *Attorney, Agent, or Firm* — Duane Morris LLP; Thomas J. Kowalski; Deborah L. Lu

(57) ABSTRACT

The present invention relates to effective pain therapies in companion animals. In particular, an isolated companion animal p75NTR protein or a fusion protein containing the same or portions thereof are contemplated. Nucleic acids encoding the proteins are also encompassed in the invention as well as methods of using the same.

12 Claims, 31 Drawing Sheets

Specification includes a Sequence Listing.

```
Horse    KEVQPTDLYTHSGECCKAQNLGEGVAQPCGANQTVCEPCLDSVTFSDWSATEPCKPCTE    60
Bovine   KEACLTGLYTHSGECCKAQNLGEGVAQPCGANQTVCEPCLDSVTFSDWSATEPCKPCTE    60
Dog      KEACPTGLYTHSGECCKAQNLGEGVAQPCGANQTVCEPCLDSVTFSDWSATEPCKPCTE    60
Cat      KEACPTGLFTHSGECCKAQNLGEGVAQPCGANQTVCEPCLDSVTFSDWSATEPCKPCTE    60
         **:*.*.*:*************************************************

Horse    CVGLQSMSAPCVEADDAVCRCAYGYYQDETTGRCEACQVCEAGSGLVFSCQDKQNTVCEE   120
Bovine   CVGLQSMSAPCVEADDAVCRCAYGYYQDETTGRCEACRVCEAGSGLVFSCQDKQNTVCEE   120
Dog      CVGLQSMSAPCVEADDAVCRCAYGYYQDETTGRCEACRVCEAGSGLVFSCQDRQNTVCEE   120
Cat      CVGLQSMSAPCVEADDAVCRCAYGYYQDETTGRCEACRVCEAGSGLVFSCQDRQNTVCEE   120
         *********************************:***********************

Horse    CPDGTYSDEANHVDPCLPCTVCEDTERQLRECTRWADAECEEIP                  164
Bovine   CPDGTYSDEANHVDPCLPCTVCEDTERQLRECTRWADAECEEIP                  164
Dog      CPDGTYSDEANHVDPCLPCTVCEDTERQLRECTRWADAECEEIP                  164
Cat      CPDGTYSDEANHVDPCLPCTVCEDTERQLRECTRWADAECEEIP                  164
         ********************************************
```

FIG.2A

```
CAT_IGG1V1   ------TDHPPGPKPCDC--PKCPPPEMLGGPSIFIFPPKPKDTLSISRTPEVTCLVVDLG   53
CAT_IGG1V2   ------TDHPPGPKPCDC--PKCPPPEMLGGPSIFIFPPKPKDTLSISRTPEVTCLVVDLG   53
CAT_IGG2     ------KTASTIESKTGEG-PKCPVPEIPGAPSVFIFPPKPKDTLSISRTPEVTCICLVVDLG   54
DOGA         -----FN--EQRCTD-TPPCPVPEPLGGPSVLIFPPKPKDILRITRTPEVTCVVVDLG       50
DOGD         --------ESTCKC--ISPCPVPESLGGPSVFIFPPKPKDILRITRTPEVTCVVVDLG       48
DOGC         -----ECECKCNCNNCPCPGCGLLGGPSVFIFPPKPKDILVTARTPTVTCVVVDLD         51
DOGB         RENGRVPRPPDCPK---CPAPEMLGGPSVFIFPPKPKDTLLIARTPEVTCVVVDLD         53
DOGB-YTE     RENGRVPRPPDCPK---CPAPEMLGGPSVFIFPPKPKDTLYITREPEVTCVVVDLD         53
```

FIG.2B

| | | |
|---|---|---|
| HORSE_IGHG2 | CVLSAEGVIPIPSVPKPQCPPYTHSKFLGGPSVFIFPPNPKDALMISRTPVTCVVNLS | 60 |
| HORSE_IGHG6 | ----------K----EPCCOPKCP--------------GRPSVFIFPPNPKDTLMISRTPEVTCVVDVS | 42 |
| HORSE_IGHG3 | ------------TTPP----CPCECPKCPAPELLGGPSVFIFPPKPKDVLMITRTPEVTCLVVDVS | 50 |
| HORSE_IGHG5 | ------------VV----KGSPOPKCPAPELPGGPSVFIFPPKPKDVLKISRKPEVTCVVVDLG | 48 |
| HORSE_IGHG1 | ----------VIKE----CNGGCP--AE-CLQVGPSVFIFPPKPKDVLMISRTPVTCVVVDVG | 47 |
| HORSE_IGHG4 | ----------VIKE----CNGGCP--AE-CLQVGPSVFIFPPKPKDVLMISRTPVTCVVVDVG | 47 |
| HORSE_IGHG7 | ----------VIKE----CG GCPTCPE-CLSVGPSVFIFPPKPKDVLMISRTPVTCVVVDVG | 48 |
| | *:  :**:* * *** *:; : | |
| CAT_IGG1V1 | PDDSDVQITMFVDNTQVYTAKTSPREEQFNSTYRVVSVLPILHQDWLKGKEFKCKVNSKS | 113 |
| CAT_IGG1V2 | PDDSDVQITMFVDNTQVYTAKTSPREEQFNSTYRVVSVLPILHQDWLKGKEFKCKVNSKS | 113 |
| CAT_IGG2 | PDDSNVQITMFVDNTEMHTAKTRPREEQFNSTYRVVSVLPILHQDWLKGKEFKCKVNSKS | 114 |
| DOGA | REDPEVQISWFVDGKEVHTAKTQSREQFNGTYRVVSVLPIEHQDWLTGKEFKCRVNHID | 110 |
| DOGD | REDPEVQISWFVDGKEVHTAKTQPREQFNGTYRVVSVLPIEHQDWLTGKEFKCRVNHIG | 108 |
| DOGC | PENPEVQISWFVDGKQVQTANTQPREEQSNGTYRVVSVLPIGHQDWLSGKQFKCKVNHKA | 111 |
| DOGB | PEDPEVQISWFVDGKQMQTAKTQPREEQFNGTYRVVSVLPIGHQDWLKGKQFTCKVNNKA | 113 |
| DOGB-YTE | PEDPEVQISWFVDGKQMQTAKTQPREEQFNGTYRVVSVLPIGHQDWLKGKQFTCKVNNKA | 113 |
| HORSE_IGHG2 | DQYPDVQFSWYVDNTEVHSAITKQREAQFNSTYRVVSVLPIQHQDWMRGKEFKCSVTNVG | 120 |
| HORSE_IGHG6 | QENPDVKFNMYVDGVEAHTATTKAKEKQDNSTYRVVSVLRIQHQDWLNGKEFKCKVNRA | 102 |
| HORSE_IGHG3 | HDSSDVLFTWYVDGTEVKTAKTMPNEEQNNSTYRVVSVLRIQHQDWLNGKEFKCSVTNKA | 110 |
| HORSE_IGHG5 | HDDPDVQFTWFVDGVETHTATTEPKEEQFNSTYRVVSVLPIQHKDWLSGKEFKCSVTNKA | 108 |
| HORSE_IGHG1 | HDFPDVQFNMYVDGVETHTATTEPKQENNSTYRVVSVLPIQHKDWLSGKEFKCKVNNKA | 107 |
| HORSE_IGHG4 | HDFPDVQFNMYVDGVETHTATTEPKQEVNSTYRVVSVLPIQHKDWLSGKEFKCKVNNKA | 107 |
| HORSE_IGHG7 | HDFPDVQFNMYVDGVETHTATTEPKQEQNNSTYRVVSILAIQHKDWLSGKEFKCKVNNQA | 108 |
| | : :  *  :  * ; *  :* .* .****** *  :* ***.*  ** | |

FIG. 2B Cont'd

| | | |
|---|---|---|
| CAT_IGG1V1 | LPSPIERTISKAKGQPHEPQVYVLPPAQEELS-RNKVSVTCLIKSFHPPDIAVEWEITGQ | 172 |
| CAT_IGG1V2 | LPSPIERTISKAKGQPHEPQVYVLPPAQEELS-RNKVSVTCLIKSFHPPDIAVEWEITGQ | 172 |
| CAT_IGG2 | LPSAMERTISKAKGQPHEPQVYVLPPTQEELS-EINKVSVTCLIKGFHPPDIAVEWEITGQ | 173 |
| DOGA | LPSPIERTISKARGRAHKPSVYVLPPSPKELSSSDTVSITCLIKQFYPPDIDVEWQSNGQ | 170 |
| DOGD | LPSPIERTISKARGQAHQPGVYVLPPSPKELSSSDTVLITCLIKQFFPPEIDVEWQSNGQ | 168 |
| DOGC | LPSPIEEIISKTPGQAHQPNVYVLPPSRDEMS—KNTVLITCLVKQFFPPEIDVEWQSNGQ | 170 |
| DOGB | LPSPIERTISKARGQAHQPSVYVLPPSREELS-KNTVSLTCLIKQFFPPDIDVEWQSNGQ | 172 |
| DOGB-YTE | LPSPIERTISKARGQAHQPSVYVLPPSREELS-KNTVSLTCLIKQFFPPDIDVEWQSNGQ | 172 |
| HORSE_IGHG2 | VPQPISRAISRGKGPSRVPQVYVLPHPDELA-KSKVSVTCLVKQFYPPDISVEWQSNRW | 179 |
| HORSE_IGHG6 | LPAPVERTITKAKGELQDPKVYILAPHREEVT-KNTVSVTCLVKQFYPPDINVEWQSNEE | 161 |
| HORSE_IGHG3 | LPAPVERTISKATGQTRVPQVYVLAPHPDELS-KNKVSVTCLVKQFYPPEIDVEWQSNEH | 169 |
| HORSE_IGHG5 | LPAPVERTISKAKGQLRVPQVYVLAPHPDELA-KNTVSVTCLVKQFYPTDIDIEWKSNGQ | 167 |
| HORSE_IGHG1 | LPAPVERTISKPTGQPREPQVYVLAPHRDELS-KNKVSVTCLVKQFYPTDIDIEWKSNGQ | 166 |
| HORSE_IGHG4 | LPAPVERTISKPTGQPREPQVYVLAPHRDELS-KNKVSVTCLVKQFYPTDIDIEWKSNGQ | 166 |
| HORSE_IGHG7 | LPAPVQKTISKPTGQPREPQVYVLAPHRDELS-KNKVSVTCLVKQFYPTDIDIEWKSNGQ | 167 |
| | .:  :  * :         :     ::***: *. :** : |  |

| | | |
|---|---|---|
| CAT_IGG1V1 | PEPENNYRTTPPQLDSDGTYFVYSKLSVDRSHWQRGNTYTCSVSHEALHSHHTQKSLTQS | 232 |
| CAT_IGG1V2 | PEPENNYRTTPPQLDSDGTYFVYSKLSVDRSHWQRGNTYTCSVSHEALHSHHTQKSLTQS | 232 |
| CAT_IGG2 | PEPENNYQTTPPQLDSDGTYFLYSRLSVDKSRWQRGNTYTCSVSHEALHSHHTQKSLTQS | 233 |
| DOGA | QEPERKHRMTPPQLDEDGSYFLYSKLSVDKSRWQQGDPFTCAVMHETLQNHYTDLSLSHS | 230 |
| DOGD | PEPESKYHTTAPQLDEDGSYFLYSKLSVDKSRWQQGDPFTCAVMHEALQNHYTDLSLSHS | 228 |
| DOGC | QEPESKYRMTPPQLDEDGSYFLYSKLSVDKSRWQRGDTFICAVMHEALHNHYTQKSLSHS | 230 |
| DOGB | QEPESKYRTTPPQLDEDGSYFLYSKLSVDKSRWQRGDTFICAVMHEALHNHYTQKSLSHS | 232 |
| DOGB-YTE | QEPESKYRTTPPQLDEDGSYFLYSKLSVDKSRWQRGDTFICAVMHEALHNHYTQKSLSHS | 232 |
| HORSE_IGHG2 | PELEGKYSTTPAQLDGDGSYFLYSKLSLETSRWQQVESFTCAVMHEALHNHFTKTDISES | 239 |

FIG.2B Cont'd

```
HORSE_IGHG6  PEPEVKYSTTPAQLDSDGSYFLYSKLTVETDRWEQGESFTCVMHEAIRHTYRQKSITNF  221
HORSE_IGHG3  PEPEGKYRTTEAQKDSDGSYFLYSKLTVETDRWQQGTTFTCVMHEALHNHMQKNVSHS  229
HORSE_IGHG5  PEPEGKYSTTPAQLNSDGSYFLYSKLSVETSRWKQGESFTCGVMHEAVENHYTQKNVSHS  227
HORSE_IGHG1  PEPETKYSTTPAQLDSDGSYFLYSKLTVETNRWQQGTTFTCAVMHEALHNHYTEKSVSKS  226
HORSE_IGHG4  PEPETKYSTTPAQLDSDGSYFLYSKLTVETNRWQQGTTFTCAVMHEALHNHYTEKSVSKS  226
HORSE_IGHG7  PEPETKYSTTPAQLDSDGSYFLYSKLTVETNRWQQGTTFTCAVMHEALHNHYTEKSVSKS  227
             *    **::  *  *:***********:***.**::*  :*  **:*****   :  :

CAT_IGG1V1   PGK  235
CAT_IGG1V2   PGK  235
CAT_IGG2     PGK  236
DOGA         PGK  233
DOGD         PGK  231
DOGC         PGK  233
DOGB         PGK  235
DOGB-YTE     PGK  235
HORSE_IGHG2  PGK  242
HORSE_IGHG6  PGK  224
HORSE_IGHG3  PGK  232
HORSE_IGHG5  PGK  230
HORSE_IGHG1  PGK  229
HORSE_IGHG4  PGK  229
HORSE_IGHG7  PGK  230
             **
```

FIG. 2B Cont'd

| Sample | % Purity | Area | Δconc after FT |
|---|---|---|---|
| PetML119 | 99.39 | 333981 | 0 |
| PetML119 1FT | 99.39 | 322675 | −3.38522 |
| PetML119 2FT | 99.42 | 311886 | −6.61565 |

Freeze & Thaw stress

PetML119 showed good stability after 2 FT, showing no changes in oligomerisation with only minor protein loss (~5%)

FIG.4C

| # | Sample name | Sample MW | Sample Conc | Buffer type | pH | $T_{m1}$ (°C) | %CV | $T_{m2}$ (°C) | %CV |
|---|---|---|---|---|---|---|---|---|---|
| 1 | Protein_1* | 92 kDa | 3 mg/ml | PBS | 7.4 | 67.4 | 0.24 | 77.4 | 0.25 |
| 2 | Protein_1* | 92 kDa | 1.5 mg/ml | PBS | 7.4 | 67.1 | 0.31 | 77 | 0.71 |
| 3 | Protein_1* | 92 kDa | 0.75 mg/ml | PBS | 7.4 | 66.9 | 0.06 | 76.6 | 0.22 |

FIG.4D

Group 2
PetML119 CHO-s; 1:1 binding

Group 7
PetML119 CHOZN; 1:1 binding

Group 3
PetML122 CHO-s; 1:1 binding

Group 8
PetML122 CHOZN; 1:1 binding

Group 5
Bedinvetmab CHO-s; 1:1 binding

| Sample | Kinetics affinity KD (nM) |
|---|---|
| Bedinvetmab : ProtA | 0.01 |
| PetML119 (CHO-s) : ProtA | 2.8 |
| PetML119 (CHOZN) : ProtA | 1.3 |
| PetML122 (CHO-s) : ProtA | 10.6 |
| PetML122 (CHOZN) : ProtA | 15 |

Group 2
PetML119; dFcRn 1:1000 pH4.5; 1:1 binding

Group 12
PetML119; mFcRn 1:1000 pH4.5; 1:1 binding

| Sample | Steady state affinity KD (μM) |
|---|---|
| PetML119 : dog FcRn | 6 |
| PetML119 : mouse FcRn | 2 |

Group 8
PetML122; dFcRn 1:1000 pH4.5; 1:1 binding

| Sample | Steady state affinity KD ($\mu M$) |
|---|---|
| PetML122 : dog FcRn | 0.4 |
| PetML122 : mouse FcRn | 0.09 |

Group 2
hNGF; levi_p75-Fc-Bwt 500nM; 1:1 binding

Group 2
rNGF; levi_p75-Fc-Bwt 500nM; Bivalent analyte

| Sample | Kinetics affinity KD (nM) |
|---|---|
| PetML119: human NGF | 0.12 |
| PetML119: rat NGF | 0.12 |

| Sample | Kinetics affinity KD (nM) |
|---|---|
| BedinvetmAb human NGF | 0.073 |

|  | PetML119 5mg/kg | PetML119 1.25mg/kg | PetML119 0.5mg/kg | PetML122 5mg/kg |
|---|---|---|---|---|
| One phase decay |  |  |  |  |
| Best-fit values |  |  |  |  |
| Plateau | 2082 | 1471 | 355.7 | Unstable |
| Half Life | 59.68 | 56.66 | 70.01 | 418874 |

|  | PetML119 5mg/kg | PetML119 1.25mg/kg | PetML119 0.5mg/kg | PetML122 5mg/kg |
|---|---|---|---|---|
| One phase decay |  |  |  |  |
| Best-fit values |  |  |  |  |
| Plateau | 2082 | 1471 | 355.7 | Unstable |
| Half Life | 59.68 | 56.66 | 70.01 | 418874 |

THERAPEUTIC MOLECULES

RELATED APPLICATIONS AND INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

Sequence Statement

The instant application contains a Sequence Listing which has been submitted electronically and is hereby incorporated by reference in its entirety. Said ASCII copy, was created Oct. 8, 2021 and amended on Oct. 3, 2022, is named ReplacementY973600001SL.txt and is 86,847 bytes in size.

FIELD OF THE INVENTION

The present invention relates to effective pain therapies in companion animals.

Introduction

There is a huge need for therapies in veterinary medicine, in particular for pain relief.

Pain relief treatments for dogs currently include non-steroidal anti-inflammatory drugs, commonly called NSAIDs, and several nonsteroidal anti-inflammatory drugs which help to control pain and inflammation associated with osteoarthritis. Several NSAIDs have been approved by the FDA. However, there is a need for further effective pain treatments in companion animals with minimal side effects.

Nerve growth factor (NGF) was firstly discovered in 1950s. The NGF protein was then cloned and identified as part of brain-derived neurotrophic factor (BDNF), neurotrophin-3 and 4/5 (NT-3, NT-4-5). All of these are secreted proteins that promote survival and growth of the peripheral nervous system.

NGF causes peripheral sensitization both in vitro and in vivo, as illustrated by the increased response of DRG neurons to temperature or capsaicin in its presence. NGF also leads to transcriptional regulation after retrograde axonal transport, as illustrated by immunostaining showing upregulation of BDNF after intrathecal NGF treatment. Furthermore, NGF can cause sprouting of peripheral afferents into diseased joints and cancerous tissue (Denk et al, Annual Review of Neuroscience, Vol. 40:307-325, 2017).

NGF is expressed at low levels in adulthood, but injury, inflammation or release of NGF cause activation of inflammatory cells. These cells in turn produce and secrete NGF as well and this leads to short-term and long-term effects. NGF has a well-known and multifunctional role in nociceptive processing, although the precise signaling pathways downstream of NGF receptor activation that mediate nociception are complex and not completely understood. The role of NGF in nociception and the generation and/or maintenance of chronic pain has led to it becoming an attractive target of pain therapeutics for the treatment of chronic pain conditions (Barker et al, Journal of Pain Research, 2020:13 1223-1241).

Very low doses of monoclonal antibodies (mAbs) directed against NGF can reduce chronic pain. However, during clinical trials in humans, a small subset of patients treated with mAbs directed against NGF developed rapidly progressive joint degeneration due to interaction with NSAIDs treatment. Complete NGF removal is shown to cause impaired bone and cartilage repairing (Denk et al, Annual Review of Neuroscience, Vol. 40:307-325, 2017). Treatments for use in dogs and cats based on species-specific mAbs that target NGF are now being developed for the management of osteoarthritis (OA)-associated pain (Enomoto et al, Vet Rec. 2019 Jan. 5; 184(1):23 and WO2019177690). However, given the side effects that occurred in clinical trials in humans, there is a need to develop alternative treatments that target NGF.

Citation or identification of any document in this application is not an admission that such document is available as prior art to the present invention.

SUMMARY OF THE INVENTION

The invention is aimed at addressing a need for effective pain therapies in companion animals.

The invention provides a pain therapy for companion animals with reduced side effects compared to anti-NGF antibody therapies. The proteins of the invention bind NGF which is at elevated levels in pain conditions, thus binding to excess NGF to restore normal NGF levels without completely blocking NGF signalling. Without wishing to be bound by theory, the inventors believe that this ensures a level of NGF signalling which is required for healthy functions. Furthermore, it is believed that the fusion proteins of the invention can operate at a very low dose, but are highly efficacious.

The inventors have used an analgesic strategy to reduce, but not completely deplete, NGF in circulation. To this end, the Extracellular Domain (ECD) of p75 neurotrophin receptor (p75NTR) was used, fused to Fc to increase its half-life. p75NTR binds NGF and other brain-derived neurotrophic factors (NT3, NT4) and mediates different cellular activities.

The use of human p75 has been described for treatment of pain in humans (WO2013136078).

Thus, in a first aspect, the invention relates to an isolated companion animal p75NTR protein or a portion thereof. The invention also relates to an isolated nucleic acid encoding the protein or portion thereof.

The invention also relates to a vector comprising a nucleic acid as described above.

The invention further relates to a host cell comprising a nucleic acid as described above.

In another aspect, the invention relates to a fusion protein comprising an isolated companion animal p75NTR extracellular domain or portion thereof and a half-life extending moiety.

In another aspect, the invention relates to a nucleic acid encoding a fusion protein as described above. In another aspect, the invention relates to a vector comprising a nucleic acid as described above.

In another aspect, the invention relates to a host cell comprising a nucleic acid according as described above or a vector as described above.

In another aspect, the invention relates to a pharmaceutical composition comprising an isolated companion animal p75NTR protein as described above, or a fusion protein as described above.

In another aspect, the invention relates to a method for treating an NGF-related disorder in a companion animal comprising administering an isolated companion animal p75NTR protein as described above, a fusion protein as described above or a pharmaceutical composition as described above.

In another aspect, the invention relates to the use of an isolated companion animal p75NTR protein as described above, a fusion protein as described above or a pharmaceutical composition as described above in the treatment of an NGF-related disorder in a companion animal.

In another aspect, the invention relates to a method of inhibiting NGF activity in a companion animal comprising administering an isolated companion animal p75NTR protein as described above, a fusion protein as described above or a pharmaceutical composition as described above.

In another aspect, the invention relates to a kit comprising an isolated companion animal p75NTR protein as described above, a fusion protein as described above or a pharmaceutical composition of as described above and optionally instructions for use.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DESCRIPTION OF FIGURES

The invention is described in the following non-limiting figures.

FIG. 2a-2b.
a) Sequence alignment of part of the ECD of p75NTR as used in the fusion proteins of the invention. There is a very high similarity between species:
Canine vs Feline: 1/164 (more than 99% identical);
Canine vs Equine: 4/164 (97.6% identical);
Feline vs Equine: 5/164 (97% identical);
Canine vs Bovine: 2/164 (98.8% identical)
b) Sequence alignment of the Fc region (including CH3, CH2 and CH2-CH1 hinge) from different species/different isotypes.

FIG. 4a-4e. PetML119 Stability.
a) Tonset analysis.
b) Thermal and chemical stress.
c) Freeze and thaw stress.
d) Thermal stability.
e) Aggregation analysis.

DETAILED DESCRIPTION

Figure 1B:
FIG. 1a-1b. Exemplary fusion proteins.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Green and Sambrook et al., Molecular Cloning: A Laboratory Manual, 4th ed., Cold Spring Harbor Laboratory Press, Cold Spring Harbor, N.Y. (2012); Therapeutic Monoclonal Antibodies: From Bench to Clinic, Zhiqiang An (Editor), Wiley, (2009); and Antibody Engineering, 2nd Ed., Vols. 1 and 2, Ontermann and Duebel, eds., Springer-Verlag, Heidelberg (2010).

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The invention provides biological therapeutics for veterinary use, in particular fusion proteins for use in the treatment of companion animals such as dogs, cats, bovines or horses.

In a first aspect, the invention relates to an isolated companion animal p75NTR protein or a portion thereof.

As used herein, the term p75NTR protein refers to a p75NTR protein that binds NGF and/or other neurotrophins (BDNF, NT-3 and/or NT-4/5). As used herein, this means that the protein is capable of binding to NGF and inhibiting NGF biological activity and/or downstream pathway(s) mediated by NGF signalling. An NGF binding protein reduces NGF biological activity, including downstream pathways mediated by NGF signalling and/or reduces the amount of NGF that is in circulation and which can bind to its receptors trkA and NGFR (p75NTR).

The term companion animal as used herein refers to a dog, cat or horse. In one embodiment, the companion animal is a dog. In another embodiment, the animal to be treated may be a cow or pig.

The term "isolated" protein or polypeptide refers to a protein or polypeptide that is substantially free of other proteins or polypeptides, having different antigenic specificities. Moreover, protein or polypeptide may be substantially free of other cellular material and/or chemicals. Thus, the protein, nucleic acids and polypeptides described herein are preferably isolated. Thus, as used herein, an "isolated" protein, or polypeptide means protein or polypeptide that has been identified and separated and/or recovered from a component of its natural cell culture environment. Contaminant components of its natural environment are materials that would interfere with diagnostic or therapeutic uses for the protein or polypeptide, and may include enzymes, hormones, and other proteinaceous or non-proteinaceous solutes.

The terms "polypeptide" and "protein" are used interchangeably to refer to a polymer of amino acid residues and are not limited to a minimum length. Peptides, oligopeptides, dimers, multimers, and the like, are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational and post-translational modifications of the polypeptide, such as, for example, disulfide-bond formation, glycosylation, acetylation, phosphorylation, proteolytic cleavage (e.g., cleavage by furins or metalloproteases and prohormone convertases (PCs)), and the like. Furthermore, for purposes of the present invention, a "polypeptide" encompasses a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, have a well-defined conformation.

Proteins, as opposed to peptides, generally consist of chains of 50 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 50 amino acids in length.

By "amino acid" herein is meant one of the 20 naturally occurring amino acids or any non-natural analogues that may be present at a specific, defined position. Amino acid encompasses both naturally occurring and synthetic amino acids. Although in most cases, when the protein is to be produced recombinantly, only naturally occurring amino acids are used.

In one embodiment, the isolated companion animal p75NTR protein comprises or consists of canine, feline or bovine p75NTR protein. Therefore, in one embodiment, the isolated companion animal p75NTR protein comprises or consists SEQ ID NO: 1, 3, 5 or 36 a portion or a variant thereof or variant of a portion.

The p75 neurotrophin receptor p75NTR in its native form exists as a transmembrane glycoprotein. Family members are characterised by multiple cysteine-rich domains for ligand binding, a single transmembrane sequence extracellular domain (ECD), and a non-catalytic cytoplasmic domain.

Endogenous soluble ECD of p75NTR is produced by regulated proteolysis by α-secretase and γ-secretase that cleaves the protein near the membrane junction of the ECD. This is cleavage results in the release of the cytoplasmic domain which is free to bind NGF as a natural antagonist to NGF signalling.

In one embodiment, the isolated companion animal p75NTR protein or a portion thereof comprises or consists of the extracellular domain (ECD) or part thereof or a variant thereof. In one embodiment, α-secretase and γ-secretase cleavage sites within the ECD are removed. In one embodiment, the stalk region is removed. In one embodiment, the stalk region and α-secretase and γ-secretase cleavage sites within the ECD are removed.

In one embodiment, the isolated companion animal p75NTR extracellular domain is canine and comprises or consists of SEQ ID No. 7 or a variant thereof or a portion thereof, for example SEQ ID NO: 34.

The ECD of p75NTR has a stalk region (e.g. SEQ ID NO: 9, canine stalk region) that is prone to O-glycosylation. Glycosylation in proteins can cause manufacturing difficulties. Thus, in one embodiment, the isolated companion animal ECD may comprise deletions in the stalk region to reduce the number of O-glycosylation sites within the stalk region e.g. to form a truncated stalk region. A truncated stalk region may comprise any number of the amino acids of the stalk region. For example, the stalk region may comprise 1-10, 1-20, 1-30 amino acids. The stalk region may be removed in embodiments of the fusion protein described herein. Thus, a portion of the ECD as used herein may be the ECD without the stalk region and 3' sequences α-secretase and γ-secretase cleavage sites (e.g. canine sequence SEQ ID NO: 34).

Thus, in one embodiment, the isolated companion animal p75NTR is a truncated protein which has the O-glycosylation stalk region removed.

In one embodiment, the isolated companion animal p75NTR protein may be a variant of the wild type protein which comprises one or more amino acid modification compared to the wild type protein. The modification may be a substitution, deletion or addition of an amino acid.

By "variant" or "mutant" herein is meant a polypeptide sequence that differs from that of a wild-type sequence by virtue of at least one amino acid modification. As used herein, a "substitution of an amino acid residue" with another amino acid residue in an amino acid sequence of a protein or polypeptide as described herein, is equivalent to "replacing an amino acid residue" with another amino acid residue and denotes that a particular amino acid residue at a specific position in the original (e.g. wild type/germline) amino acid sequence has been replaced by (or substituted for) by a different amino acid residue. This can be done using standard techniques available to the skilled person, e.g. using recombinant DNA technology. The amino acids are changed relative to the native (wild type/germline) sequence as found in nature in the wild type (wt), but may be made in IgG molecules that contain other changes relative to the native sequence.

Variants of the p75NTR protein or portions thereof as used herein retain the biological function of the wild type protein, that is binding to NGFs.

Amino acid modifications in general refer to and include substitutions, insertions and deletions, with the former being preferred in many cases. The variants of the invention include amino acid substitutions, and they can include any number of further modifications, as long as the function of the protein is still present, as described herein. In one embodiment, from 1, 2, 3, 4, 5, 6, 7, 8, 9 or 10 modifications are generally utilized as often the goal is to alter function with a minimal number of modifications. A variant polypeptide sequence will preferably possess at least about 80%, 85%, 90%, 95% or up to 98% or 99% identity to the wild-type sequences or the parent sequences. It should be noted that depending on the size of the sequence, the percent identity will depend on the number of amino acids. Variants do not include human sequences.

By "protein variant" or "variant protein" herein is meant a protein that differs from a wild-type protein by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino acid sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% identity with a parent polypeptide sequence, and most preferably at least about 90% identity, more preferably at least about 95% identity. Variants do not include human sequences.

By "parent polypeptide", "parent protein" as used herein is meant an unmodified polypeptide that is subsequently modified to generate a variant. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it.

By "wild type" or "WT", "wt" or "native" herein is meant an amino acid sequence or a nucleotide sequence that is found in nature, including allelic variations. A WT protein, polypeptide, Fc domain, immunoglobulin etc. has an amino acid sequence or a nucleotide sequence that has not been intentionally modified.

In another aspect, the invention relates to an isolated nucleic acid encoding a companion animal p75NTR protein or a portion thereof, e.g. the ECD or a portion thereof. As used herein, a portion of p75NTR or a portion of the ECD of p75NTR includes at least one neurotrophin binding domain. In one embodiment, the companion animal is a dog. For example, the isolated nucleic acid comprises or consists of SEQ ID NO: 2, 4, 6, 8 or 37 or a variant thereof.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature or is linked to a polynucleotide to which it is not linked in nature.

In another aspect, the invention relates to a vector, plasmid, transcription, expression cassette or nucleic acid construct comprising a nucleic acid encoding a companion animal p75NTR protein or a portion thereof, e.g. the ECD or portion thereof as described above.

The construct may include a suitable leader sequence. The term leader sequence is used interchangeably with signal sequence. Thus, in some embodiments, the nucleic acid sequence/nucleic acid construct encoding the fusion protein may also comprise a leader sequence. The leader sequence is made as part of the protein and then cleaved off when the protein is secreted. Any suitable leader sequence may be used, including a native immunoglobulin germline leader sequence, such as the endogenous p75 leader of the relevant species (e.g. canine, equine, feline, bovine), the endogenous p75 leader of a different species e.g. human, canine, equine, feline, bovine or a mouse IgG leader or another leader sequences known in the art, e.g. the Campath leader sequence (see U.S. Pat. No. 8,362,208 B2) or an artificial sequence. Such leader sequences can aid in enhancing protein expression.

In another aspect, the invention relates to a host cell comprising a nucleic acid encoding a companion animal p75NTR protein or a portion thereof, e.g. the ECD, or a vector, plasmid, vector, transcription, expression cassette or construct as described above.

Expression vectors of use in the invention may be constructed from a starting vector such as a commercially available vector. After the vector has been constructed and the nucleic acid molecule has been inserted into the proper site of the vector, the completed vector may be inserted into a suitable host cell for amplification and/or polypeptide expression.

The term "vector" means a construct, which is capable of delivering, and in some aspects expressing one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The invention also relates to an isolated recombinant host cell comprising one or more nucleic acid molecule plasmid, vector, transcription or expression cassette as described above. The transformation of an expression vector into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used.

The host cell may be eukaryotic or prokaryotic, for example a bacterial, viral, plant, fungal, mammalian or other suitable host cell. In one embodiment, the cell is an *E. coli* cell. In another embodiment, the cell is a yeast cell. In another embodiment, the cell is a Chinese Hamster Ovary (CHO) cell, HeLa cell or other cell that would be apparent to the skilled person. Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides of the invention.

In general, host cells are transformed with a recombinant expression vector that comprises DNA encoding a protein. Among the host cells that may be employed are prokaryotes, yeast or higher eukaryotic cells. Prokaryotes include gram negative or gram-positive organisms, for example *E. coli* or bacilli. Higher eukaryotic cells include insect cells and established cell lines of mammalian origin. Examples of suitable mammalian host cell lines include the COS-7 cells, L cells, C127 cells, 3T3 cells, Chinese hamster ovary (CHO) cells, or their derivatives and related cell lines which grow in serum free media, HeLa cells, BHK cell lines, the CVIIEBNA cell line, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays.

Other suitable host cells include insect cells, using expression systems such as baculovirus in insect cells, plant cells, transgenic plants and transgenic animals, and by viral and nucleic acid vectors.

Alternatively, it is possible to produce the polypeptide in lower eukaryotes such as fungal cell lines and yeast or in prokaryotes such as bacteria. Suitable yeasts include *S. cerevisiae, S. pombe, Kluyveromyces strains, Pichia pastoris, Candida,* or any yeast strain capable of expressing heterologous polypeptides. Suitable bacterial strains include *E. coli, B. subtilis, S. typhimurium,* or any bacterial strain capable of expressing heterologous polypeptides. If the protein is made in yeast or bacteria, it may be desirable to modify the product produced therein, for example by phosphorylation or glycosylation of the appropriate sites, in order to obtain a functional product. Such covalent attachments can be accomplished using known chemical or enzymatic methods.

A host cell, when cultured under appropriate conditions, can be used to express a protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

In another aspect, the invention also relates to the use of an isolated companion animal p75NTR protein or a portion thereof as described above in a fusion protein with another moiety, e.g. with a half-life extending moiety as described in more detail below. Therefore, the p75NTR protein or a portion thereof can be provided covalently linked or couple to a half-life extending moiety. Alternatively, it may be provided incorporated in a liposome. The invention further relates to an isolated companion animal p75NTR protein or a portion thereof for use in therapy. Further, there is provided an isolated companion animal p75NTR protein or a portion thereof for use in the treatment of a pain related disease. Such diseases are described in more detail below.

In some embodiments, to improve its pharmacokinetic (PK) properties, the half-life of the p75NTR protein is extended.

Fusion Proteins

Thus, in another aspect, the invention relates to a fusion protein comprising an isolated companion animal p75NTR protein or portion thereof, e.g. the extracellular domain, as described above and another moiety.

For example, the other moiety may be a half-life extending moiety. Thus, the p75NTR protein or portion thereof is coupled to a half-life extending moiety. As described above, the p75NTR protein or portion may be canine, feline or equine. The p75NTR protein or portion used in the fusion protein may thus comprise or consist of a sequence selected from SEQ ID NO: 1, 3, 5, 7, 34 or 36 a portion or a variant thereof. In one embodiment of the canine p75NTR protein or portion, the stalk region (SEQ ID NO: 9) is removed.

Half-life extending moieties have been described. For example, the half-life extending moiety may be selected from the following non-limiting list: a companion animal immunoglobulin Fc domain, polyethylene glycol (PEG), PEG derivatives, simple lipids, lipid dicarboxylic acids, lipids with additional moieties, companion animal serum albumin binders, e.g. small-molecule binders or antibodies/antibody fragments that bind companion animal serum albumin, companion animal serum albumin, or streptococcal protein G's albumin-binding domain (ABD). Examples of lipids include glucagon-like peptide 1 (GLP-1), the analogs GLP-1 liraglutide and semaglutide or cholesterol. Advantageously, using an immunoglobulin Fc domain facilitates purification of the protein. In particular, Fc binding to Protein A can be used in purification procedures. The presence of an immunoglobulin Fc domain can also stabilise the overall folding of the fusion protein as well as extending its half-life.

In one embodiment, where the half-life extending moiety is a companion animal Fc domain, companion animal serum albumin binder or companion animal serum albumin, the p75NTR protein or portion and half-life extending moiety are from/specific to the same companion animal. For example, in one embodiment, the half-life extending moiety is a companion animal Fc domain of the corresponding companion animal. For example, if the p75NTR protein or portion thereof, e.g. the extracellular domain is canine, the Fc domain is canine. If the p75NTR protein or portion thereof, e.g. the extracellular domain is feline, the Fc domain is feline. If the p75NTR protein or portion thereof, e.g. the extracellular domain is equine, the Fc domain is equine. If the p75NTR protein or portion thereof, e.g. the extracellular domain is bovine, the Fc domain is bovine.

However, given the high sequence similarity between companion animal p75 protein, in another embodiment, where the half-life extending moiety is a companion animal Fc domain, companion animal serum albumin binder or companion animal serum albumin, the p75NTR protein or portion and half-life extending moiety are not from/specific to the same companion animal. For example, in one embodiment, the half-life extending moiety is the companion animal Fc domain of the corresponding companion animal, but the p75 protein or portion thereof is that of a different companion animal. For example, for treatment of dogs, if the Fc domain is canine, the p75NTR protein or portion thereof, e.g. the extracellular domain is may be from a different animal, e.g. cat, horse or cow. For example, for treatment of cats, if the Fc domain is feline, the p75NTR protein or portion thereof, e.g. the extracellular domain is may be from a different animal, e.g. dog, cow or horse. For example, for treatment of cats, if the Fc domain is equine, the p75NTR protein or portion thereof, e.g. the extracellular domain is may be from a different animal, e.g. cat, cow dog. In yet another embodiment, human p75 or a portion thereof fused to companion animal Fc can be used.

The companion animal serum albumin binder, e.g. antibody or fragment thereof, may be canine or caninized, feline of felinized, equine or equinized. The companion animal serum albumin binder may bind to canine, feline or equine serum albumin.

In one embodiment, the half-life extending moiety is a wild type or variant Fc domain. The term variant is as defined above. For example, an Fc domain variant may have modified half-life compared to the wild type Fc domain. In one embodiment, the Fc domain is a canine Fc domain, that is a wild type domain or a variant thereof. Variant Fc domains are described, for example in WO2020/142625.

By "Fc" or "Fc region" or "Fc domain" as used herein is meant the polypeptide comprising the constant region of an antibody excluding the first constant region immunoglobulin domain (CH1) and, in some cases, part of the hinge. In one embodiment, the Fc domain includes constant region immunoglobulin domains CH2, CH3 and the hinge region between CH1 and CH2 or part of the hinge region.

Proteolytic digestion of antibodies releases different fragments termed Fv (Fragment variable), Fab (Fragment antigen binding) and Fc (Fragment crystallisation). The Fc fragment comprises the carboxy-terminal portions of both H chains held together by disulfides. The constant domains of the Fc fragment are responsible for mediating the effector functions of an antibody.

In canine, there are four IgG heavy chains referred to as A, B, C, and D. These heavy chains represent four different subclasses of dog IgG, which are referred to as IgG-A, IgG-B, IgG-C and IgG-D. The DNA and amino acid sequences of these four heavy chains were first identified by Tang et al. (Vet. Immunol. Immunopathol. 80: 259-270 (2001)). Exemplary amino acid and DNA sequences for these heavy chains are also available from the GenBank data bases (IgGA: accession number AAL35301.1, IgGB: accession number AAL35302.1, IgGC: accession number AAL35303.1, IgGD: accession number AAL35304.1). Amino acid sequences for IgG-A, IgG-B, IgG-C and IgG-D as used by the inventors and according to the aspects and embodiments of the invention are provided as SEQ ID NOS: 15, 16, 17, 18).

In human, Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains CH2 and CH3 and the lower hinge region between CH1 and CH2. Although the boundaries of the Fc region may vary, the human IgG heavy chain Fc region is usually defined to include residues C226 or P230 to its carboxyl-terminus, wherein the numbering is according to the EU index as in Kabat.

Fc as used herein may refer to the Fc region in isolation, or this region in the context of an Fc fusion ("fusion composition" or "fusion construct"), as described herein. Fc domains include all or part of an Fc region; that is, N- or C-terminal sequences may be removed from wild-type or variant Fc domains, as long as this does not affect function.

Briefly, IgG functions are generally achieved via interaction between the Fc region of the Ig and an Fcγ receptor (FcγR) or another binding molecule, sometimes on an effector cell. This can trigger the effector cells to kill target cells to which the antibodies are bound through their variable (V) regions. Also, antibodies directed against soluble antigens might form immune complexes which are targeted to FcγRs which result in the uptake (opsonisation) of the immune complexes or in the triggering of the effector cells and the release of cytokines.

By "Fc gamma receptor", "FcγR" or "FcgammaR" as used herein is meant any member of the family of proteins that bind the IgG antibody Fc region and is encoded by an FcγR gene.

In humans, three classes of FcγR have been characterised, although the situation is further complicated by the occurrence of multiple receptor forms. The three classes are:

(i) FcγRI (CD64) including isoforms FcγRIa, FcγRIb, and FcγRIc binds monomeric IgG with high affinity and is expressed on macrophages, monocytes, and sometimes neutrophils and eosinophils;

(ii) FcγRII (CD32) binds complexed IgG with medium to low affinity and is widely expressed. These receptors can be divided into two important types, FcγRIIa and FcγRIIb. The 'a' form of the receptor is found on many cells involved in killing (e. g. macrophages, monocytes, neutrophils) and seems able to activate the killing process and occurs as two alternative alleles. The 'b' form seems to play a role in inhibitory processes and is found on B-cells, macrophages and on mast cells and eosinophils. On B-cells it seems to function to suppress further immunoglobulin production and isotype switching to for example, the IgE class. On macrophages, the b form acts to inhibit phagocytosis as mediated through FcγRIIa. On eosinophils and mast cells the b form may help to suppress activation of these cells through IgE binding to its separate receptor; and (iii) FcγRIII (CD16) binds IgG with medium to low affinity and exists as two types. FcγRIIIa is found on NK cells, macrophages, eosinophils and some monocytes and T cells and mediates ADCC. FcγRIIIb is highly expressed on neutrophils. Both types have different allotypic forms.

Canine Fc receptors are described in Bergeron et al L. M. Bergeron et al.; Veterinary Immunology and Immunopathology 157 (2014) 31-41. Canine has RI, RIIb, RIII, but not Riia.

As well as binding to FcγRs, IgG antibodies can activate complement and this can also result in cell lysis, opsonisation or cytokine release and inflammation. The Fc region also mediates such properties as the transportation of IgGs to the neonate (via the so-called "FcRn"), increased half-life (also believed to be effected via an FcRn-type receptor) and self-aggregation. The Fc-region is also responsible for the interaction with protein A and protein G (which interaction appears to be analogous to the binding of FcRn).

By "effector function" as used herein is meant a biochemical event that results from the interaction of an antibody Fc region with an Fc receptor or ligand. Effector functions include but are not limited to antibody-dependent cell-mediated cytotoxicity (ADCC), antibody-dependent cell-mediated phagocytosis (ADCP) and complement-dependent cytotoxicity (CDC).

In one embodiment, the companion animal p75NTR protein or portion thereof, e.g. the extracellular domain, and the other moiety are linked with a linker moiety or otherwise conjugated, attached or covalently or non-covalently linked. Suitable linkers are known to the skilled person. For example, the linker is a peptide linker, such as a glycine and/or alanine and/or threonine and/or serine-rich linker e.g. a glycine-serine linker, such as $(G_4S)_n$ SEQ ID NO: 38 wherein n is 1 to 4.

In another embodiment, the linker can be cleavable.

In one embodiment, the companion animal p75NTR protein or portion thereof comprises or consists of a canine p75NTR ECD or portion thereof. In one embodiment, the ECD comprises of consists of SEQ No. 7 or a variant thereof.

Thus, in one embodiment, the invention relates to a fusion protein comprising a canine p75NTR ECD linked to a canine Fc domain. In one embodiment, the ECD comprises of consists of SEQ No. 7 or a variant thereof.

In one embodiment, the fusion protein of the present invention preferably binds to any one or more of NGF, BDNF, NT3 or NT4/5 with a binding affinity (Kd) of between about 1pM to about 100 nM. In some preferred embodiments, the binding affinity (Kd) is between about 5 pM and any of about 10 pM, 20 pM, 40 pM, 50 pM 100 pM, 0.2 nM, 0.5 nM, InM 1.5 nM 2 nM, 2.5 nM, 3 nM, 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM, 15 nM, 20 nM, 25 nM, 30 nM, 35 nM, 40 nM, 45 nM, 50 nM or 100 nM as measured in an in vitro binding assay for NGF, BDNF, NT3 or NT4/5 such as described herein. Subnanomolar range is preferred.

Figure 1A:
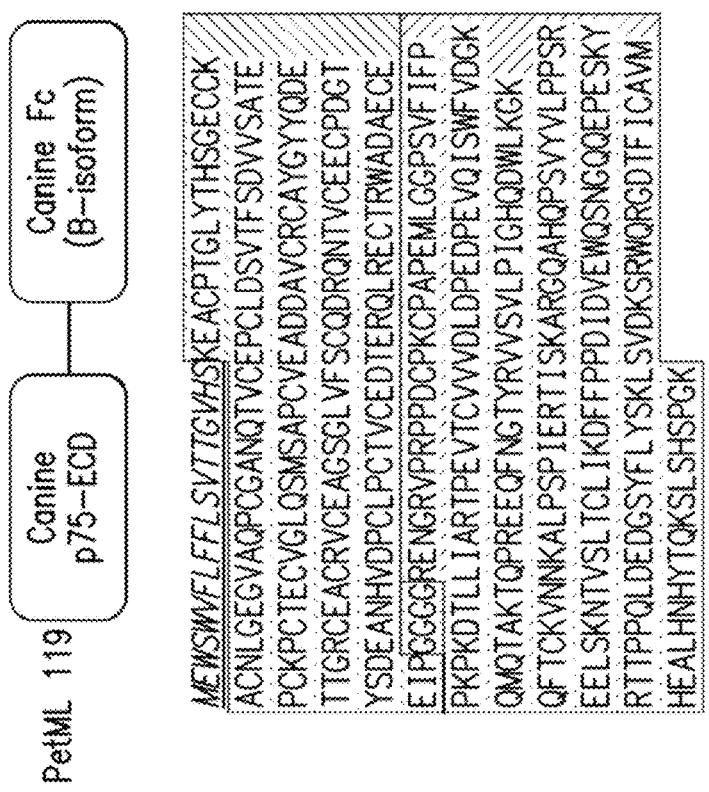

In one embodiment, the fusion protein comprises or consists of SEQ ID NO: 11 or 13 or a variant thereof. These fusion proteins include the p75 ECD operably linked to a canine Fc domain as shown in FIG. 1. The Fc domain in the construct of SEQ ID NO: 11 is a wild type canine Fc domain. The Fc domain in the construct of SEQ ID NO: 13 is a variant canine Fc domain which has been modified to increase half-life. In this domain, the mutation YTE has been introduced at residues Y252-T254- of the wt Fc domain using EU numbering.

Therefore, modified companion animal Fc domains that include this mutation, e.g. canine, feline or equine Fc domains, can be used in the fusion proteins of the invention.

A skilled person would know that any other known mutations that increase half-life could also be introduced in the Fc domain.

According to the present invention, the fusion protein demonstrates advantageous biological properties of improved solubility, stability and/or improved serum half-life p75NTR protein or a portion thereof.

In one embodiment, the fusion protein of the invention has a half-life in-vivo of about or more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 hours+/−1 hour, further preferably the p75NTR(NBP)-Fc fusion protein of the invention has a half-life in-vivo of about or more than 24 hours.

In another embodiment, the fusion protein of the invention has a half-life in-vitro of about or more than any one of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 62, 164, 166, 168, 170, 172, 174, 176, 178, 180, 182, 184, 186, 188, 190, 192, 194, 196, 198, 200, 202, 204, 206, 208 or 210 days+/−1 day, further the fusion protein has a half-life in-vitro of about or more than 6 days or more than 1 month. In one embodiment, the half life is 14 days.

According to the foregoing preferred embodiments, the in-vivo half-life can be the half-life in rat or in the corresponding companion animal, e.g. in a dog.

In another aspect, the invention relates to an isolated nucleic acid encoding a fusion protein as described above, for example a fusion protein encoding SEQ ID NO: 11 or 13. In one embodiment, the nucleic acid is selected from SEQ ID NO: 12 or 14.

In another aspect, the invention relates to a vector, plasmid, vector, transcription, expression cassette or construct comprising a nucleic acid described above.

In another aspect, the invention relates to a host cell comprising a nucleic acid vector, plasmid, vector, transcription, expression cassette or construct as described above. Suitable host cells are described elsewhere herein.

In another embodiment, the P75NTR protein, portion thereof or fusion protein is labelled with a detectable or functional label. A label can be any molecule that produces or can be induced to produce a signal, including but not limited to fluorophores, fluorescers, radiolabels, enzymes, chemiluminescers, a nuclear magnetic resonance active label or photosensitizers. Thus, the binding may be detected and/or measured by detecting fluorescence or luminescence, radioactivity, enzyme activity or light absorbance.

In another aspect, there is provided a pharmaceutical composition comprising a p75NTR protein or portion thereof or a fusion protein of the invention. The fusion protein or pharmaceutical composition described herein can be administered by any convenient route, including but not limited to oral, topical, parenteral, sublingual, rectal, vaginal, ocular, intranasal, pulmonary, intradermal, intravitrial, intratumoural, intramuscular, intraperitoneal, intravenous, subcutaneous, intracerebral, transdermal, transmucosal, by inhalation, or topical, particularly to the ears, nose, eyes, or skin or by inhalation. In another embodiment, delivery is of the nucleic acid encoding the drug, e.g. a nucleic acid encoding the molecule of the invention is delivered.

Parenteral administration includes, for example, intravenous, intramuscular, intraarterial, intraperitoneal, intranasal, rectal, intravesical, intradermal, topical, intra-articular or subcutaneous administration. Preferably, the compositions are administered parenterally.

The pharmaceutically acceptable carrier or vehicle can be particulate, so that the compositions are, for example, in tablet or powder form. The term "carrier" refers to a diluent, adjuvant or excipient, with which a drug antibody conjugate of the present invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the polypeptide of the present invention or compositions and pharmaceutically acceptable carriers are sterile. Water is a preferred carrier when the drug antibody conjugates of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The pharmaceutical composition can be in the form of a liquid, e.g., a solution, syrup, solution, emulsion or suspension. The liquid can be useful for oral administration or for delivery by injection, infusion (e.g., IV infusion) or subcutaneous.

When intended for oral administration, the composition can be in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose ordextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent. When the composition is in the form of a capsule (e. g. a gelatin capsule), it can contain, in addition to materials of the above type, a liquid carrier such as polyethylene glycol, cyclodextrin or a fatty oil.

When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

Compositions can take the form of one or more dosage units.

In specific embodiments, it can be desirable to administer the composition locally to the area in need of treatment, or by intravenous injection or infusion.

The amount of the polypeptide, Fc domain or pharmaceutical composition described herein that is effective/active in the treatment of a particular disease or condition will depend on the nature of the disease or condition and can be determined by standard clinical techniques. In addition, in vitro or in vivo assays can optionally be employed to help identify optimal dosage ranges. The precise dose to be employed in the compositions will also depend on the route of administration, and the seriousness of the disease or disease, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account.

Typically, the amount is at least about 0.01% of a polypeptide of the present invention by weight of the composition. When intended for oral administration, this amount can be varied to range from about 0.1% to about 80% by weight of the composition. Preferred oral compositions can comprise from about 4% to about 50% of the polypeptide of the present invention by weight of the composition.

Compositions can be prepared so that a parenteral dosage unit contains from about 0.01% to about 2% by weight of the polypeptide of the present invention.

For administration by injection, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight. In one embodiment, the composition is administered at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks or more.

Treatment can for example be once a month or bi-monthly.

As used herein, "treat", "treating" or "treatment" means inhibiting or relieving a disease or disease. For example, treatment can include a postponement of development of the symptoms associated with a disease or disease, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., canine patients, being treated. Many medical treatments are effective for some, but not all, patients that undergo the treatment.

The term "subject" or "patient" refers to an animal which is the object of treatment, observation, or experiment, suitably a companion animal, specifically a canine.

In another aspect, the invention relates to the use of a p75NTR protein or portion thereof, fusion protein or pharmaceutical composition described herein in the treatment or prevention of a disease. In another aspect, the disclosure relates to the use of a polypeptide, Fc domain or pharmaceutical composition described herein in the manufacture of a medicament for the treatment or prevention of a disease as listed herein. The invention further relates to a method of treating a disease in a subject comprising an effective amount of the polypeptide, Fc domain or pharmaceutical composition as described herein to said subject.

For example, the disease is a NGF related disorder.

In one embodiment, the NGF related disorder is selected from the group consisting of: cardiovascular diseases, atherosclerosis, obesity, type 2 diabetes, metabolic syndrome, pain and inflammation. In one embodiment, the NGF related disorder comprises pain. In one embodiment, the pharmaceutical composition is used in the treatment of pain. In one embodiment, the pharmaceutical composition is used for the treatment of a pain and the type of pain is selected from osteoarthritis pain, rheumatoid arthritis pain, surgical and postsurgical pain, incisional pain, general inflammatory pain, cancer pain, pain from trauma, neuropathic pain, neuralgia, diabetic neuropathy pain, pain associated with rheumatic diseases, pain associated with musculoskeletal diseases, visceral pain, and gastrointestinal pain. In one embodiment, the pain comprises osteoarthritis pain. In one embodiment, the pain comprises surgical and post-surgical pain. In one embodiment, the pain comprises cancer pain.

In one or more embodiments, the p75NTR protein or portion thereof, fusion protein or pharmaceutical composition of the invention is for use in a canine. In one or more embodiments, the p75NTR protein or portion thereof, fusion protein or pharmaceutical composition of the invention is for use in felines. In one or more embodiments, the p75NTR protein or portion thereof, fusion protein or pharmaceutical composition of the invention is for use in equine.

In one embodiment, the p75NTR protein or portion thereof, fusion protein or pharmaceutical composition of the invention is administered together with one or more therapeutic agent, for example a therapeutic agent to treat pain.

The polypeptide, the p75NTR protein or portion thereof, fusion protein or pharmaceutical composition may be administered at the same time or at a different time as the other therapy or therapeutic compound or therapy, e.g., simultaneously, separately or sequentially.

The invention also provides an in vitro or in vivo method for inhibiting NGF activity in a companion animal comprising administering the p75NTR protein or portion thereof, fusion protein or pharmaceutical composition of the invention.

In one or more aspects, the present invention provides a method of producing the fusion protein of the invention by culturing the host cell of the invention under conditions that result in production of the fusion protein and subsequently isolating the fusion protein from the host cell or culture medium of the host cell.

In another aspect, the invention provides a kit for the treatment or prevention of a disease, diagnosis, prognosis or monitoring disease comprising a the p75NTR protein or portion thereof, fusion protein or pharmaceutical composition of the invention of the invention. Such a kit may contain other components, packaging and/or instructions.

The invention in another aspect provides a the p75NTR protein or portion thereof, fusion protein or pharmaceutical composition of the invention packaged in lyophilized form or packaged in an aqueous medium.

In another aspect, a p75NTR protein or portion thereof, fusion protein or pharmaceutical composition of the invention as described herein is used for non-therapeutic purposes, such as diagnostic tests and assays. Thus, the present invention also provides the above p75NTR proteins and fusion proteins for use in diagnostic methods for detecting NGF in species, particularly canines and felines, known to be or suspected of having an NGF related disorder. Methods for detecting NGF in species, particularly canines and felines, known to be or suspected of having an NGF related disorder may include exposing a sample from the animal to a labelled protein of the invention and detecting said labelled protein. may be used to quantitatively or qualitatively detect the NGF in a sample or to detect presence of cells that express the NGF.

Further aspects and embodiments of the invention will be apparent to those skilled in the art given the present disclosure including the following experimental exemplification.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including any references to gene accession numbers and references to patent publications.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

Then invention is further described in the following non-limiting clauses.

1. An isolated companion animal p75NTR protein or a portion thereof.
2. An isolated companion animal p75NTR protein or a portion thereof according to clause 1 wherein the companion animal is a cat, dog, pig, cow or horse.
3. An isolated companion animal p75NTR protein or a portion thereof according to clause 2 wherein the companion animal is a dog.
4. An isolated companion animal p75NTR protein or a portion thereof according to clause 3 comprising SEQ ID NO: 1.
5. An isolated companion animal p75NTR protein or a portion thereof according to a preceding clause wherein the p75NTR protein or a portion thereof comprises the extracellular domain or part thereof.
6. An isolated companion animal p75NTR extracellular domain according to clause 6 wherein the companion animal is a dog and the p75NTR extracellular domain comprises SEQ ID NO: 2.
7. An isolated nucleic acid encoding a companion animal p75NTR protein or a portion thereof according to a preceding clause.
8. An isolated nucleic acid according to clause 7 wherein the companion animal is a dog and the nucleic acid comprises SEQ ID NO: 3.

9. A vector comprising a nucleic acid according to clause 7 or 8.
10. A host cell comprising a nucleic acid according to clause 7 or 8 or a vector according to clause 10.
11. A fusion protein comprising an isolated companion animal p75NTR extracellular domain or portion thereof and a half-life extending moiety.
12. A fusion protein according to clause 11 wherein the half-life extending moiety is selected from an Fc domain, a serum albumin binder or PEG.
13. A fusion protein according to clause 12 wherein the half-life extending moiety is a wild type or mutant Fc domain.
14. A fusion protein according to any of clauses 11 to 13 wherein the half-life extending moiety is an Fc domain and the p75NTR extracellular domain or portion thereof and the Fc domain are linked with a linker.
15. A fusion protein according to clause 14 wherein the linker is a peptide linker.
16. A fusion protein according to clause 15 wherein the peptide linker is $(G_4S)_n$ SEQ ID NO: 38 wherein n is 1 to 4.
17. A fusion protein according to any of clauses 11 to 16 wherein the companion animal is a cat, dog or horse.
18. A fusion protein according to clause 17 wherein the companion animal is a dog.
19. A fusion protein according to clause 18 wherein the p75NTR extracellular domain comprises SEQ ID NO: 7 or a portion thereof such as SEQ ID NO: 34.
20. A fusion protein according to any of clauses 12 to 19 wherein the Fc domain is a canine Fc domain.
21. A fusion protein according to clause 21 comprising SEQ ID NO: 11 or 13.
22. A nucleic acid encoding a fusion protein according to any of clauses 11 to 22.
23. A vector comprising a nucleic acid according to clause 23.
24. A host cell comprising a nucleic acid according to clause 22 or a vector according to clause 23.
25. A pharmaceutical composition comprising an isolated companion animal p75NTR protein according to any of clauses 1 to 6, or a fusion protein according to any of clauses 11 to 21.
26. A method for treating an NGF-related disorder in a companion animal comprising administering an isolated companion animal p75NTR protein according to any of clauses 1 to 6, a fusion protein according to any of clauses 11 to 21 or a pharmaceutical composition of clause 25.
27. The use of an isolated companion animal p75NTR protein according to any of clauses 1 to 6, a fusion protein according to any of clauses 11 to 21 or a pharmaceutical composition of clause 25 in the treatment of an NGF-related disorder in a companion animal.
28. The method of clause 26 or the use of clause 27 wherein the NGF-related disorder is cardiovascular diseases, atherosclerosis, obesity, type 2 diabetes, metabolic syndrome, pain and inflammation.
29. The method or use of clause 28 wherein the NGF-related disorder is a pain related disorder.
30. The method or use of clause 29 wherein pain is selected from osteoarthritis pain, rheumatoid arthritis pain, surgical and postsurgical pain, incisional pain, general inflammatory pain, cancer pain, pain from trauma, neuropathic pain, neuralgia, diabetic neuropathy pain, pain associated with rheumatic diseases, pain associated with musculoskeletal diseases, visceral pain, and gastrointestinal pain.
31. A method of inhibiting NGF activity in a companion animal comprising administering an isolated companion animal p75NTR protein according to any of clauses 1 to 6, a fusion protein according to any of clauses 11 to 21 or a pharmaceutical composition of clause 25.
32. The method or use of clause 29 or clause 30 or the method of clause 31 comprising administration of a second compound that treats pain.
33. A kit comprising an isolated companion animal p75NTR protein according to any of clauses 1 to 6, a fusion protein according to any of clauses 11 to 21 or a pharmaceutical composition of clause 25 and optionally instructions for use.

The invention is further described in the non-limiting examples.

EXAMPLES

Methods:
1. Protein Constructs and CHO-s Transfection/Expression (FIG. 1)

For protein production, DNA constructs were generated to encode chimeric Fc fusion protein comprising selected canine IgG constant regions (between hinge and C-terminus) fused to the extracellular domain of canine p75 lacking the predicted O-glycosylation rich stalk region and the α- and γ-secretase sites.

The amino acid sequences for PetML119 (SEQ ID NO: 11) and PetML122 (SEQ ID NO: 13) are given in FIG. 1. An alignment of canine, feline, bovine and equine p75 sequence portions is provided in FIG. 2.

Both the canine IgG-B Fc domain and the p75 extracellular domain (res 31-194 from UniProtKB-J9PAM0) were codon optimised and synthesised by GeneArt (Thermo Fisher). Both genes were PCR amplified using Q5 high fidelity DNA polymerase (using specific primers including overlapping regions to allow assembly) and assembled into mammalian expression vector PetML119 (Fc-Bwt) and PetML122 (Fc-B-YTE with the mutated residues Y252-T254-E256 using EU numbering) using NEBuilder HIFI DNA Assembly (New England Biolabs). In the expression vector, the fusion protein chain and the antibiotic resistant gene expression units are flanked by DNA transposon piggyBac terminal inverted repeats to mediate stable integration into host cells in the presence of piggyBac transposase. Both expression vectors also contain puromycin resistant cassette which is located within the piggyBac terminal repeats to facilitate selection for stable integration. To generate stable expression cell lines, PetML119 or PetMI122 was transfected into a suitable mammalian cell line such as CHO cells together with PiggyBac transposase followed by puromycin selection at 10-30 μg/ml for at least 8-10 days. For fusion protein production, $1 \times 10^6$/mL selected CHO cells are seeded in 800 mL culture media (F17+4 mM l-Gln+0.3% P188+1:500 ACA) and incubated at 32° C., 8% $CO_2$ with shaking at 130 rpm. 2% HyClone Cell Boost 7a supplement+0.2% HyClone Cell Boost 7b supplement 2 mM glucose is added to the media daily from the $4^{th}$ day of overproduction. Culture supernatants are collected on day 10 and the protein concentration is determined using surface plasmon resonance using protein A chip (Biacore 8K, Cytiva Life Sciences). Typically, PetML119/122 showed peak of expression at 10 day in production reaching around 70 mg/L.

2. PetML119-122 Purification

Cell suspensions from PetML119 and PetML122 stable transfected clones, cultured as described for at least 7 days, were filtered using 0.22 um filters after being incubated for 10 minutes with Sartoclear Dynamics® Lab V (SDLV-0500-20C-E). Cleared supernatants have been loaded into Mabselect sure LX prepacked 20 mL column (17547402), pre-equilibrated with PBS. Column was washed with 40 mLs of PBS (2CV) and then fusion proteins were eluted using gradient (0-100% in 2CV) of 0.1M Glycine pH2.7. Fractionations containing fusion proteins have been pooled together and neutralised with 100 mM TRIS pH8 (final concentration).

Neutralised fusion protein pooled fractions were concentrated till 5 mL and loaded into PBS pre-equilibrated HiLoad 16/600 Superdex 200 pg (28989335) as second step purification. Monomeric fractions (based on previously analysed protein standards' retention times) were pooled and protein concentration was assessed using NanoDrop™ One (Thermo Scientific™).

Around 30 mg/L of purified product was obtained following the above mentioned protocol.

PetML119 showed 34 mg/L final recovery after two step purification (with acceptable Endotoxin and HCP using standard protocols and buffers).

PetML122 showed 28 mg/L final recovery after two step purification (with acceptable Endotoxin and HCP using standard protocols and buffers).

Figure 3A:
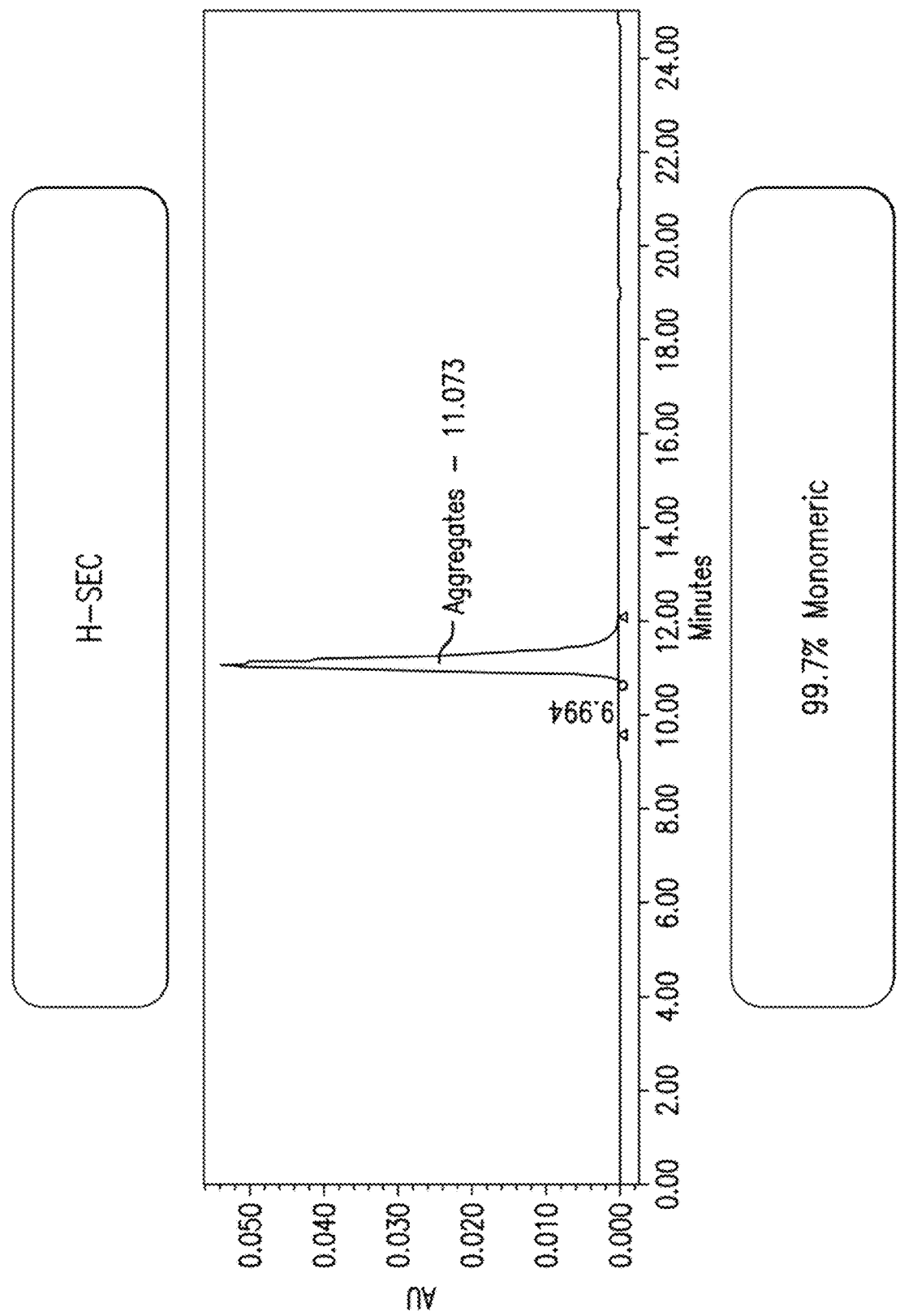
FIG. 3a-3b. Purity of isolated fusion proteins. a) H-SEC b) H-SCX. PetML119 appears to be highly pure by analytical size exclusion chromatography. b) Cation exchange chromatography showed presence of one main species (~80%) and two minor charge variants.
Figure 3B:
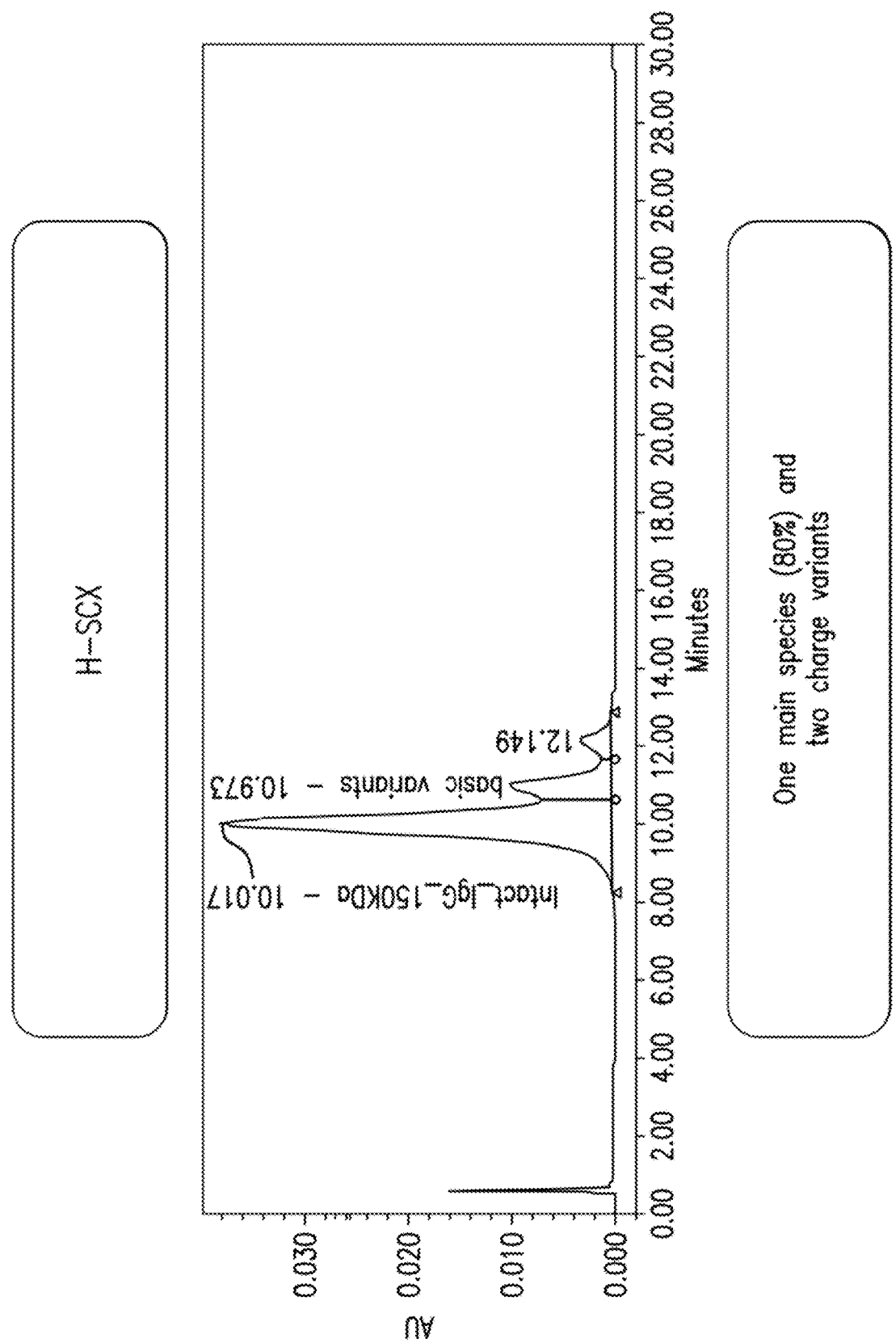

3. HPLC Analytical Chromatography (FIG. 3)

Purified material purity was assessed using both Size Exclusion Chromatography (SEC), for oligomerisation analyses, and cation exchange chromatography (SCX) for charge variants analyses.

HPLC-SEC chromatography (column: BioResolve SEC mAb 200 A, 2.5 um column WATERS) was performed using ACQUITY H-class Bio from WATERS using PBS as mobile phase with isocratic 0.575 mL/min flow rate.

HPLC-SCX chromatography (column: BioResolve SCX mAb Column, 3 μm, 4.6 mm×100 mm) was performed using ACQUITY H-class Bio from WATERS using MES pH5 as mobile phase with salt gradient used to separate charge variants at 0.9 mL/min flow rate.

10 uL of each sample were injected into both H-SEC/H-SCX using the above-mentioned protocol. Percentage of monomeric species and Area (indicative of protein concentration) were determined for each molecule.

Both PetML119/122 showed very high purity (more than 99%) by HSEC and few charge variants (potentially corresponding to different glycoforms) were observed by HSCX.

Figure 4A:
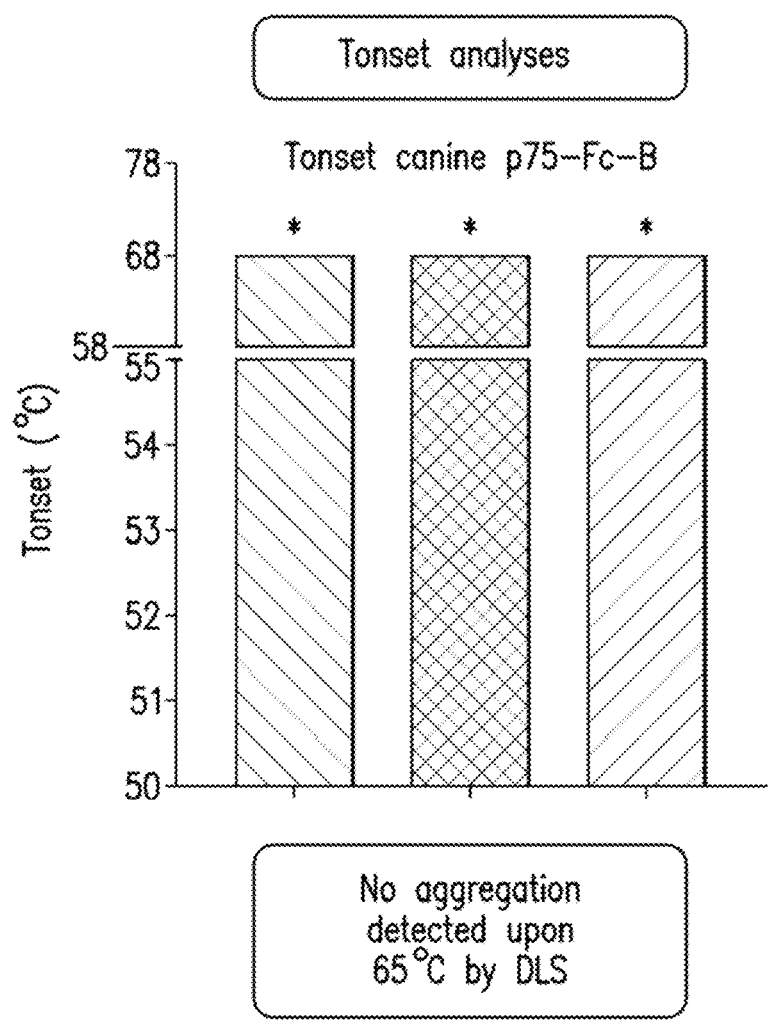
Figure 4B:
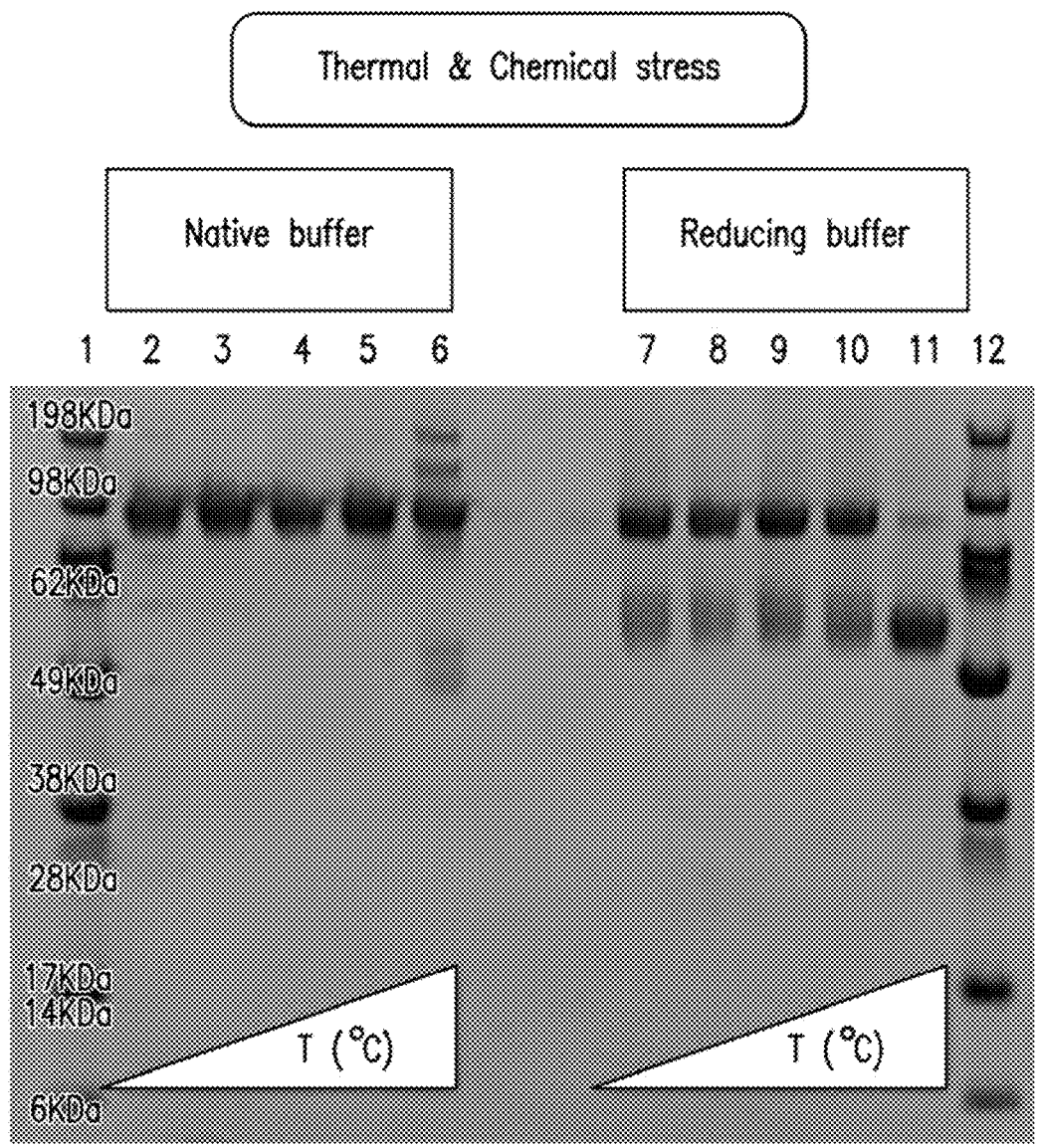
Figure 4E:
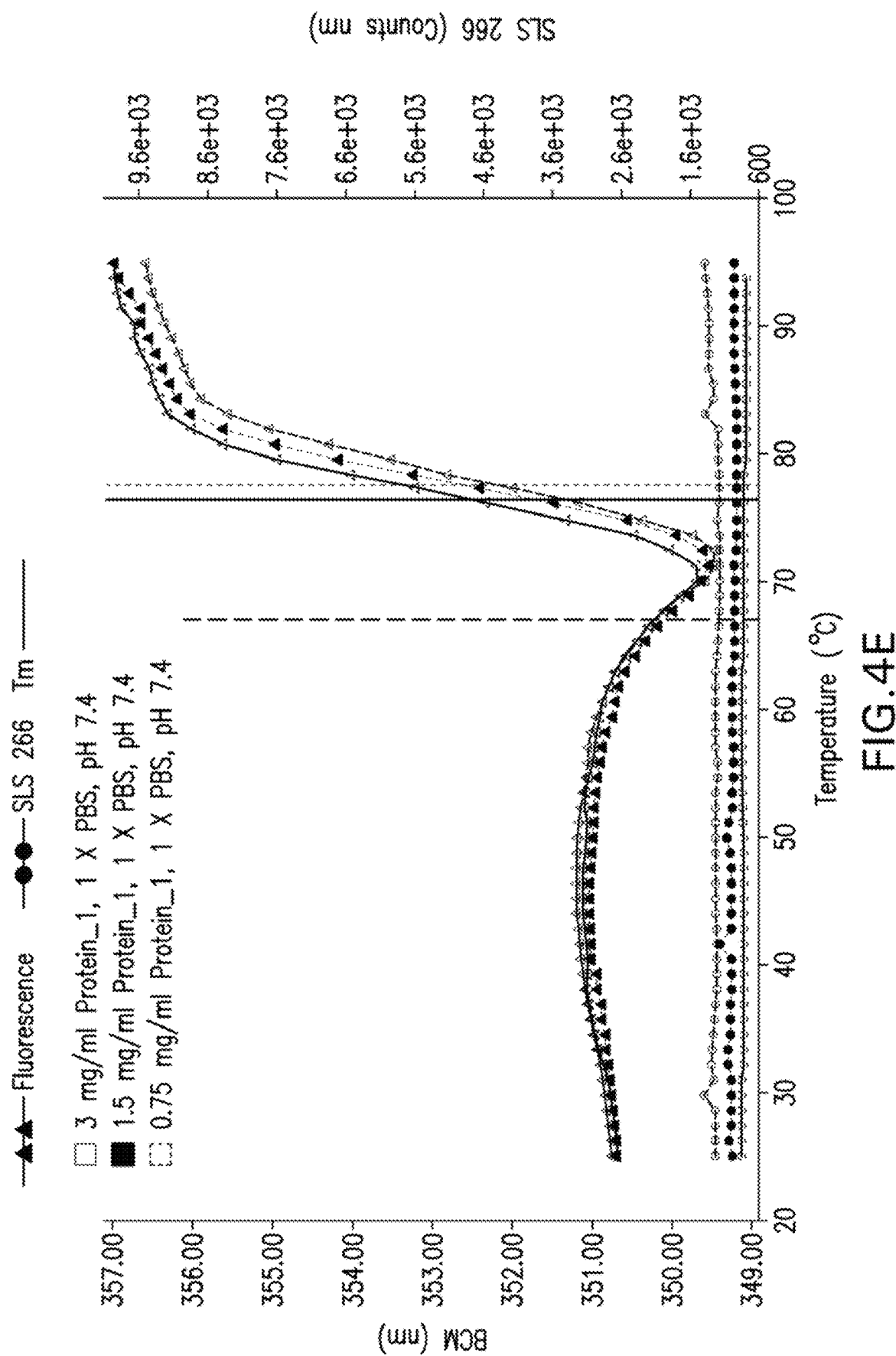
Figure 5A:
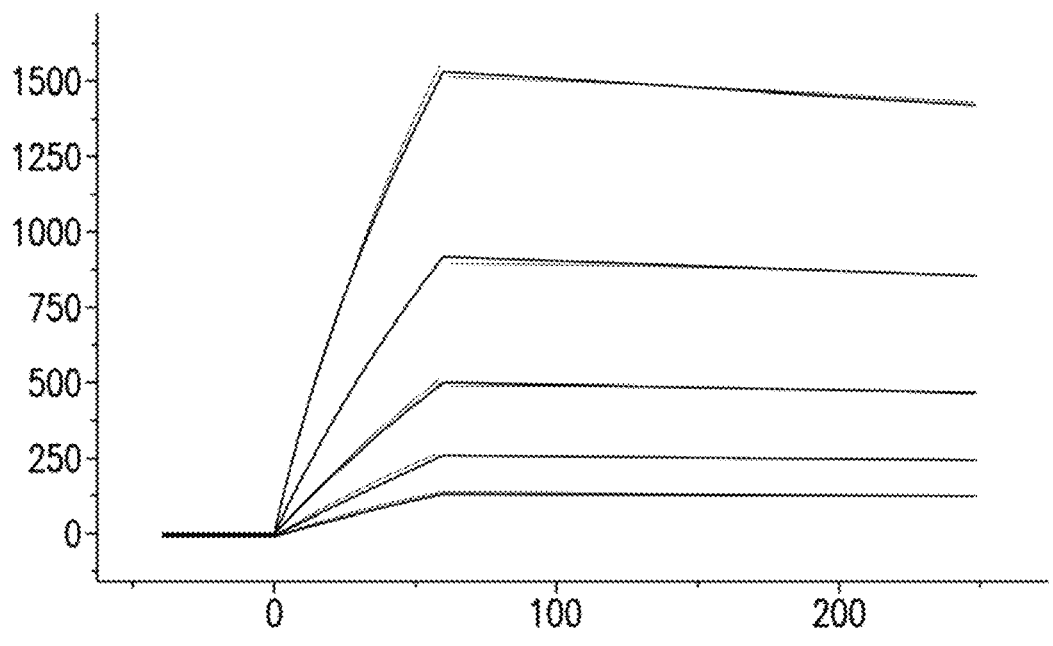
FIG. 5a-5f. Protein A binding
a) and b) PETML119 Protein A binding.
c) and d) PetML122 Protein A binding.
e) Bedinvetmab Protein A binding. Bedinvetmab is an anti-NGF IgG control,
f) Table showing kinetics.
Figure 5B:
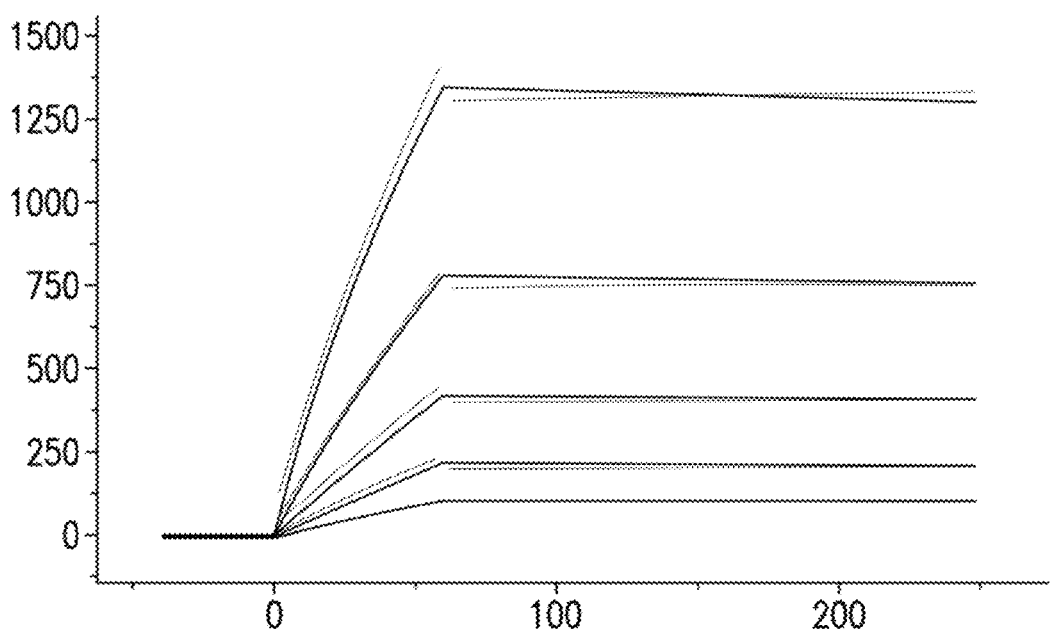
Figure 5C:
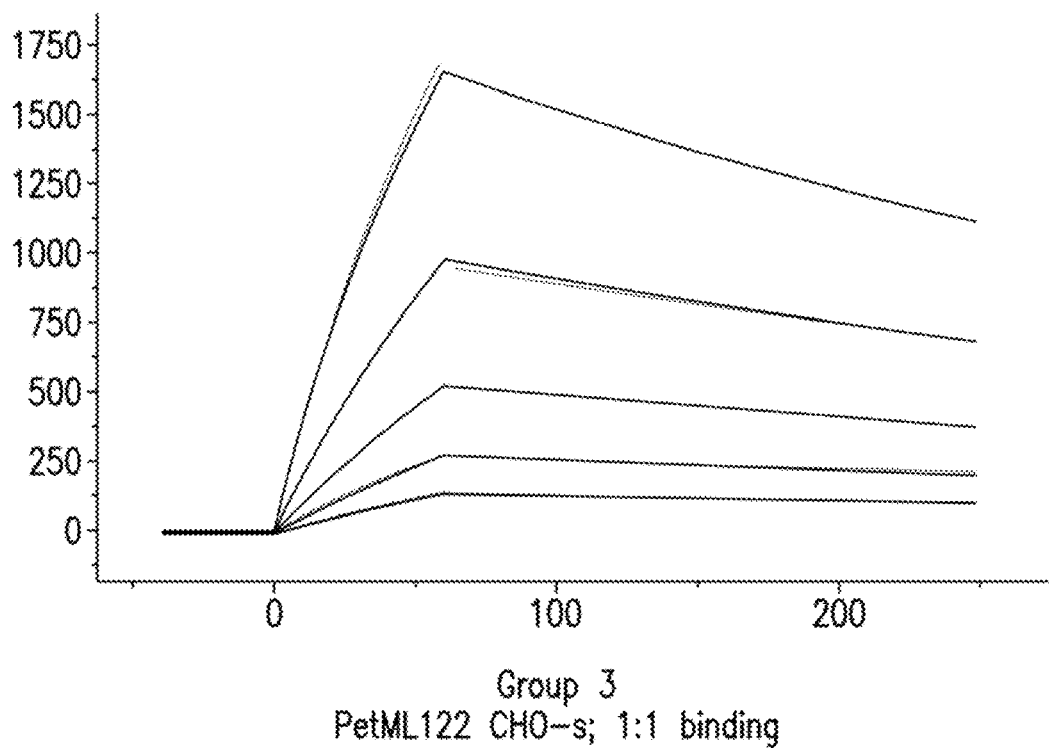
Figure 5D:
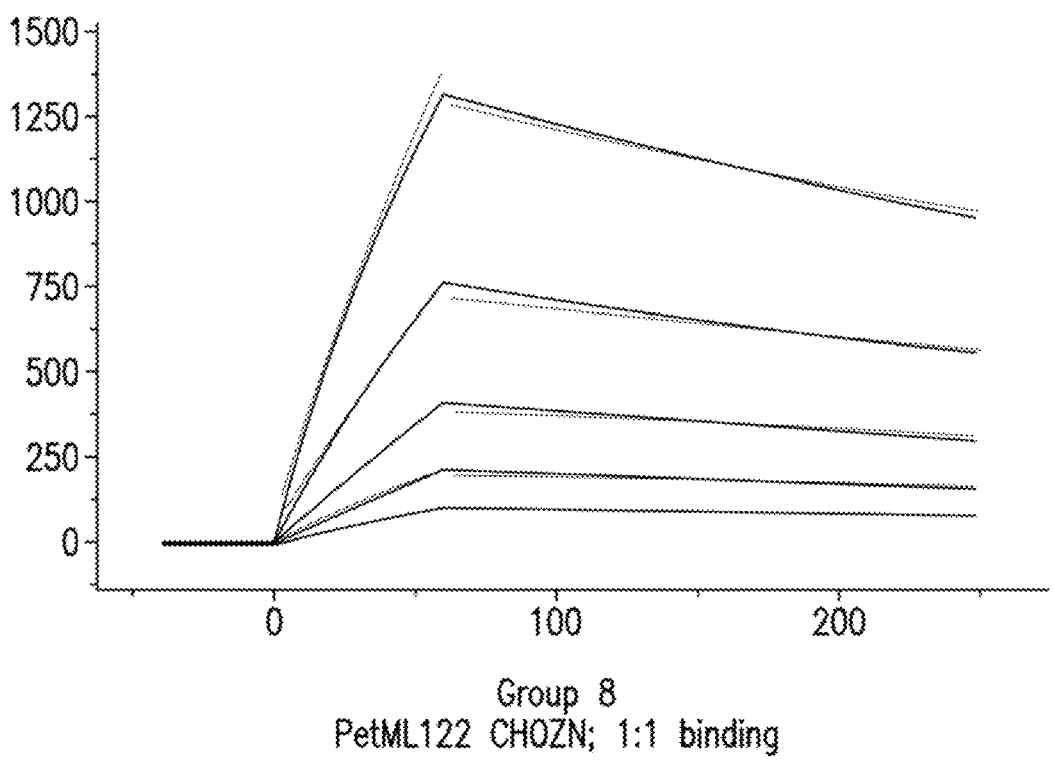
Figures 5E, 5F:
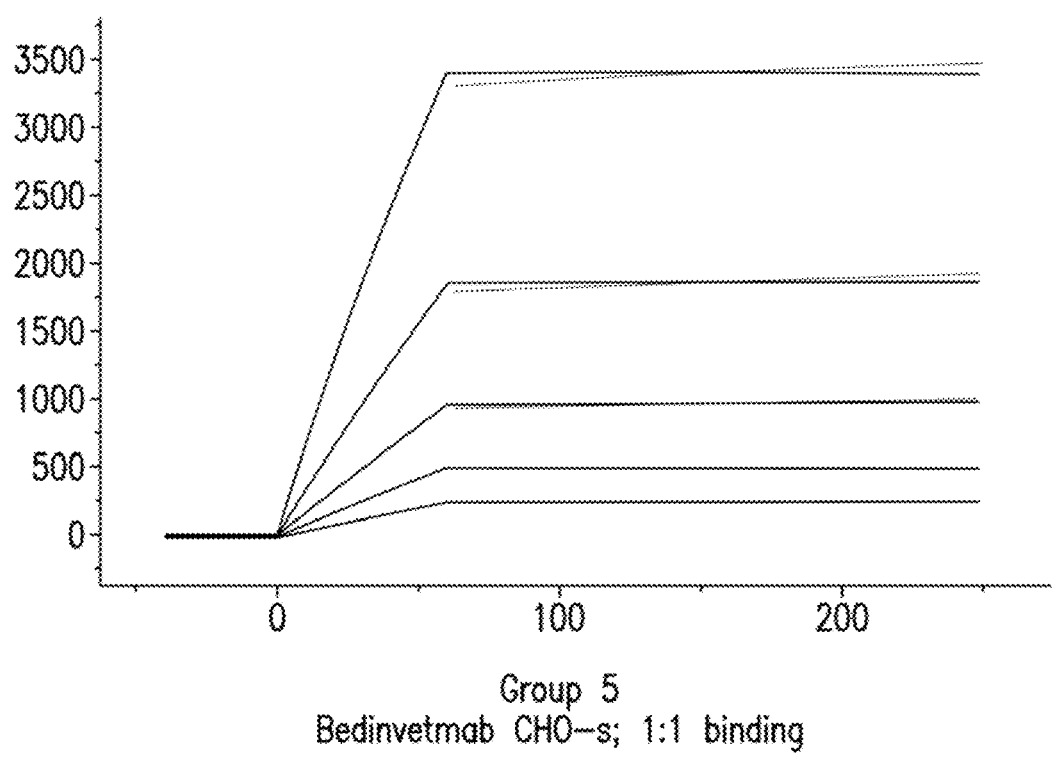
Figure 6A:
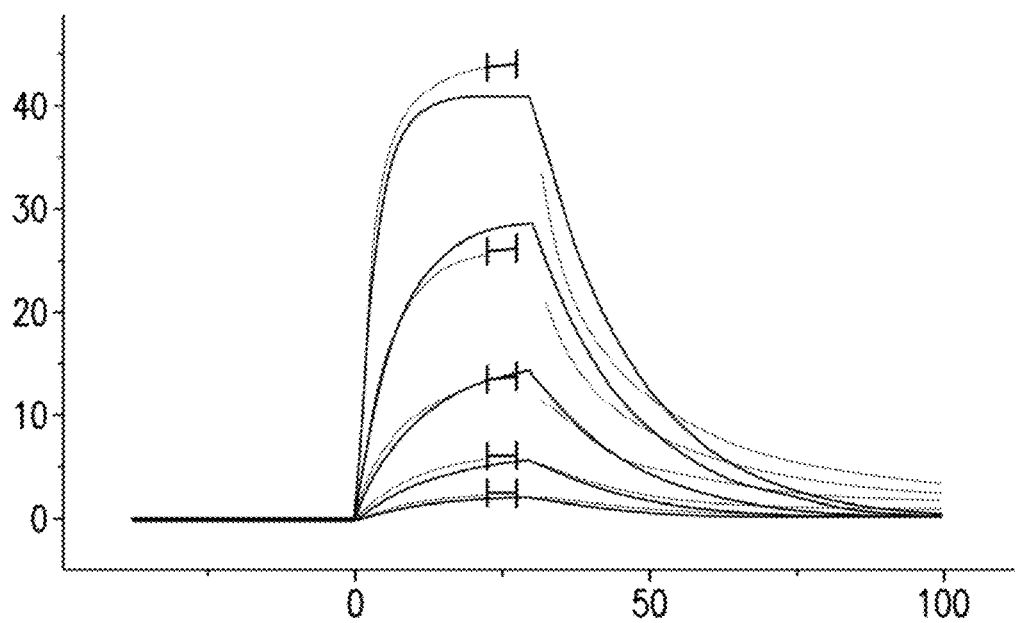
FIG. 6a-6f. PetML119/122 canine and murine FcRN binding.
a) Canine FcRN binding PetML119.
b) Murine FcRN binding PetML119.
c) Affinity table of canine and murine binding FcRN.
d) Canine FcRN binding PetML122.
e) Murine FcRN binding PetML122.
f) Affinity table of canine and murine FcRN binding.
Figure 6B:
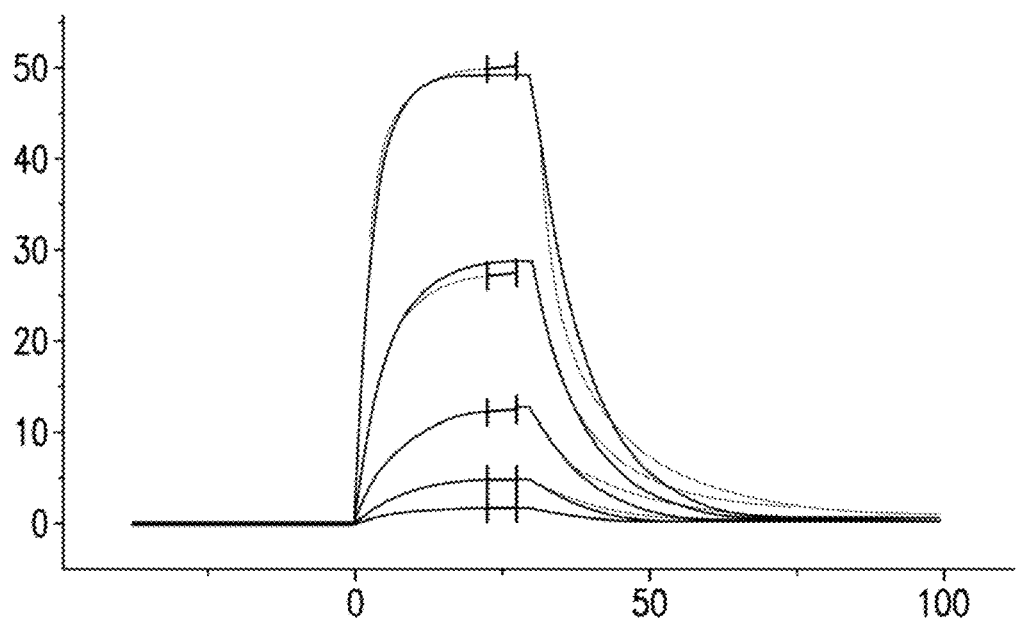
Figures 6C, 6D:
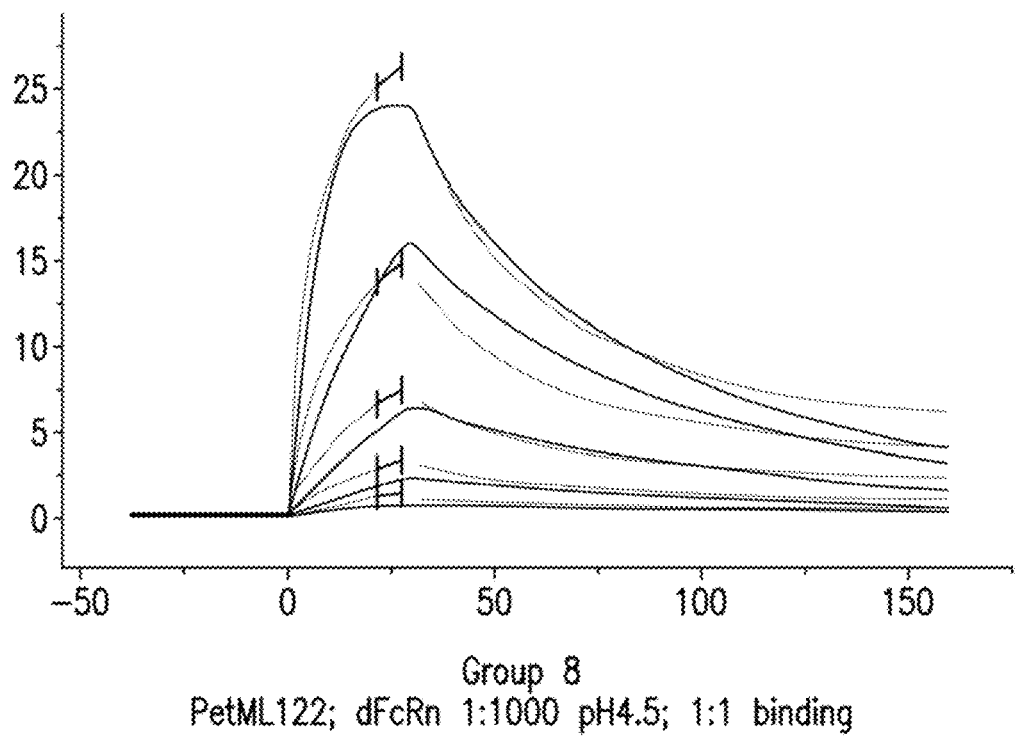
Figures 6E, 6F:
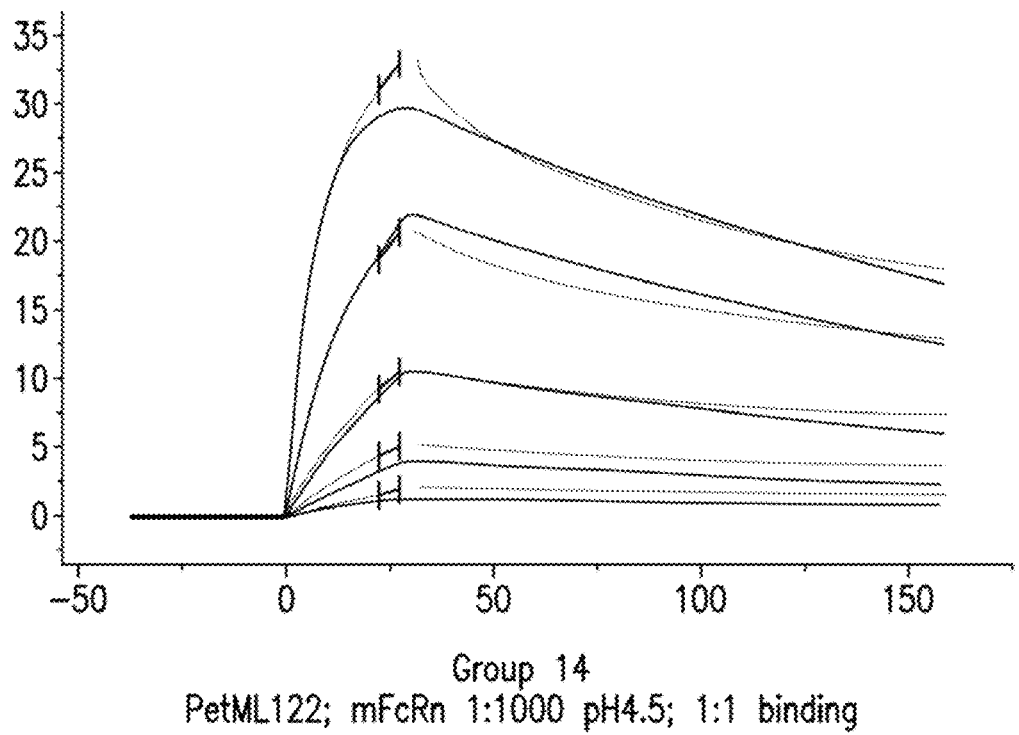

4. Stress Tests (FIG. 4)

Freeze and thaw test:

50 uL aliquots of PetML119 at 5 mg/mL in PBS were prepared and stored at either 4° C. (1 aliquot per molecule) or −80° C. (3 aliquots per molecules) in sealed PCR tubes. −80° C. aliquots were thawed at room temperature in 5 minutes and stored back at −80° C. leaving one aliquot out (1 freeze and thaw). This have been repeated two more times (2 and 3 freeze and thaw cycles) and then 10 uL of each sample (including 4° C. controls) were injected into H-SEC using same method as above. Percentage of monomeric species and Area (indicative of protein concentration) were determined for each molecule/freeze&thaw cycle and compared to a reference run (samples stored at 4° C.).

PetML119 showed good resistance to Freeze and Thaw, with only minor protein loss upon 3 cycles.

Thermal & Chemical stress:

50 uL aliquots of PetML119 at 5 mg/mL in PBS or PBS+100 mM DTT were prepared and incubated for 30' at different temperatures (25° C., 37° C., 60° C., 70° C. and 95° C.).

40 uL of each condition were diluted with 10 uL of NuPAGE™ LDS Sample Buffer (NP0007). 10 uL were loaded into NuPAGE™ 10%, Bis-Tris, 1.0 mm, Mini Protein Gel, 12-well (NP0302BOX) and run at 120V for 45'. Gel was stained with InstantBlue® Coomassie Protein Stain (ISB1L) (ab119211) for 10' and destained in ddH2O for an 1 hr. SDS-PAGE was then acquired using standard transilluminator equipment.

Results showed that PetML119 is very stable in both temperature and chemical stress, showing unfolding only when incubated at temperature higher than 70° C.

5. Protein A Binding Affinity Validation (FIG. 5)

Purified fusion proteins (PetML119 and PetML122) in PBS were concentrated using centrifugal concentrators (Sartorious-VS02H22) to 5 mg/mL Protein concentration was assessed using UV absorbance at 280 nm with NanoDrop™ One (Thermo Scientific™).

Binding affinity of fusion proteins to Protein A was assessed using Biacore 8K (Cytiva).

Briefly, Sensor Chip Protein A (Cytiva) was docked into Biacore 8K, equilibrated for 30' at RT and then Running Buffer (10 mM HEPES pH7.4 150 mM NaCl 3 mM EDTA and 0.005% Tween20) was applied to the SPR chip surface.

Fusion protein dilutions were prepared diluting PetML119/122 from 1 uM to 4 nM (6 concentrations with 1:3 dilutions) in Running Buffer and kinetics was assessed using single cycle kinetics method (Biacore Assay Handbook, Cytiva). Kinetics and/or Affinity quantification have been performed using Biacore Insight following standard analyses methods.

The results show that protein A binding for PetML122 is slightly affected by YTE mutation introduced, a faster dissociation is observed compared to PetML119. This results in lower yield post protein A purification although the quality of protein is comparable.

6. FcRn Binding Affinity Validation (FIG. 6)

Purified fusion proteins (PetML119 and PetML122) in PBS were concentrated using centrifugal concentrators (Sartorious-VS02H22) to 5 mg/mL Protein concentration was assessed using UV absorbance at 280 nm with NanoDrop™ One (Thermo Scientific™).

Binding affinity of fusion proteins to Fc Neonatal Receptor was assessed using Biacore 8K (Cytiva).

Briefly, CM5 Sensor Chip (Cytiva) was docked into Biacore 8K, equilibrated for 30' at RT and then Running Buffer (10 mM HEPES pH6 150 mM NaCl 3 mM EDTA and 0.005% Tween20) was applied to the SPR chip surface.

Canine and murine FcRn-B2M recombinant protein (Immunitrack, ITF12-ITF08) was diluted into 10 mM acetate buffer pH4.5 at 4 nM (1:2000 dilution from stock) and immobilised using standard amine coupling reaction.

Fusion protein dilutions were prepared from 3 uM to 37 nM (5 concentrations with 1:3 dilutions) in Running Buffer and kinetics was assessed using multi-cycle kinetics method (120 sec association-300 sec dissociation). Kinetics and/or Affinity quantification have been performed using Biacore Insight following standard analyses methods.

A 10-fold increase in binding affinity to FcRn has been seen for PetML122, confirming the triple mutant YTE had a positive effect on binding to both canine and murine neonatal receptor. In particular, an extended dissociation rate was observed.

Figure 7A:
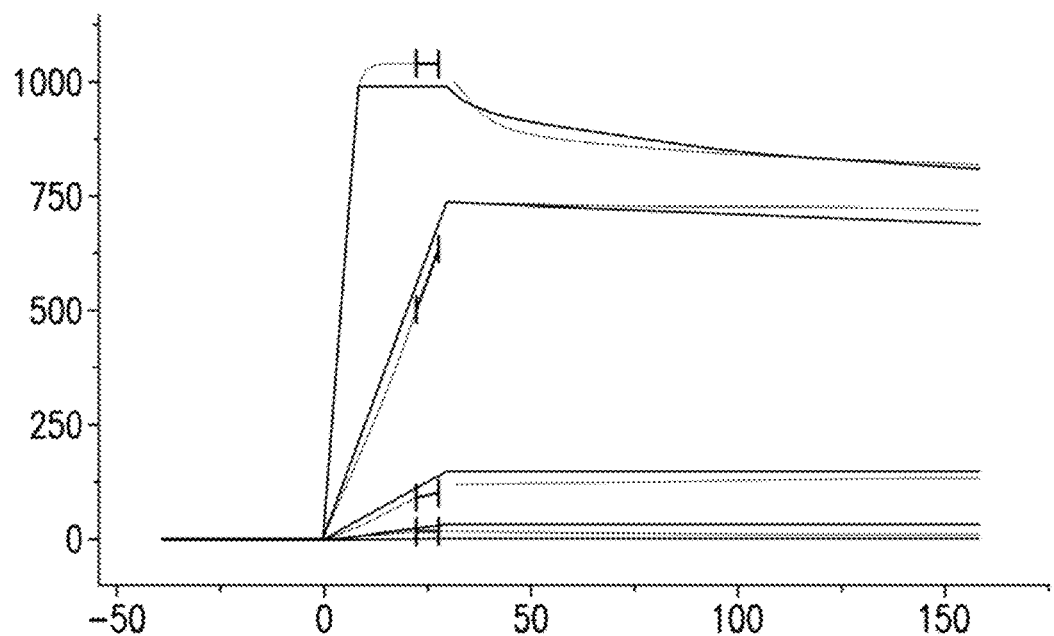
FIG. 7a-7e. NGF binding.
a) PetML119 binding to human p75.
b) PetML119 to rat NGF.
c) Kinetics affinity table.
d) Bedinvetmab binding to human NGF binding.
e) Kinetics affinity table.
Figure 7B:
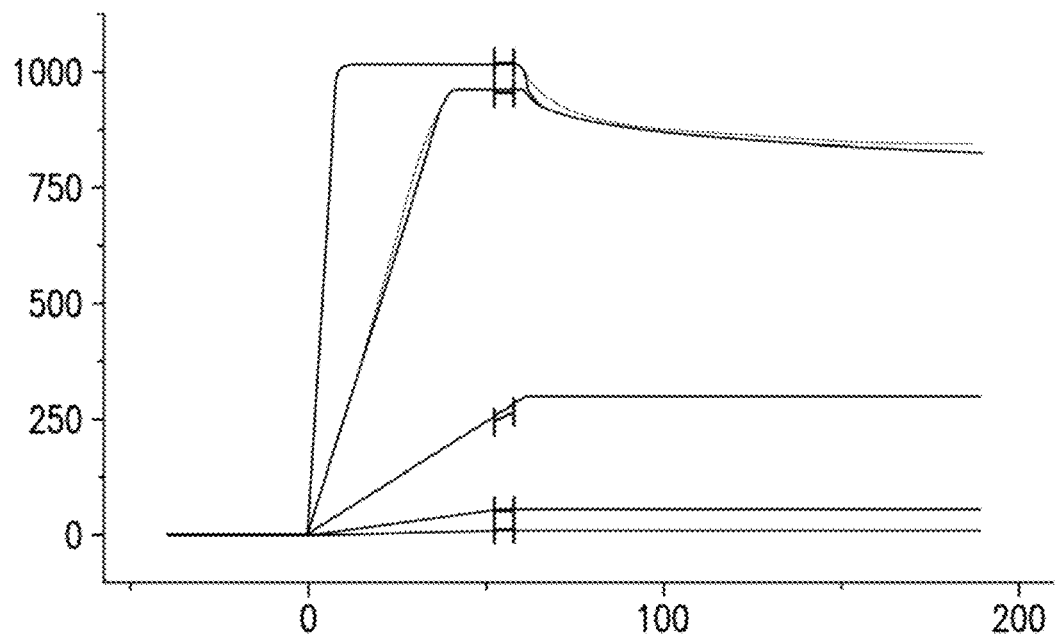
Figures 7C, 7D, 7E:
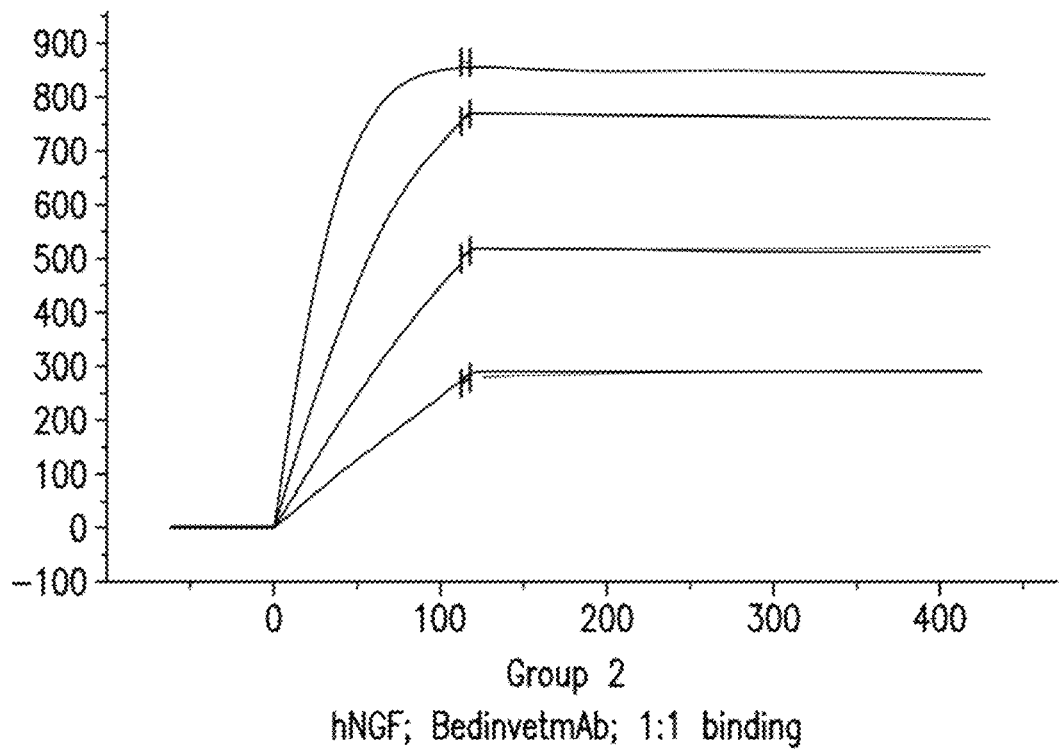

7. Human and Rat Nerve Growth Factor (h-rNGF) Binding Affinity Determination (FIG. 7)

Purified fusion protein (PetML119) in PBS was concentrated using centrifugal concentrators (Sartorious-VS02H22) to 5 mg/mL Protein concentration was assessed using UV absorbance at 280 nm with NanoDrop™ One (Thermo Scientific™).

Binding affinity of fusion proteins to human and rat NGF was assessed using Biacore 8K (Cytiva).

Briefly, Protein A Sensor Chip (Cytiva) was docked into Biacore 8K, equilibrated for 30' at RT and then Running Buffer (10 mM HEPES pH7.4 150 mM NaCl 3 mM EDTA and 0.005% Tween20) was applied to the SPR chip surface.

PetML119 was diluted into running buffer at 6 nM concentration. These have been immobilised using 90 sec association at 10 uL/min as capturing step, followed by injection of running buffer to remove any unbound product.

Human and rat NGF (from Bio-Techne Ltd-556-NG/CF/256-GF-100/CF) was diluted in Running Buffer at 100 nM with 1:2 further dilutions down to 4.68 nM. Kinetics were assessed using multi-cycle kinetics with capture step method (30 sec association-120 sec dissociation) followed by regeneration step (0.1M Glycine pH2.2 contact time 60 sec FR 30 uL/min). Kinetics quantification have been performed using Biacore Insight following standard analyses methods.

Results showed subnanomolar KD for both human and rat NGF with PetML119.

8. Intact Mass Analyses

Purified fusion proteins (PetML119 and PetML122) in PBS were concentrated using centrifugal concentrators (Sartorious-VS02H22) to 1 mg/mL Protein concentration was assessed using UV absorbance at 280 nm with NanoDrop™ One (Thermo Scientific™).

LC-MS analyses have been performed on BioAccord using BioResolve RP mAb Polyphenyl Column, 450 Å, 2.7 μm, 2.1×50 mm and ACQUITY UPLC® I-Class Plus from WATERS.

Briefly, 3 pmol (diluted in LC-MS grade H2O) of each fusion protein were injected in RP column and a eluate peaks were analysed by MS. Intact mass analyses showed presence of multiple species corresponding to different degree of glycosylation, consistently on what observed by H-SCX.

The intact molecule appears to be a mixture of species. The observed mass is 96158-97836 Da. The mass of the base species (96158 Da) is consistent with a dimer of Fc fusion aa 20-241+4 glycans which is consistent with the total number of glycosylation sites expected in the molecule. Additional species are consistent with additional decoration of the glycans.

9. Unfolding and Oligomerisation Determination (FIG. 4)

Purified fusion proteins (PetML119) in PBS were concentrated using centrifugal concentrators (Sartorious-VS02H22) to 3 mg/mL Protein concentration was assessed using UV absorbance at 280 nm with NanoDrop™ One (Thermo Scientific™).

Tm and Tagg analyses have been performed on UnCle from Unchained labs using standard protocol.

Briefly, 10 uL of fusion protein have been used to determine unfolding and aggregation events during a temperature ramp (from 25° C. till 95° C.). As anticipated from previous results, PetML119 showed no aggregation up to 95° C. with Tm1 around 67° C.

Figure 8A:
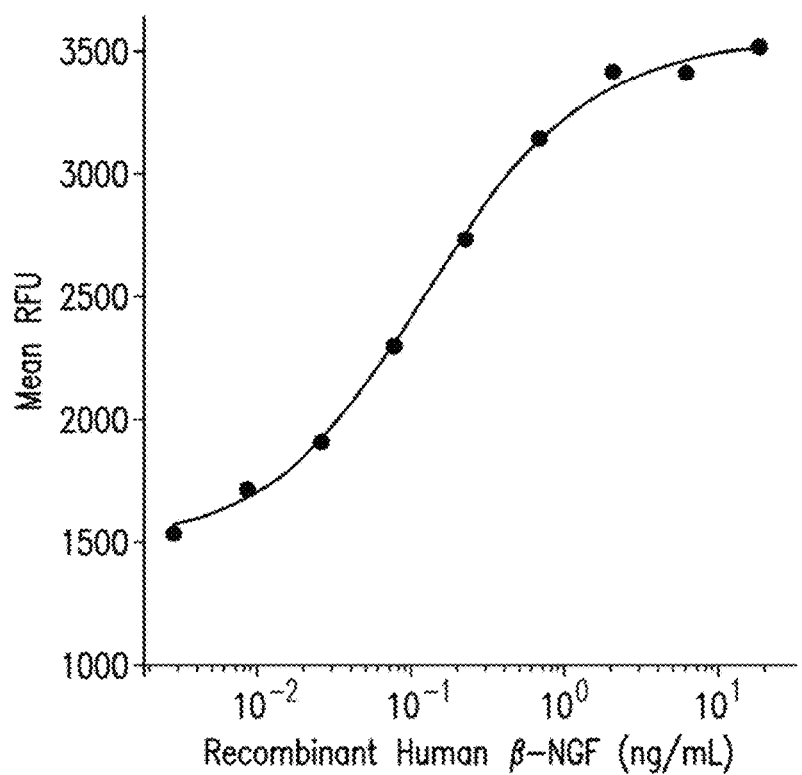
FIG. 8a-8c. TF-1 cell proliferation assay. TF-1 labelled with CFSE-cell trace at 2.5 uM 30' RT. TF-1 seeded at 104 cells/well in 96 well plate. Positive ctr: TF-1 cells in RPMI media+10% FBS+10 ng/mL hNGF3 timepoints (t 2 hrs, t 4 d and t 7 d).
a) Activity of NGF: 2 ng/mL EC50.
b) TF-1 cell proliferation assay read out.
c) TF-1 cell proliferation assay read out using PetML119, PetML122 and Bedinvetmab.
Figure 8B:
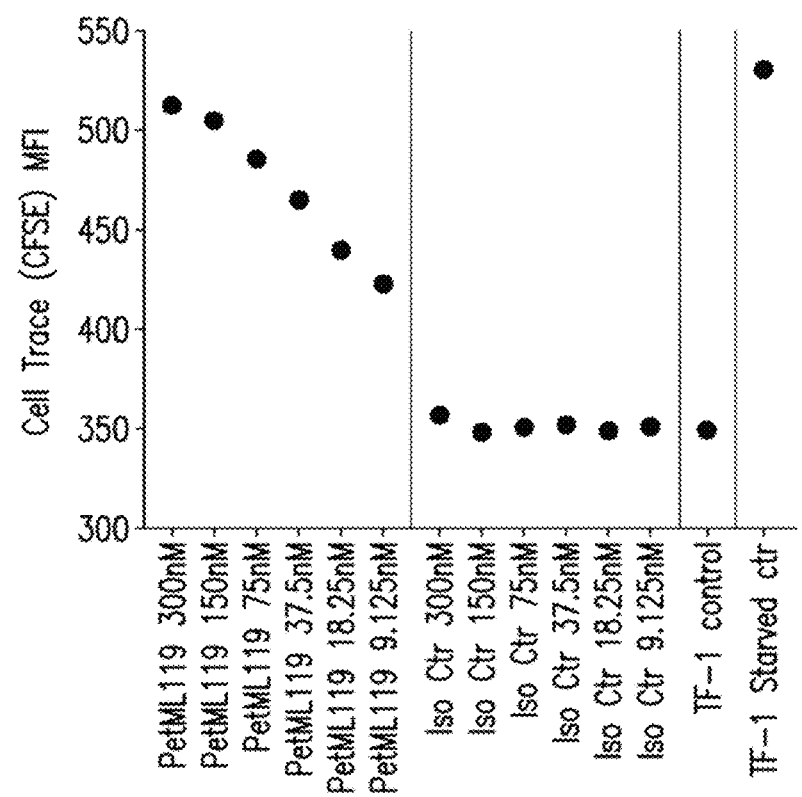
Figure 8C:
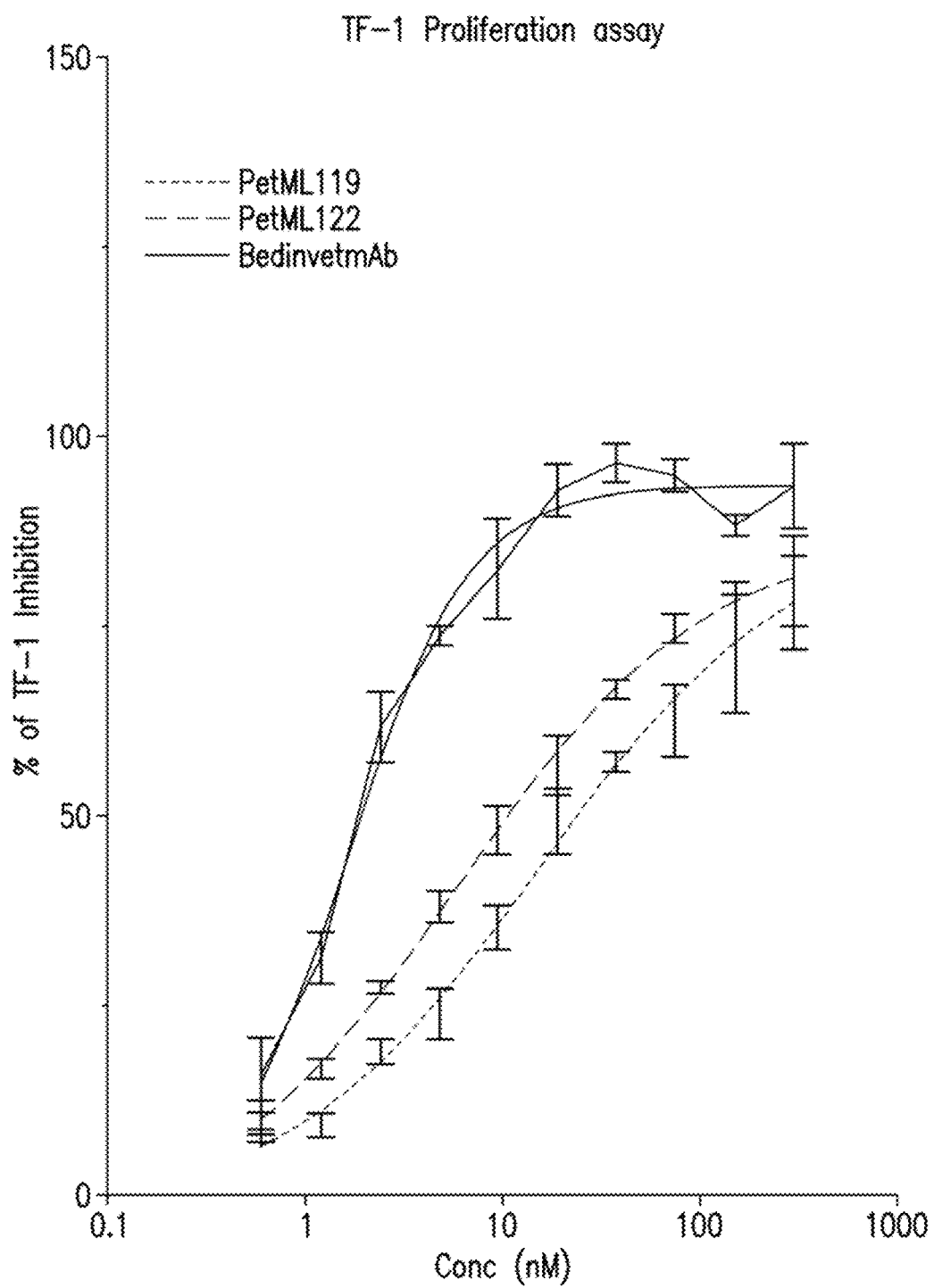

10. In Vitro NGF Inhibition Assay (FIG. 8)

To assess biological activity of our p75 fusion protein, we used an NGF-dependent (cell line TF-1 cell line). The cells are completely dependent on interleukin 3 (IL-3) or granulocyte-macrophage colony-stimulating factor (GM-CSF) for long term growth. The cells do not respond to interleukin 5 (IL-5). TF-1 cells respond to a variety of other lymphokines and cytokines such as interleukin 1 (IL-1), interleukin 4 (IL-4), interleukin 6 (IL-6), interleukin 9 (IL-9), Interleukin 11 (IL-11), interleukin 13 (IL-13), stem cell factor (SCF), leukemia inhibitory factor (LIF) and nerve growth factor (NGF).

Proficient sequestration of NGF by our fusion protein will result in slower proliferation in comparison to control.

TF-1 cell line was bought from ATCC (CRL-2003) and kept in culture using standard aseptic methods using complete RPMI (10% FBS+2 mM I-Gln+10 ng/mL hNGF).

2 million TF-1 cells were labelled with 2.5 uM CFSE cell trace (Invitrogen-C34554) in 1 mL of RPMI only for 30' at RT in the dark. Cells have been then washed 2× in complete RPMI media, counted again and seeded at 10000 cells/mL (1 mL total volume per well) in 24-well plate.

Dilution of PetML119/122 or controls (Bedinvetmab-anti-NGF IgG control, unrelated fusion protein and RPMI without NGF as negative control WHO Drug Information, Vol. 32, No. 4, 2018-pg568) were diluted in 100 uL of RPMI media from 3 uM concentration till 91.25 nM. 100 uL of protein dilution was added to each well. Briefly, published Bedinvetmab aa sequence for both heavy chain and light chain have been used to generate codon optimised (for CHO expression) cDNA. Both HC and LC cDNA have been cloned in frame with standard peggy-bac plasmid. CHO have been then stably transfected as above.

Plates were analysed after 3 days. Briefly, 1 mL cell suspension were centrifuged 5' at 300 g RT, washed 2 times with FACS buffer (PBS+3% FBS+3 mM EDTA) and finally resuspended in 100 uL of FACS buffer. Cells were acquired using CytoFLEX Flow Cytometer using following parameters (FSC:20; SSC:50; FITC:1; threshold: 1313131). Cells were gated based on FITC fluorescence (more fluorescence less proliferation) and % of proliferation inhibition was calculated considering 100% inhibition TF-1 cells cultured in RPMI without NGF and 0% inhibition cells cultured with complete RPMI media. Graph pad was used to calculate IC50 values.

Both PetML119/122 and Bedinvetmab were able to inhibit TF-1 proliferation in a dose dependent manner.

|  | PetML119 | PetML122 | BedinvetmAb |
|---|---|---|---|
| IC50 (nM) | 15.25 | 5.91 | 1.645 |

11. MIA-Induced OA in Rats (Efficacy and pK)—FIGS. 9 to 12)

Figure 9:
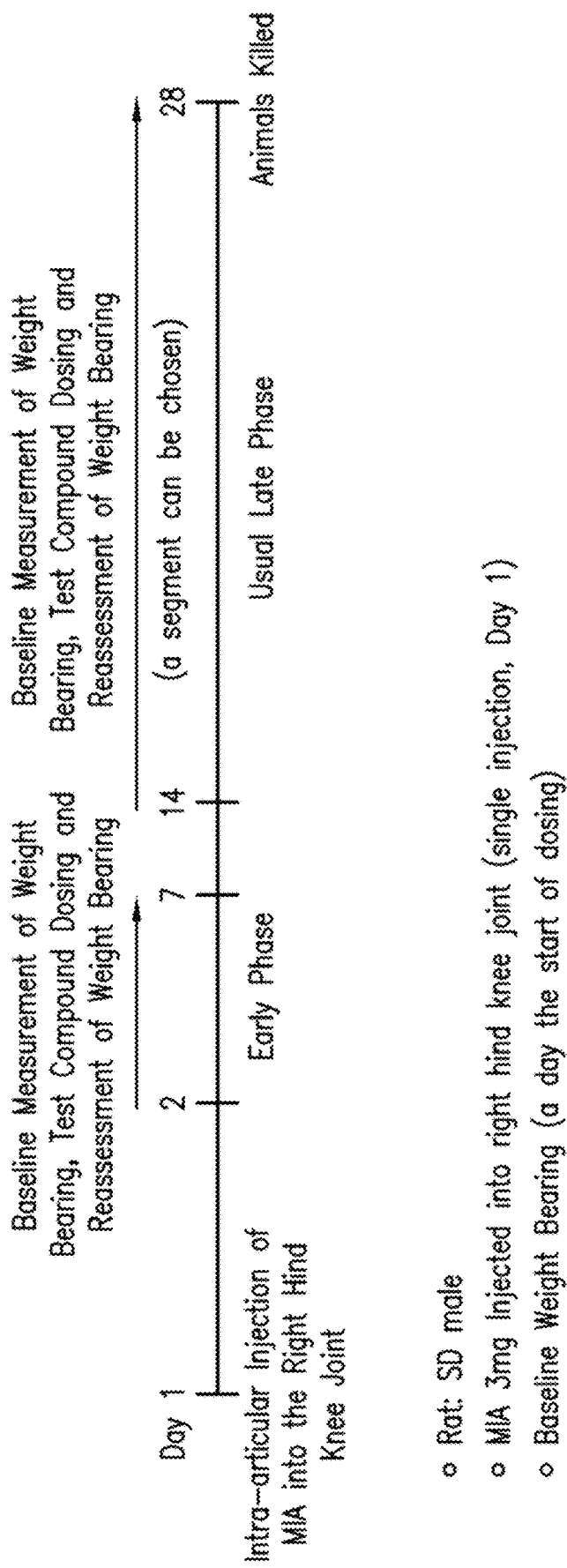
FIG. 9. In vivo model.
Figure 10A:
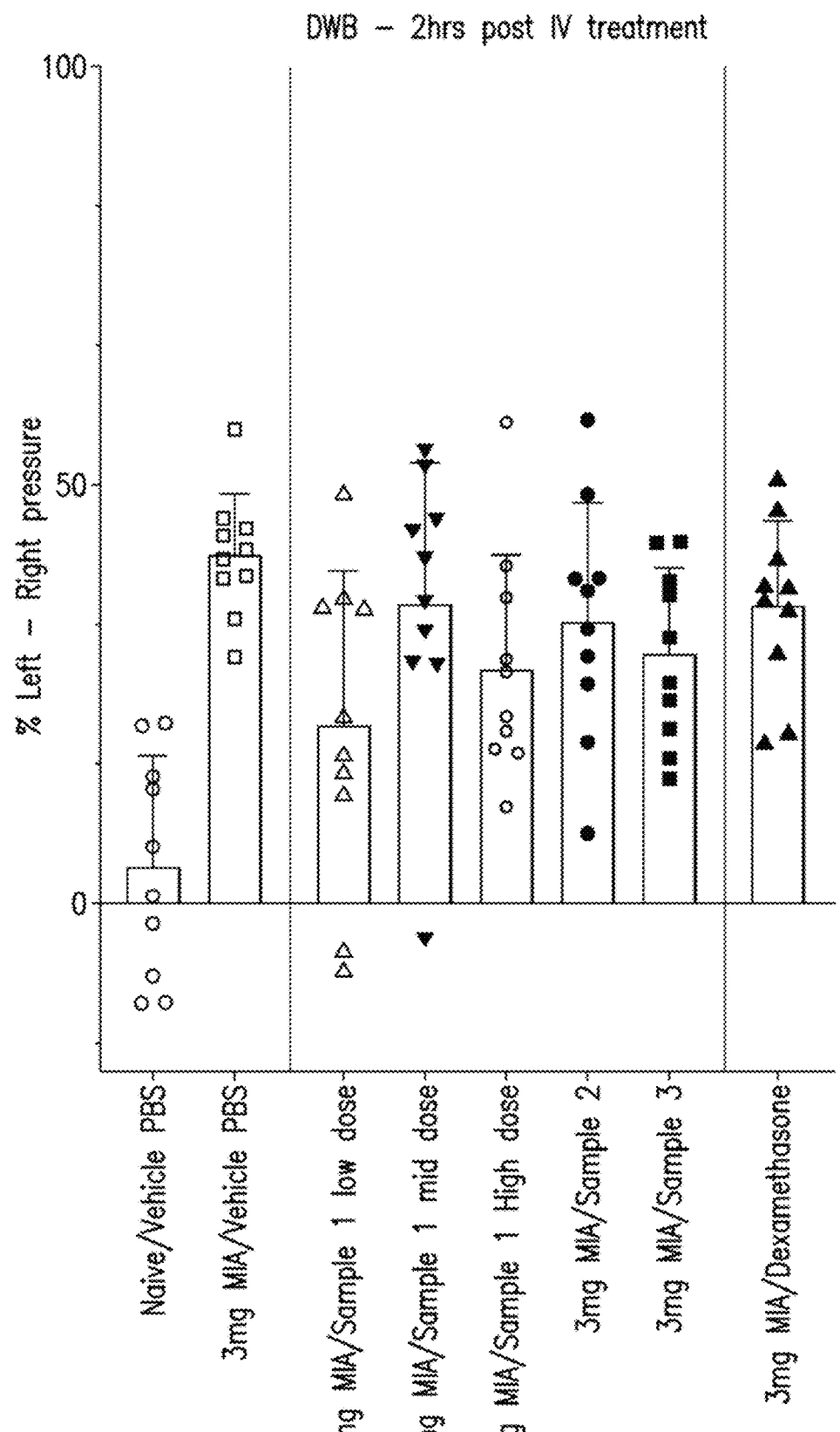
FIG. 10a-10d. Analgesic effects in vivo.
a) 2 hours post IV treatment.
b) 3 days post IV treatment.
c) 11 days post IV treatment.
d) 18 days post IV treatment.
Figure 10B:
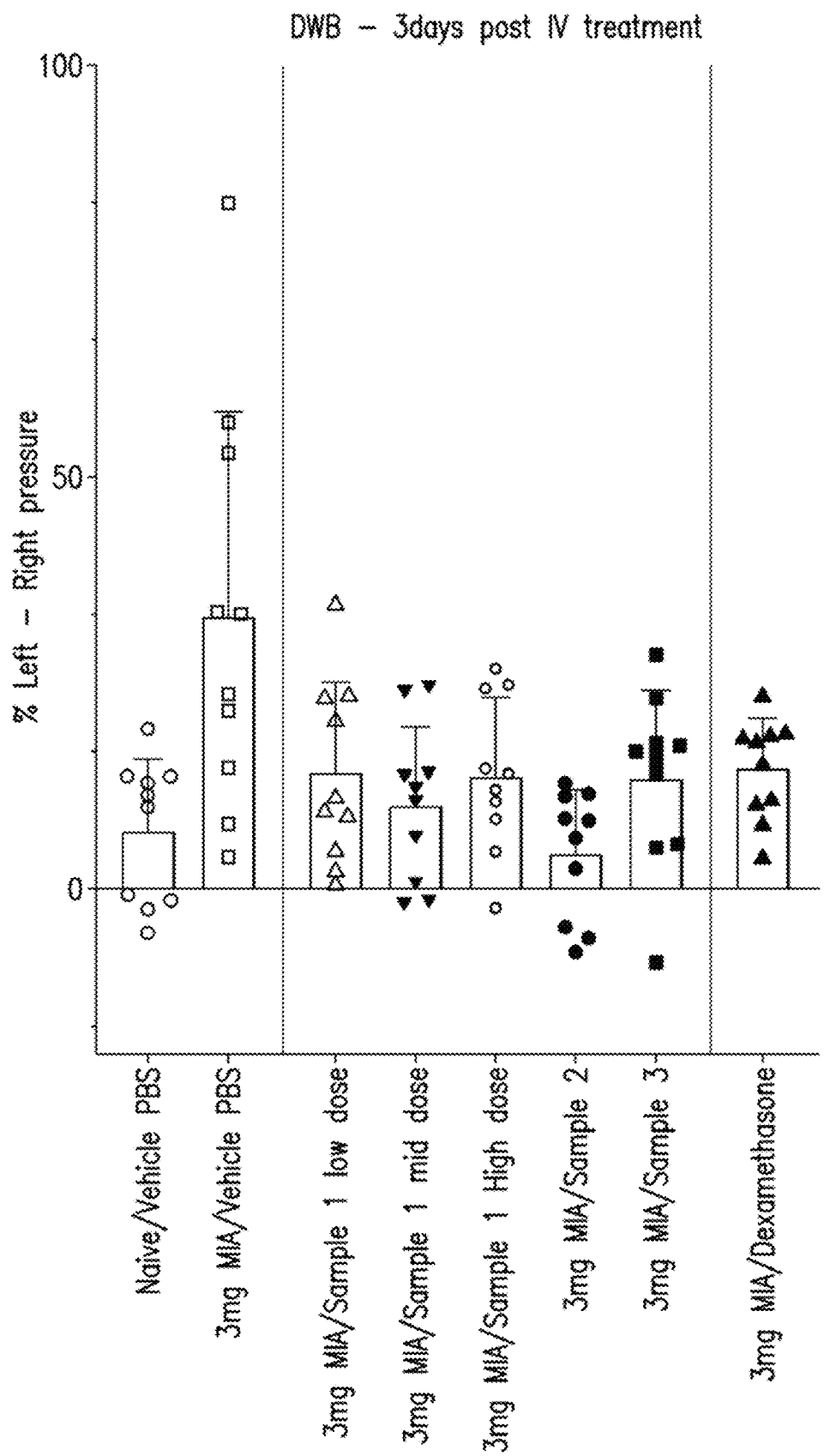
Figure 10C:
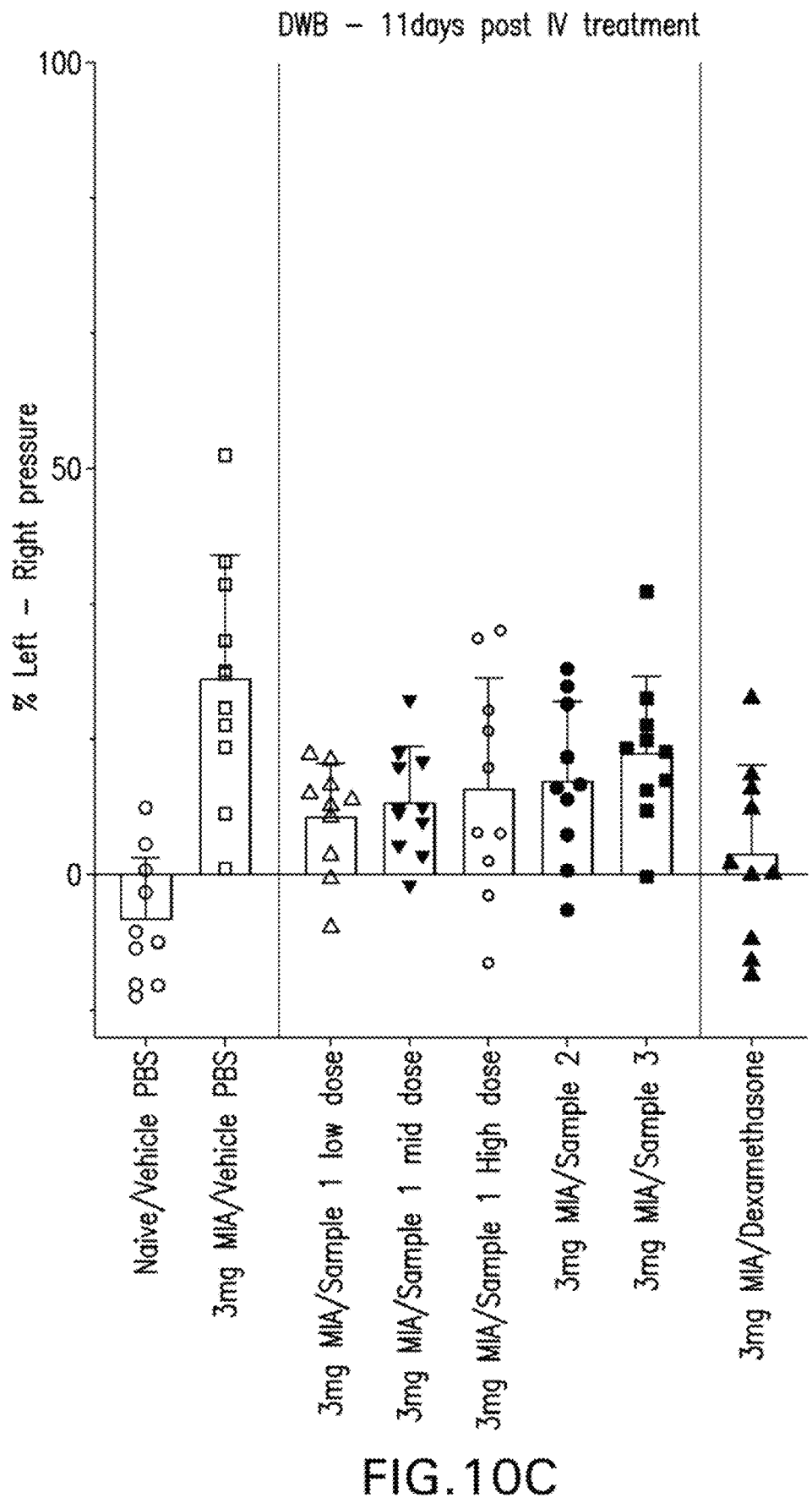
Figure 10D:
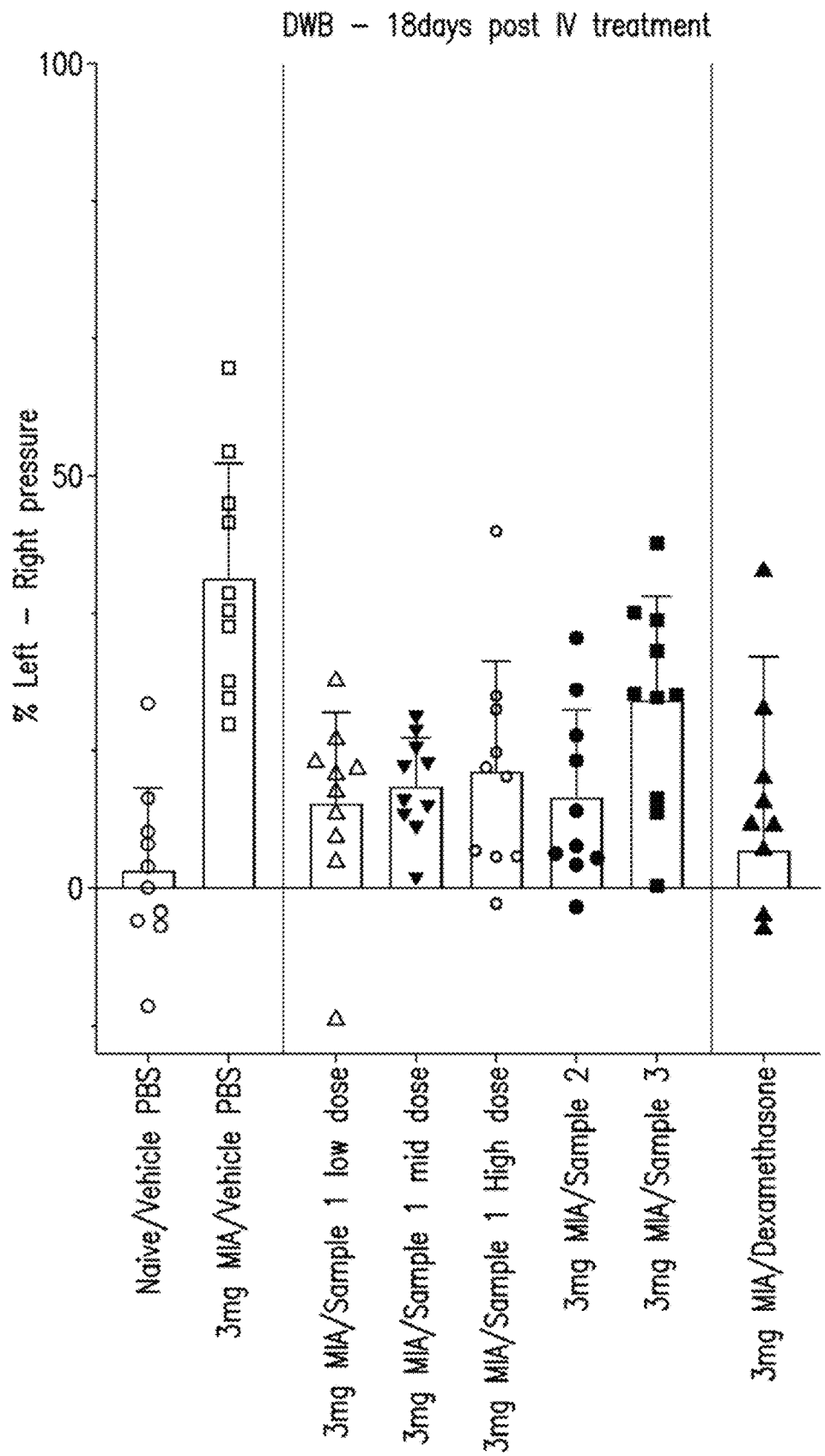
Figure 11A:
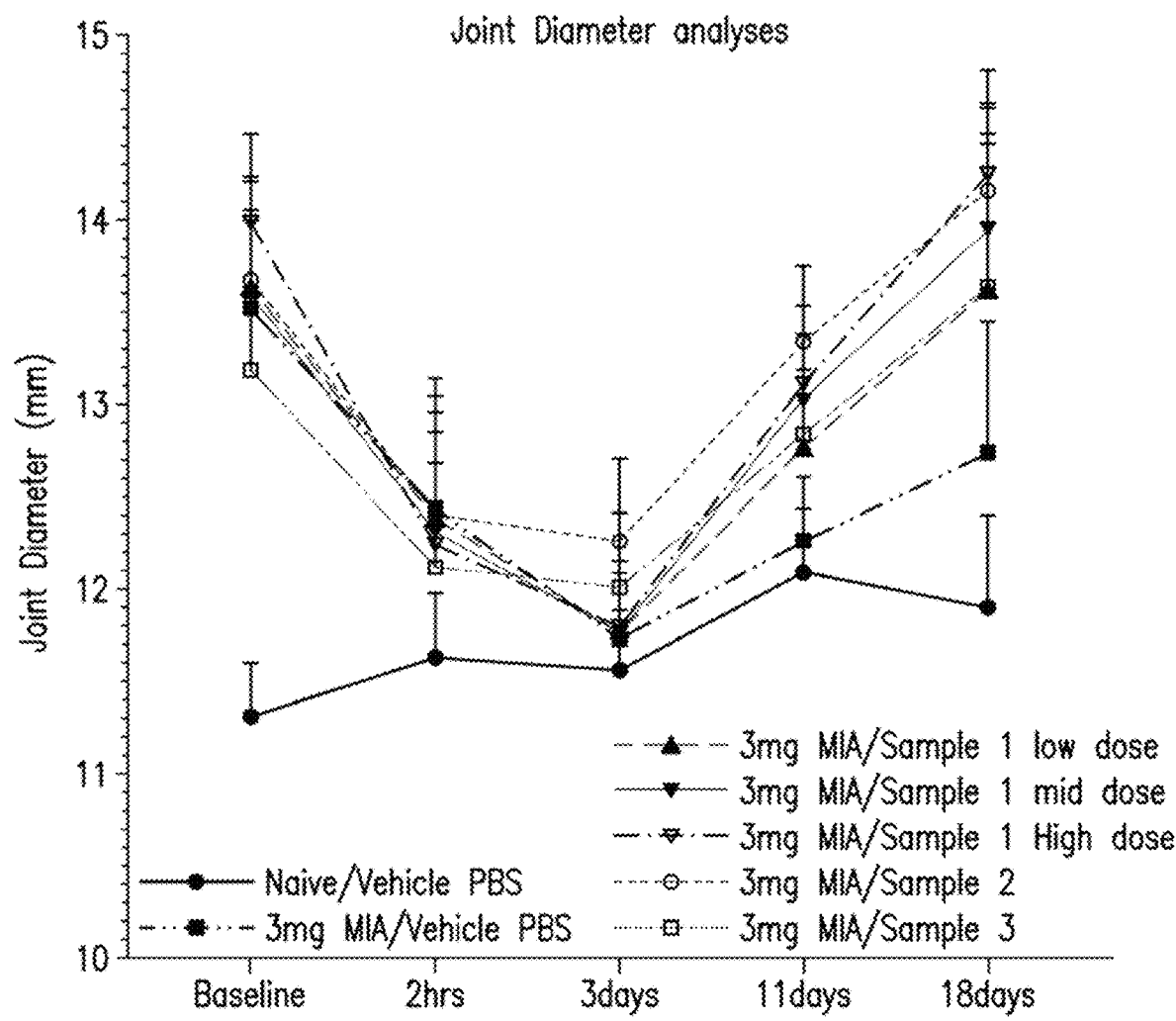
FIG. 11a-11b. Joint Diametre and body weight
a) Joint Diametre analysis.
b) body weight analysis.
Figure 11B:
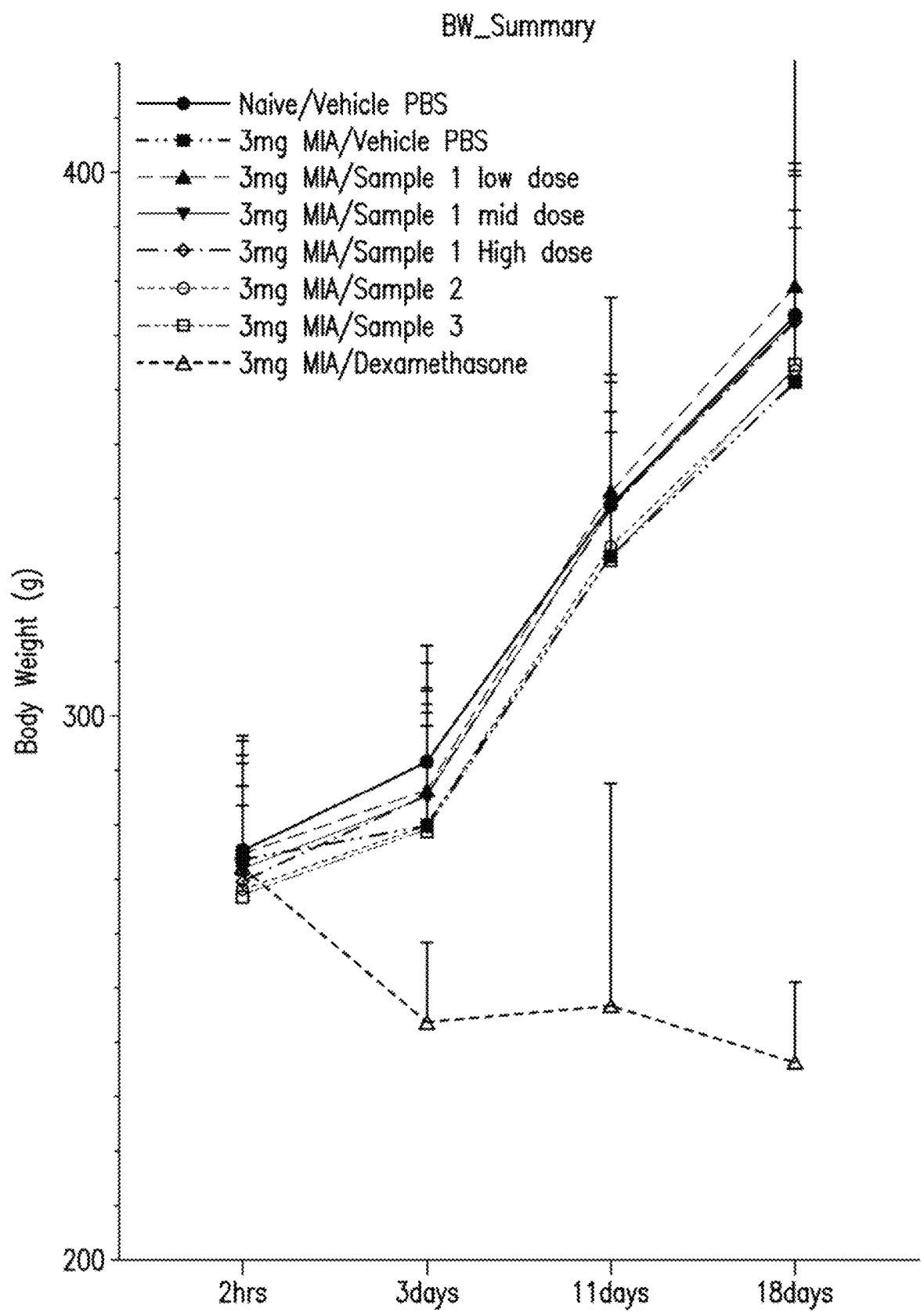
Figure 12A:
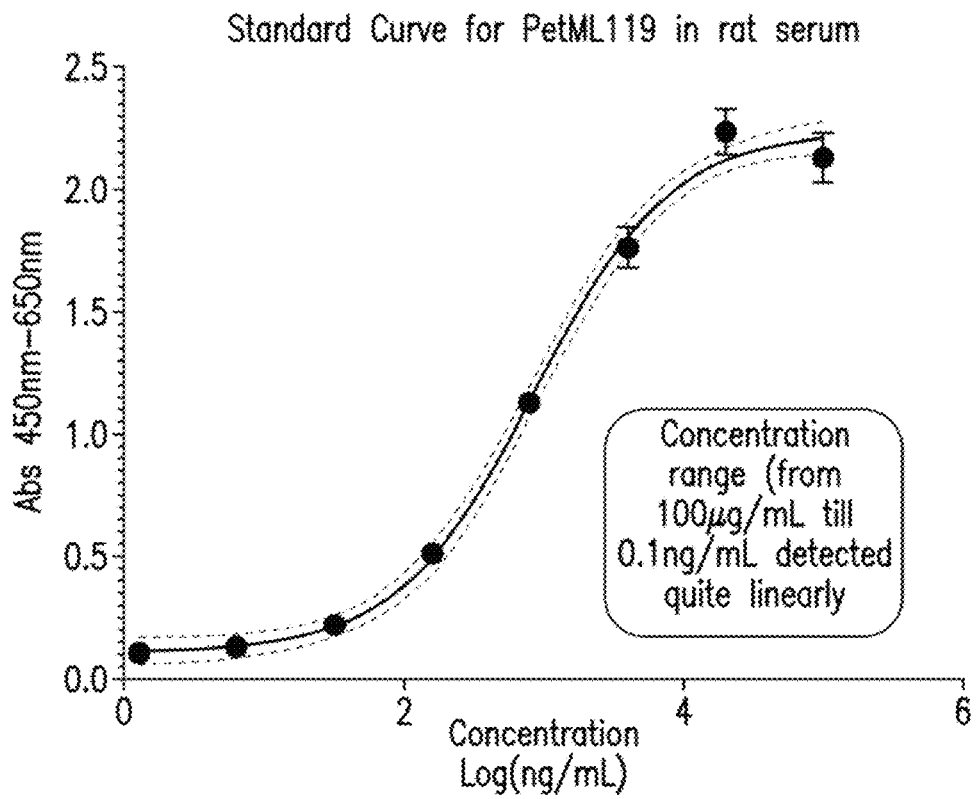
FIG. 12a-12f. pk analysis-half life.
a) Standard curve for PetMI119 in rat serum.
b) Standard curve for PetMI122 in rat serum.
c-f) Rat study pK results. Calculated half-life for PetML119 at different concentration is between 56-70 hrs.
Figure 12B:
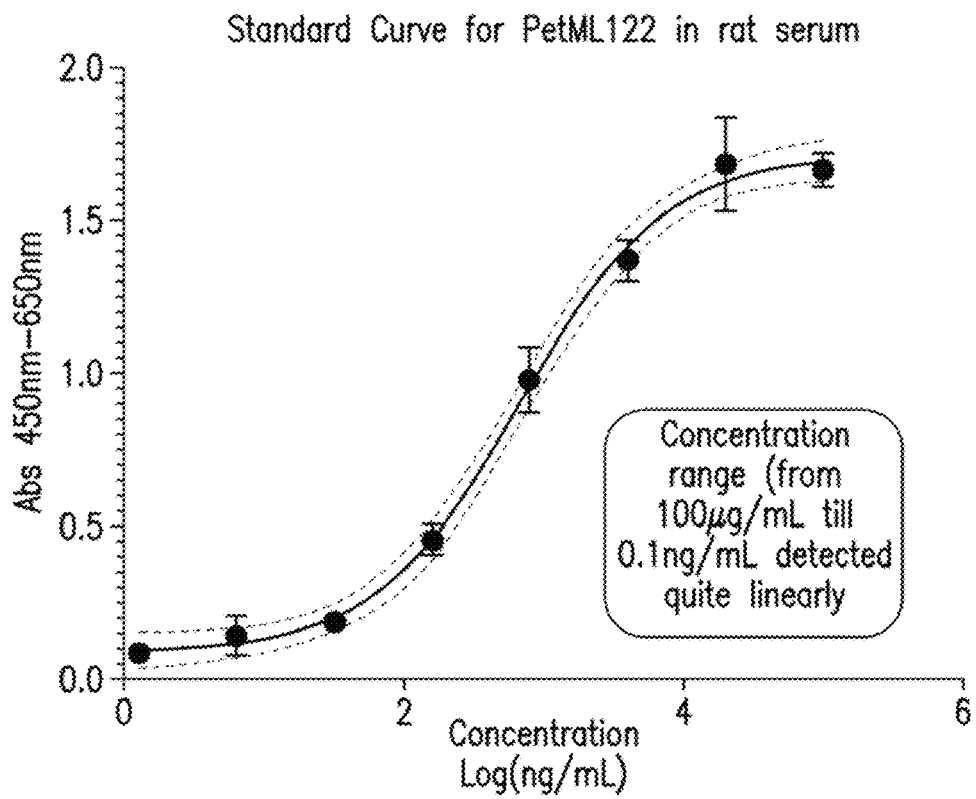
Figures 12C, 12D:
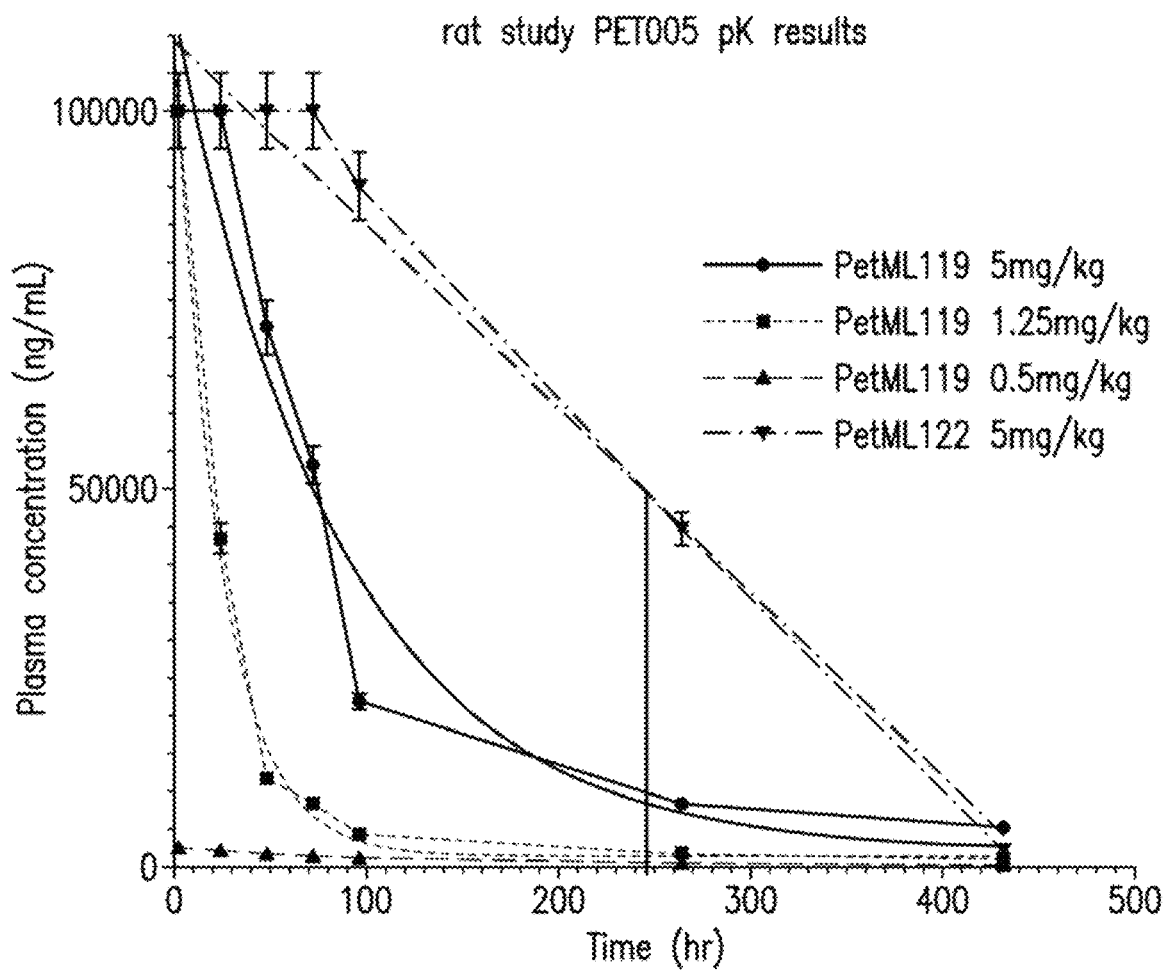
Figures 12E, 12F:
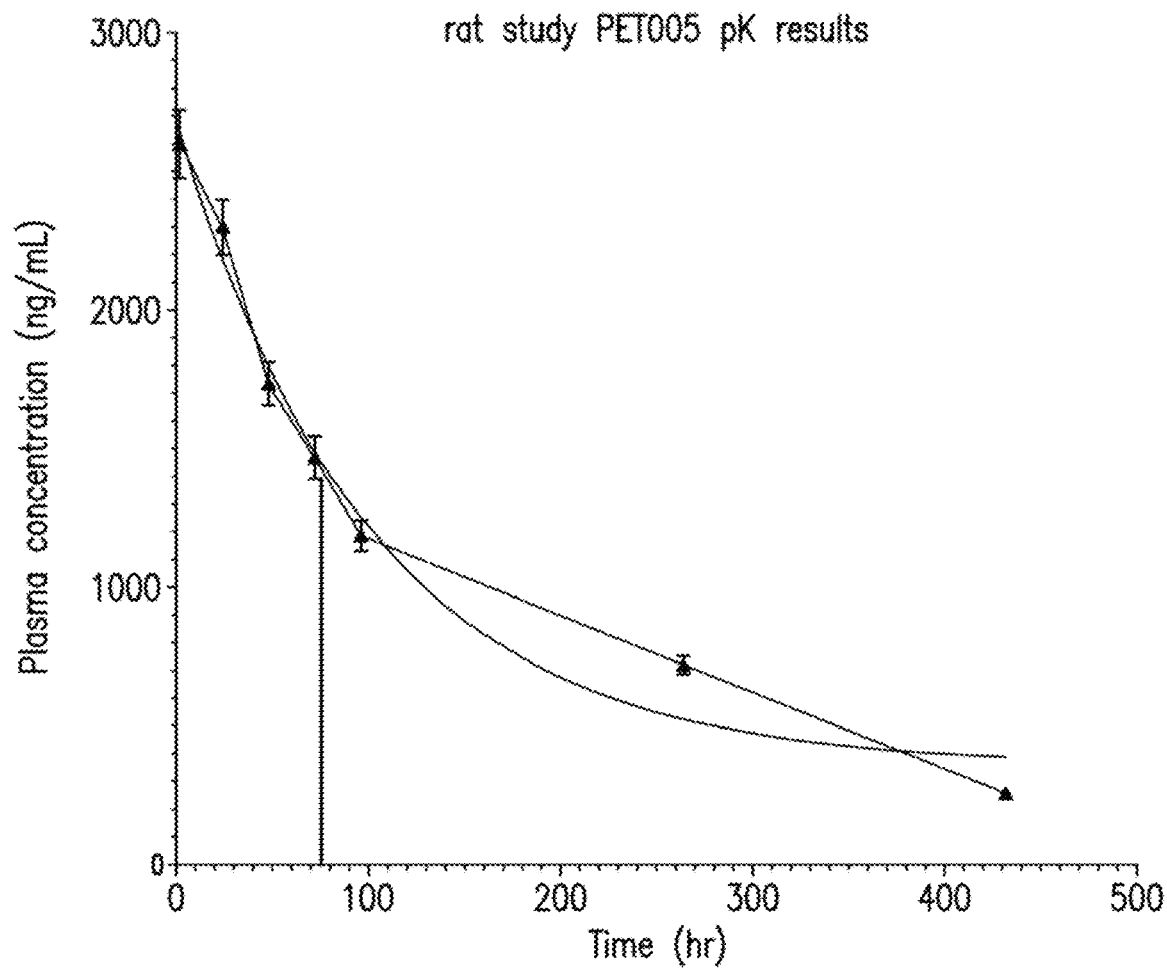

Efficacy and half-life for PetML119/122 were analysed using a rat model of OA. The detailed protocol is shown below. The model is shown in FIG. 9.

Induction of Arthritis

Osteoarthritis was induced chemically by an intra-articular (I.A.) injection of 3 mg of monosodium-iodoacetate (MIA) (in 25 μL saline) into the right hind limb knee joint of the rat given under isoflurane anesthesia. While under anesthesia, ophthalmic ointment was applied to both eyes. The day of I.A. injection of MIA was counted as Day 0.

Allocation to Treatment Groups

Baseline dynamic weight bearing (DWB) were measured for all rats. Body weight (BW) was also measured at the same time. Rats were anesthetized and MIA injected into the right Knee joint through the middle of the patellar tendon approximately perpendicular to the tibia (Intra-articular (I.A.)). Dose level for I.A. injection of MIA was selected based on previous literature report in rodents (Bove et al.: Weight bearing as a measure of disease progression and efficacy of anti-inflammatory compounds in a model of monosodium iodoacetate-induced osteoarthritis. Osteoarthritis Cartilage. 2003 November; 11(11):821-830). Animals showing a significant weight bearing difference between the MIA injected limb (right) and the healthy limb (left) were assigned to the study. Randomization was done based on both baseline DWB and BW (two variables randomization).

Dynamic Weight Bearing (DWB) Evaluation

Dynamic Weight Bearing was evaluated using the BioSeb® automated DWB system according to the manufacturer's manual. A two-minute recording was done for each rat. Analysis of dynamic weight bearing data was done off-line using the BioSeb® software. The system automatically calculated the weight borne by each limb and the tail. Body weight was measured for each rat immediately before the DWB for each time of testing. DWB measurement was done at different time points as per schedule in Study Design. Total distance travelled was also noted during DWB data analysis.

Dosing with Test Items

Group 1-2 rats received intravenous (IV) injections of vehicle and Group 3-7 rats received IV injections with the test items at designated doses once on Day 3 as depicted in the table below. Group 8 rats received oral gavage dosing with dexamethasone once daily from Day 3-21 as depicted in the table below.

Monosodium-Lodoacetate (MIA)-Induced OA Rat Study with PETML119/122

Study Design

| *Gr. | Group Treatment | TI Dose level | TI Route, Volume | TI Dosing schedule | DWB testing | N |
|---|---|---|---|---|---|---|
| 1 | Naive/ Vehicle PBS | 0 | IV, 5 mL/kg | Day 3, QD | Day 1 (baseline), Days 3, 6, 14, 21 | 10 |
| 2 | 3 mg MIA/ Vehicle PBS | 0 | IV, 5 mL/kg | Day 3, QD | Day 1 (baseline), Days 3, 6, 14, 21 | 10 |
| 3 | 3 mg MIA/ Sample 1, low dose | 0.5 mg/kg | IV, 5 mL/kg | Day 3, QD | Day 1 (baseline), Days 3, 6, 14, 21 | 10 |
| 4 | 3 mg MIA/ Sample 1, mid dose | 1.5 mg/kg | IV, 5 mL/kg | Day 3, QD | Day 1 (baseline), Days 3, 6, 14, 21 | 10 |
| 5 | 3 mg MIA/ Sample 1, high dose | 5 mg/kg | IV, 5 mL/kg | Day 3, QD | Day 1 (baseline), Days 3, 6, 14, 21 | 10 |
| 6 | 3 mg MIA/ Sample 2 | 5 mg/kg | IV, 5 mL/kg | Day 3, QD | Day 1 (baseline), Days 3, 6, 14, 21 | 10 |
| 7 | 3 mg MIA/ Sample 3 | 5 mg/kg | IV, 5 mL/kg | Day 3, QD | Day 1 (baseline), Days 3, 6, 14, 21 | 10 |
| 8 | 3 mg MIA/ Dexamethasone | 1 mg/kg from Day 1-7 and 0.3 mg/kg from Day 8-21 | PO, 10 ml/kg | Days 3-21 QD | Day 1 (baseline), Days 3, 6, 14, 21 | 10 |

*Animals from Groups 2 to 8 plus spares receive a single intra-articular (IA) injection with MIA (3 mg/25 µL saline) and the day of MIA injection is considered as Day 0 (in the right knee joint).
IV: Intravenous (tail vein); PO: oral gavage; QD-once daily Treated animals were observed for any clinical signs during the study. DWB was analysed on Days 3, 6, 14 and 21. Joint diameter was measured using a caliper on the right knee joint (medio-laterally) on days 3, 6, 14 and 21.

Briefly, both PetML119 (at different doses) and 122 (single dose) showed good analgesic effect outcompeting anti-NGF benchmark (Bedinvetmab) (FIG. 10). They also showed a similar activity to daily administration of dexamethasone while not showing side effects of NSAIDs (body weight loss—FIG. 11).

PK bleeds from 5 rats per group were taken using standard procedures on alternative days.

Serum Pk Analysis (FIG. 12)

Sandwich ELISA to quantify serum levels of our fusion protein were set up as follows:

30 uL of 2 ug/mL of Capturing antibody (Mouse anti-canine p75 Ab-->MAB367-SP (Novus Bio)) diluted in PBS+0.1M sodium bicarbonate were immobilised on half-area ELISA plates (MICROPLATE, 96 WELL, PS, HALF AREA, CLEAR, Item No.: 675061) overnight at 4° C.

Plates were washed 2× with 200 uL blocking solution (PBS+5% DNFM+0.2% Tween20) and blocking have been performed with 150 uL of blocking solution across all wells for 3 hrs at RT.

Sera from different timepoints/groups of rat study were diluted 100× in blocking solution (2 uL serum+198 uL blocking solution) and 30 uL were added to relevant wells. Standards from PetML119/122 were prepared diluting fusion protein into rat serum from 100 ug/mL till 1 ng/mL with 1:5 dilutions. Standards were then diluted 100× in blocking solution and 30 uL have been added to relevant wells.

Sera were incubated for 1 hr at RT with 450 rpm shaking.

Plates were washed 2× with 200 uL blocking solution; detection antibody (SA5-10309 (ThermoFisher)) have been diluted 1:40000 in blocking solution and 30 uL were added to each well and left 30' at RT with 450 rpm shaking.

Plates were washed 2× with 200 uL blocking solution; developing HRP-conjugated antibody (A16035 (ThermoFisher)) were diluted 1:10000 in blocking solution and 30 uL were added to each well and left 30' at RT with 450 rpm shaking.

Plates were washed 2× with 200 uL blocking solution then 2× with 200 uL of PBS+0.2% Tween20 and finally 50 uL of TMB (TMB Chromogen Solution (for ELISA)--> 002023) were added to each well. After 10', when standard curve showed saturation in first two points, the reaction was stopped adding 50 uL of 1M Sulphuric acid.

All wells were read with CLARIOstar Plus (BMG LABTECH) using endpoint Absorbance at 650 nm and 450 nm. Values were imported in Graph Pad and one-phase decay fitting have been applied to estimate half-life of these.

PetML119, from different doses, showed similar half-life (around 70 hrs) while PetML122 showed an extended half-life (around 10.5 days), see FIG. 12.

| Sequences |
|---|

SEQ ID NO: 1 canine p75NTR protein
<u>KEACPTGLYTHSGECCKACNLGEGVAQPCGANQTVCEPCLDSVTFSDVVSATEPCKPCTECVGLQS
MSAPCVEADDAVCRCAYGYYQDETTGRCEACRVCEAGSGLVFSCQDRQNTVCEECPDGTYSDEA
NHVDPCLPCTVCEDTERQLRECTRWADAECEEIPGRWITRSTPSEDSDSTAPSTEEPELPPDQEIIAS</u>
TMADVVTTVMGSSQPVVTRGTADNLIPVYCSILAAVWVGLVAYIAFKRWNSCKQNKQGANSRPVNQT
PPPEGEKLHSDSGISVDSQSLHDQQPHTQTAAGQALKGDGGLYSSLPPAKREEVEKLLNGSAGDTW
RHLAGELGYQPEHIDSFTHEACPARALLASWAAQDSATLDALLAALRRIQRADIVESLCSESTATSPV
ECD is underlined SEQ ID NO: 2 canine p75NTR nucleic acid sequence
<u>ATGGACGGGCCGCGCCTGCTGCTGCTGCTGCTGCTCCTGGGGGTGTCCCTTGGAGGTGCC</u>
AAGGAGGCATGTCCCACTGGCCTGTACACCCACAGCGGCGAGTGCTGCAAAGCCTGCAATCTG
GGTGAGGGGGTGGCCCAGCCTTGCGGAGCCAACCAGACCGTGTGTGAGCCCTGCCTGGACAG
CGTGACCTTCTCGGACGTGGTGAGCGCCACCGAGCCGTGCAAGCCGTGCACCGAGTGCGTGG
GGCTGCAGAGCATGTCGGCGCCGTGCGTGGAGGCGGACGACGCCGTGTGCCGCTGCGCCTAC
GGCTACTACCAGGACGAGACGACGGGCCGCTGCGAGGCGTGCCGCGTGTGCGAGGCGGGCTC
GGGGCTCGTGTTCTCGTGCCAGGACAGGCAGAACACCGTGTGCGAGGAGTGTCCCGACGGCAC
GTACTCCGACGAGGCCAACCACGTGGACCCGTGCCTGCCCTGCACCGTGTGCGAGGACACCGA
GCGCCAGCTGCGCGAGTGCACGCGCTGGGCCGACGCCGAGTGCGAGGAGATCCCTGGCCGTT
GGATTACCCGGTCCACACCCTCAGAGGACTCGGACAGCACGGCACCGCCCCCAGCACAGAGGAGCCAG
AGCTACCTCCAGATCAAGAAATCATAGCCAGCACCATGGCAGATGTGGTGACCACAGTGATGGG
CAGCTCTCAGCCTGTAGTGACCCGAGGAACCGCTGACAACCTCATCCCTGTCTACTGCTCCATC
CTGGCCGCCGTGGTTGTGGGCTTAGTGGCCTACATTGCCTTCAAGAGGTGGAACAGCTGCAAG
CAGAACAAGCAAGGAGCCAACAGCCGGCCCGTGAACCAGACGCCTCCGCCGGAGGGAGAAA
GCTCCACAGTGACAGTGGCATCTCTGTGGACAGCCAGAGCCTGCATGACCAGCAGCCCCACAC
ACAGACGGCCGCAGGCCAGGCCCTCAAGGGGGATGGAGGTCTCTACAGCAGCCTGCCACCAG
CCAAGCGGGAGGAGGTGGAGAAGCTGCTCAATGGCTCTGCGGGGGACACCTGGCGGCACCTG
GCAGGTGAGCTGGGCTACCAGCCTGAGCACATAGACTCCTTCACCCACGAGGCCTGCCCAGCC
CGAGCCCTGCTTGCCAGCTGGGCCGCCCAGGACAGCGCGACGCTCGACGCCCTCCTGGCTGC
TCTGCGCCGCATCCAGCGAGCCGACATCGTGGAGAGCCTGTGTAGCGAGTCCACGGCCACGTC
TCCAGTGTGA
Leader sequence is underlined SEQ ID NO: 3 feline p75NTR protein
<u>KEACPTGLFTHSGECCKACNLGEGVAQPCGANQTVCEPCLDSVTFSDVVSATEPCKPCTECVGLQS
MSAPCVEADDAVCRCAYGYYQDETTGRCEACRVCEAGSGLVFSCQDRQNTVCEECPDGTYSDEA
NHVDPCLPCTVCEDTERQLRECTRWADAECEEIPGRWITRSTPSEGSDSTAPSTEEPEVPPEQDLIA</u>
STVADVVTTVMGSSQPVVTRGTADNLIPVYCSILAAVVVGLVAYIAFKRWNSCKQDKQGANSRPVNQ
TPPPEGEKLHSDSGISVDSQSLHDQQSHTQTAAGQALKGDGGLYSSLPSAKREEVEKLLNGSAGDT
WRHLAGELGYQPEHIDSFTREACPARALLASWAAQDSATLDALLAALRRIQRADIVESLCSESTATSP
V
ECD is underlined SEQ ID NO: 4 feline p75NTR nucleic acid sequence
<u>ATGGACGGGCCGCGCCCGCTGCTGCTGCTGTTGCCGCTGCTCCTGGGGGTGTCCCTTGGAGGT
GCC</u>AAGGAGGCATGTCCCACGGGCCTGTTCACCCACAGCGGCGAGTGCTGTAAAGCCTGCAAC
CTGGGAGAGGGCGTAGCCCAGCCTTGCGGAGCCAACCAGACCGTGTGTGAGCCCTGCCTGGA
CAGCGTGACCTTCTCGGACGTGGTGAGCGCCACGGAGCCGTGCAAGCCGTGCACCGAGTGCGT
GGGCCTGCAGAGCATGTCGGCGCCGTGCGTGGAGGCCGACGACGCCGTGTGTCGCTGCGCCT
ACGGCTACTACCAGGACGAGACGACGGGCCGCTGCGAGGCGTGCCGCGTGTGCGAGGCGGGC
TCCGGCCTGGTGTTCTCGTGCCAGGACCGGCAGAATACCGTGTGCGAGGAGTGTCCCGACGGC
ACGTACTCGGACGAGGCCAACCACGTGGACCCGTGCCTGCCCTGCACCGTGTGCGAGGACACC
GAGCGCCAGCTGCGCGAGTGCACGCGCTGGGCCGACGCCGAGTGCGAGGAGATCCCTGGCCG
TTGGATTACTCGGTCTACACCTTCGGAGGGCTCGGACAGCACCGCCCCCAGCACGGAGGAGCC
AGAGGTACCTCCAGAGCAAGACCTCATAGCCAGCACGGTGGCAGATGTGGTGACCACAGTGAT
GGGCAGCTCTCAGCCCGTAGTGACCCGAGGCACCGCCGACAACCTCATCCCTGTCTATTGTTCC
ATCCTGGCCGCTGTGGTTGTGGGCCTGGTGGCCTACATTGCCTTCAAGAGGTGGAACAGCTGCA
AACAGGACAAGCAAGGCGCCAACAGCCGGCCCGTGAACCAGACGCCCCCGCCCGAGGGAGAA
AAGCTCCACAGTGACAGTGGCATCTCTGTGGACAGCCAGAGCCTGCATGACCAGCAGTCCCACA
CGCAGACGGCCGCGGCCAGGCCCTCAAGGGGACGAGGTCTCTACAGCAGCCTGCCGTCA
GCCAAGCGGGAGGAGGTAGAGAAACTGCTCAACGGCTCTGCGGGGGACACGTGGCGGCACCT
GGCGGGCGAGCTGGGCTACCAGCCTGAGCACATAGACTCCTTCACCCGCGAGGCCTGCCCAGC
CCGGGCCCTGCTCGCCAGCTGGGCCGCCCAGGACAGCGCGACGCTCGACGCCCTCCTGGCCG
CCCTGCGCCGCATCCAGCGGGCCGACATCGTCGAGAGCCTGTGCAGCGAGTCCACGGCCACG
TCCCCGGTGTGA
Leader sequence is underlined SEQ ID NO: 5 equine p75NTR protein
<u>KEVCPTDLYTHSGECCKACNLGEGVAQPCGANQTVCEPCLDSVTFSDVVSATEPCKPCTECVGLQS
MSAPCVEADDAVCRCAYGYYQDETTGRCEACQVCEAGSGLVFSCQDKQNTVCEECPDGTYSDEA
NHVDPCLPCTVCEDTERQLRECTRWADAECEEIPSRWITRATPPEGSDSTAPSTQEPEGPPEKDLVA</u>
STVADVVTTVMGSSQPVVTRGTTDNLIPVYCSILAAVVVGLVAYIAFKRWNSCKQNKQGANSRPVNQ
TPPPEGEKLHSDSGISVDSQSLHDQQPHTQTAAGQALKGDGGLYSSLPLAKREEVEKLLNGSAGDT
WRHLAGLVGQGLLRLELVSVFQGPAHGGMLPPATPSLQAPVWLGPEGCSEKWDQRGNAARRAGL
RVWPMEGLSQV
ECD is underlined

| Sequences |
|---|
| SEQ ID NO: 6 equine p75NTR nucleic acid sequence<br><u>ATGAGGGCAGGTGCCGCCGACTGCGCCATGGACGGACCGCGCCTTCTGCTGCTTCTGCTC<br>TTGGGGGTGTGCCTGCTGGGAGGTGCCAAGGAGGTGTGCCCCACAGACCTGTACACCCACAGC</u><br>GGCGAGTGCTGCAAAGCCTGCAACCTGGGCGAGGGTGTGGCCCAGCCTTGCGGAGCCAACCA<br>GACTGTGTGTGAACCCTGCCTGGACAGCGTGACGTTCTCGGACGTGGTGAGCGCCACAGAGCC<br>ATGTAAGCCGTGCACCGAGTGCGTGGGCCTGCAGAGCATGTCGGCGCCATGCGTGGAGGCCG<br>ACGACGCGGTGTGCCGCTGCGCCTATGGCTACTACCAGGACGAGACGACGGGCCGCTGCGAG<br>GCGTGCCAGGTGTGCGAGGCGGGCTCGGGCCTCGTGTTCTCGTGCCAGGACAAGCAGAACAC<br>CGTGTGCGAGGAATGCCCCGACGGCACGTACTCCGACGAGGCCAACCACGTGGACCCGTGCCT<br>GCCCTGCACCGTGTGCGAGGACACCGAGCGCCAGCTGCGAGAGTGCACGCGCTGGGCCGACG<br>CCGAGTGCGAGGAGATCCCCAGCCGTTGGATTACACGGGCCACGCCGCCGGAGGGCTCAGC<br>AGCACTGCCCCAGCACCCAGGAGCCCGAGGGACCTCCAGAGAAAGACCTTGTAGCCAGCACG<br>GTGGCGGATGTGGTGACCACAGTGATGGGCAGCTCTCAGCCCGTGGTGACCCGAGGCACCACG<br>GACAACCTCATCCCCGTCTATTGCTCCATCCTGGCCGCTGTGGTTGTGGGCCTTGTGGCCTACA<br>TCGCCTTCAAGAGGTGGAACAGCTGCAAGCAGAACAAGCAAGGAGCCAACAGCCGACCCGTGA<br>ACCAGACACCACCACCCGAGGGAGAAAAACTCCACAGCGACGACAGCGGCATCTCTGTGGACAGCC<br>AGAGCCTGCATGACCAGCAGCCTCACACACAGACAGCCGCAGGCCAGGCCCTCAAGGGAGATG<br>GAGGCCTCTACAGCAGCCTGCCACTGGCCAAGAGGGAAGAGGTGGAGAAGCTACTCAATGGCT<br>CCGCAGGGGACACCTGGCGGCACCTGGCGGGTGAGCTGGGCTACCAGCCCGAGCACATAGAC<br>TCCTTCACCCACGAGGCCTGCCCCGTCCGCGCCCTGCTTGCCAGCTGGGCCGCCAGGACAGT<br>GCGACATTCGATGCCCTCCTGACCGCCCTGCCGCCGCATCCAGCGAGCCGACATTGTCGAGAGC<br>CTGTGCAGCGAGTCCACCGCCACATCCCCGGTGTGA<br>Leader sequence is underlined |
| SEQ ID NO: 7 canine p75NTR protein ECD<br>KEACPTGLYTHSGECCKACNLGEGVAQPCGANQTVCEPCLDSVTFSDVVSATEPCKPCTECVGLQS<br>MSAPCVEADDAVCRCAYGYYQDETTGRCEACRVCEAGSGLVFSCQDRQNTVCEECPDGTYSDEA<br>NHVDPCLPCTVCEDTERQLRECTRWADAECEEIPGR<u>WITRSTPSEDSDSTAPSTEEPELPPDQEIIAS<br>TMADVVTTVM</u>GSSQPVVTRGTADN<br>The wt ECD region includes the stalk region (underlined) and alpha<br>and gamma secretase cleavage 3' of the stalk region (in bold) |
| SEQ ID NO: 8 canine p75NTR ECD nucleic acid sequence<br>AAGGAGGCATGTCCCACTGGCCTGTACACCCACAGCGGCGAGTGCTGCAAAGCCTGCAATCTG<br>GGTGAGGGGGTGGCCCAGCCTTGCGGAGCCAACCAGACCGTGTGTGAGCCCTGCCTGGACAG<br>CGTGACCTTCTCGGACGTGGTGAGCGCCACCGAGCCGTGCAAGCCGTGCACCGAGTGCGTGG<br>GGCTGCAGAGCATGTCGGCGCCGTGCGTGGAGGCGGACGACGCCGTGTGCCGCTGCGCCTAC<br>GGCTACTACCAGGACGAGACGACGGGCCGCTGCGAGGCGTGCCGCGTGTGCGAGGCGGGCTC<br>GGGGCTCGTGTTCTCGTGCCAGGACAGGCAGAACACCGTGTGCGAGGAGTGTCCCGACGGCAC<br>GTACTCCGACGAGGCCAACCACGTGGACCCGTGCCTGCCCTGCACCGTGTGCGAGGACACCGA<br>GCGCCAGCTGCGCGAGTGCACGCGCTGGGCCGACGCCGAGTGCGAGGAGATCCCTGGCCGTT<br>GGATTACCCGGTCCACACCCTCAGAGGACTCGGACAGCACCGCCCCAGCACAGAGGAGCCAG<br>AGCTACCTCCAGATCAAGAAATCATAGCCAGCACCATGGCAGATGTGGTGACCACAGTGATGGG<br>CAGCTCTCAGCCTGTAGTGACCCGAGGAACCGCTGACAAC |
| SEQ ID NO: 9 canine ECD of p75NTR stalk region protein<br>WITRSTPSEDSDSTAPSTEEPELPPDQEIIASTMADVVTTVM |
| SEQ ID NO: 10 canine ECD of p75NTR stalk region nucleic acid sequence<br>TGGATTACCCGGTCCACACCCTCAGAGGACTCGGACAGCACCGCCCCAGCACAGAGGAGCCA<br>GAGCTACCTCCAGATCAAGAAATCATAGCCAGCACCATGGCAGATGTGGTGACCACAGTGATG |
| SEQ ID NO: 11 canine p75NTR ECD - canine IgGB wt Fc protein fusion<br>*MEWSWVFLFFLSVTTGVHS*KEACPTGLYTHSGECCKACNLGEGVAQPCGANQTVCEPCLDSVTFS<br>DVVSATEPCKPCTECVGLQSMSAPCVEADDAVCRCAYGYYQDETTGRCEACRVCEAGSGLVFSCQ<br>DRQNTVCEECPDGTYSDEANHVDPCLPCTVCEDTERQLRECTRWADAECEEIPGGGG<u>RENGRYPR<br>PPDCPKCPAPEMLGGPSVFIFPPKPKDTLLIARTPEVTCVVVDLDPEDPEVQISWFVDGKQMQTAKT<br>QPREEQFNGTYRVVSVLPIGHQDWLKGKQFTCKVNNKALPSPIERTISKARGQAHQPSVYVLPPSRE<br>ELSKNTVSLTCLIKDFFPPDIDVEWQSNGQQEPESKYRTTPPQLDEDGSYFLYSKLSVDKSRWQRGD<br>TFICAVMHEALHNHYTQKSLSHSPGK</u><br><br>*Signal peptide*<br>Canine p75-ECD<br>Linker GGGG<br><u>Canine Fc-B wt</u> |
| SEQ ID NO: 12 canine p75NTR ECD - canine IgGB wt Fc nucleic acid sequence<br>ATGGAATGGTCCTGGGTGTTCCTGTTCTTCCTGTCCGTGACCACCGGCGTGCACTCCAAAGAGG<br>CTTGTCCTACCGGCCTGTACACCCACTCTGGCGAGTGTTGCAAGGCCTGTAATCTCGGCGAAGG<br>CGTGGCACAACCTTGTGGCGCTAATCAGACAGTGTGCGAGCCTTGCCTGGACTCCGTGACCTTC<br>TCTGATGTGGTGTCTGCCACCGAGCCATGCAAGCCTTGTACCGAGTGTGTGGGCCTGCAGTCCA<br>TGTCTGCCCCTTGTGTGGAAGCCGACGACGCCGTGTGTAGATGTGCCTACGGCTACTACCAGGA<br>CGAGACAACCGGAAGATGCGAGGCCTGCAGAGTGTGTGAAGCTGGCTCTGGACTGGTGTTCTC<br>CTGCCAAGACAGACAGAACACCGTGTGCGAGGAATGCCCTGACGGCACCTACTCTGATGAGGC<br>CAATCACGTGGACCCCTGCCTGCCTTGTACTGTGTGCGAAGATACCGAGCGGCAGCTGCGCGA<br>GTGTACCAGATGGGCTGATGCCGAGTGCGAAGAGATCCCTGGAGGTGGCGGACGCGAGAATGG<br>CAGAGTGCCTAGACCTCCTGACTGCCCTAAGTGCCCTGCCTCCTGAAATGCTCGGCGGACCCTCC |

| Sequences |
|---|
| GTGTTCATCTTCCCACCTAAGCCTAAGGACACCCTGCTGATCGCTCGGACCCCTGAAGTGACAT<br>GCGTGGTGGTGGATCTGGACCCCGAGGATCCTGAGGTGCAGATCAGTTGGTTCGTGGACGGCA<br>AGCAGATGCAGACCGCTAAGACCCAGCCTAGAGAGGAACAGTTCAACGGCACCTACAGAGTGG<br>TGTCTGTGCTGCCTATCGGCCACCAGGATTGGCTGAAGGGCAAGCAGTTTACCTGCAAAGTGAA<br>CAACAAGGCCCTGCCTTCTCCAATCGAGCGGACCATCTCTAAGGCCAGAGGCCAGGCTCATCAG<br>CCTTCCGTGTATGTCCTGCCACCTAGCCGCGAGGAACTGTCCAAGAACACCGTGTCTCTGACCT<br>GCCTGATCAAGGACTTCTTCCCTCCTGACATCGACGTGGAATGGCAGTCCAACGGCCAGCAAGA<br>GCCCGAGTCTAAGTACCGGACAACCCCTCCACAGCTGGACGAGGACGGCTCCTACTTCCTGTAC<br>TCCAAGCTGTCCGTGGACAAGTCTCGGTGGCAGAGAGGCGACACCTTCATCTGTGCTGTGATGC<br>ACGAGGCCCTGCACAACCACTACACCCAGAAGTCCCTGTCTCACTCCCTGGCAAGTGA<br>Leader sequence is underlined |
| SEQ ID NO: 13 canine p75NTR ECD - canine Fc YTE protein fusion<br><u>*MEWSWVFLFFLSVTTGVHS*</u>KEACPTGLYTHSGECCKACNLGEGVAQPCGANQTVCEPCLDSVTFS<br>DVVSATEPCKPCTECVGLQSMSAPCVEADDAVCRCAYGYYQDETTGRCEACRVCEAGSGLVFSCQ<br>DRQNTVCEECPDGTYSDEANHVDPCLPCTVCEDTERQLRECTRWADAECEEIPGGGG<u>RENGRYPR<br>PPDCPKCPAPEMLGGPSVFIFPPKPKDTLYITREPEVTCVVVDLDPEDPEVQISWFVDGKQMQTAKT<br>QPREEQFNGTYRVVSVLPIGHQDWLKGKQFTCKVNNKALPSPIERTISKARGQAHQPSVYVLPPSRE<br>ELSKNTVSLTCLIKDFFPPDIDVEWQSNGQQEPESKYRTTPPQLDEDGSYFLYSKLSVDKSRWQRGD<br>TFICAVMHEALHNHYTQKSLSHSPGK</u> |
| <u>*Signal peptide*</u><br>Canine p75-ECD<br>Linker GGGG<br><u>Canine Fc-B-YTE</u> |
| SEQ ID NO: 14 canine p75NTR ECD - Fc YTE nucleic acid sequence<br><u>ATGGAATGGTCCTGGGTGTTCCTGTTCTTCCTGTCCGTGACCACCGGCGTGCACTCCAAAGAGG<br>CTTGTCCTACCGGCCTGTACACCCACTCTGGCGAGTGTTGCAAGGCCTGTAATCTCGGCGAAGG<br>CGTGGCACAACCTTGTGGCGCTAATCAGACAGTGTGCGAGCCTTGCCTGGACTCCGTGACCTTC</u><br>TCTGATGTGGTGTCTGCCACCGAGCCATGCAAGCCTTGTACCGAGTGTGTGGGCCTGCAGTCCA<br>TGTCTGCCCCTTGTGTGGAAGCCGACGACGCCGTGTGTAGATGTGCCTACGGCTACTACCAGGA<br>CGAGACAACCGGAAGATGCGAGGCCTGCAGAGTGTGTGAAGCTGGCTCTGGACTGGTGTTCTC<br>CTGCCAAGACAGACAGAACACCGTGTGCGAGGAATGCCCTGACGGCACCTACTCTGATGAGGC<br>CAATCACGTGGACCCCTGCCTGCCTTGTACTGTGTGCGAAGATACCGAGCGGCAGCTGCGCGA<br>GTGTACCAGATGGGCTGATGCCGAGTGCGAAGAGATCCCTGGAGGTGGCGGACGCGAGAATGG<br>CAGAGTGCCTAGACCTCCTGACTGCCCTAAGTGCCCTGCTCCTGAAATGCTCGGCGGACCCTCC<br>GTGTTCATCTTCCCACCTAAGCCTAAGGACACCCTGTATATCACTCGGGAACCTGAAGTGACATG<br>CGTGGTGGTGGATCTGGACCCCGAGGATCCTGAGGTGCAGATCAGTTGGTTCGTGGACGGCAA<br>GCAGATGCAGACCGCTAAGACCCAGCCTAGAGAGGAACAGTTCAACGGCACCTACAGAGTGGT<br>GTCTGTGCTGCCTATCGGCCACCAGGATTGGCTGAAGGGCAAGCAGTTTACCTGCAAAGTGAAC<br>AACAAGGCCCTGCCTTCTCCAATCGAGCGGACCATCTCTAAGGCCAGAGGCCAGGCTCATCAGC<br>CTTCCGTGTATGTCCTGCCACCTAGCCGCGAGGAACTGTCCAAGAACACCGTGTCTCTGACCTG<br>CCTGATCAAGGACTTCTTCCCTCCTGACATCGACGTGGAATGGCAGTCCAACGGCCAGCAAGAG<br>CCCGAGTCTAAGTACCGGACAACCCCTCCACAGCTGGACGAGGACGGCTCCTACTTCCTGTACT<br>CCAAGCTGTCCGTGGACAAGTCTCGGTGGCAGAGAGGCGACACCTTCATCTGTGCTGTGATGCA<br>CGAGGCCCTGCACAACCACTACACCCAGAAGTCCCTGTCTCACTCCCTGGCAAGTGA<br>Leader sequence is underlined |
| SEQ ID NO: 15 IgG-A<br>MEFVLGWVFLVAILQGVQGEVQLVESGGDLVKPAGSLRLSCVASGFTFSNNAMNWVRQAPGKGLQ<br>WAGINSGGSTASADAVKGRFTISRDNAKNTVYLQMNSLTAEDTAVYYCAKVIGNWIATSDLDYWGQ<br>GTLVIVSSASTTAPSVFPLAPSCGSTSGSTVALACLVSGYFPEPVTVSWNSGSLTSGVHTFPSVLQSS<br>GLYSLSSMVTVPSSRWPSETFTCNVVHPASNTKVDKPVFNECRCTDTPPCPVPEPLGGPSVLIFPPK<br>PKDILRITRTPEVTCVVLDLGREDPEVQISWFVDGKEVHTAKTQSREQQFNGTYRVVSVLPIEHQDWL<br>TGKEFKCRVNHIDLPSPIERTISKARGRAHKPSVYVLPPSPKELSSSDTVSITCLIKDFYPPDIDVEWQS<br>NGQQEPERKHRMTPPQLDEDGSYFLYSKLSVDKSRWQQGDPFTCAVMHETLQNHYTDLSLSHSPG<br>K |
| SEQ ID NO: 16 IgG-B<br>MEFVLGWVFLVAILQGVQGEVQLVESGGDLVKPAGSLRLSCVASGFTFSNNAMNWVRQAPGKGLQ<br>WVAGINSGGSTASADAVKGRFTISRDNAKNTVYLQMNSLTAEDTAVYYCAKVIGNWIATSDLDYWGQ<br>GTLVIVSSASTTAPSVFPLAPSCGSTSGSTVALACLVSGYFPEPVTVSWNSGSLTSGVHTFPSVLQSS<br>GLYSLSSMVTVPSSRWPSETFTCNVAHPASKTKVDKPVPKRENGRVPRPPDCPKCPAPEMLGGPSV<br>FIFPPKPKDTLLIARTPEVTCVVVDLDPEDPEVQISWFVDGKQMQTAKTQPREEQFNGTYRVVSVLPI<br>GHQDWLKGKQFTCKVNNKALPSPIERTISKARGQAHQPSVYVLPPSREELSKNTVSLTCLIKDFFPPD<br>IDVEWQSNGQQEPESKYRTTPPQLDEDGSYFLYSKLSVDKSRWQRGDTFICAVMHEALHNHYTQKS<br>LSHSPGK |
| SEQ ID NO: 17 IgG-C<br>MEFVLGWVFLVAILQGVQGEVQLVESGGDLVKPAGSLRLSCVASGFTFSNNAMNWVRQAPGKGLQ<br>WVAGINSGGSTASADAVKGRFTISRDNAKNTVYLQMNSLTAEDTAVYYCAKVIGNWIATSDLDYWGQ<br>GTLVIVSSASTTAPSVFPLAPSCGSQSGSTVALACLVSGYIPEPVTVSWNSGSLTSGVHTFPSILQSS<br>GLYSLSSMVTVPSSRWPSETFTCNVAHPATNTKVDKPVVKECECKCNCNNCPCPGCGLLGGPSVFI<br>FPPKPKDILVTARTPTVTCVVVDLDPENPEVQISWFVDSKQVQTANTQPREEQSNGTYRVVSVLPIGH<br>QDWLSGKQFKCKVNNKALPSPIEEIISKTPGQAHPNVYVLPPSRDEMSKNTVTLTCLVKDFFPPEID |

| Sequences |
| --- |
| VEWQSNGQQEPESKYRMTPPQLDEDGSYFLYSKLSVDKSRWQRGDTFICAVMHEALHNHYTQKSL<br>SHSPGK<br><br>SEQ ID NO: 18 IgG-D<br>MEFVLGWVFLVAILQGVQGEVQLVESGGDLVKPAGSLRLSCVASGFTFSNNAMNWVRQAPGKGLQ<br>WVAGINSGGSTASADAVKGRFTISRDNAKNTVYLQMNSLTAEDTAVYYCAKVIGNWIATSDLDYWGQ<br>GTLVIVSSASSTAPSVFPLAPSCGSTSGSTVALACLVSGYFPEPVTVSWNSGSLTSGVHTFPSVLKSS<br>GLYSLSSMVTVPSSRLPSETFTCNWHPATNTKVDKPVPKESTCKCISPCPVPESLGGPSVFIFPPKP<br>KDILRITRTPEVTCWLDLGREDPEVQISWFVDGKEVHTAKTQPREQQFNSTYRWSVLPIEHQDWLT<br>GKEFKCRVNHIGLPSPIERTISKARGQAHQPGVYVLPPSPKELSSSDTVTLTCLIKDFFPPEIDVEWQS<br>NGQPEPESKYHTTAPQLDEDGSYFLYSKLSVDKSRWQQGDPFTCAVMHEALQNHYTDLSLSHSPG<br>K<br><br>SEQ ID NO: 19<br>DOGA constant region<br>FNECRCTDTPPCPVPEPLGGPSVLIFPPKPKDILRITRTPEVTCWLDLGREDPEVQISWFVDGKEVHT<br>AKTQSREQQFNGTYRVVSVLPIEHQDWLTGKEFKCRVNHIDLPSPIERTISKARGRAHKPSVYVLPPS<br>PKELSSSDTVSITCLIKDFYPPDIDVEWQSNGQQEPERKHRMTPPQLDEDGSYFLYSKLSVDKSRWQ<br>QGDPFTCAVMHETLQNHYTDLSLSHSPGK<br><br>SEQ ID NO: 20<br>DOGB constant region<br>RENGRVPRPPDCPKCPAPEMLGGPSVFIFPPKPKDTLLIARTPEVTCWVDLDPEDPEVQISWFVDG<br>KQMQTAKTQPREEQFNGTYRVVSVLPIGHQDWLKGKQFTCKVNNKALPSPIERTISKARGQAHQPS<br>VYVLPPSREELSKNTVSLTCLIKDFFPPDIDVEWQSNGQQEPESKYRTTPPQLDEDGSYFLYSKLSVD<br>KSRWQRGDTFICAVMHEALHNHYTQKSLSHSPGK<br><br>SEQ ID NO: 21<br>DOGB-YTE constant region<br>RENGRVPRPPDCPKCPAPEMLGGPSVFIFPPKPKDTLYITREPEVTCVVVDLDPEDPEVQISWFVDG<br>KQMQTAKTQPREEQFNGTYRVVSVLPIGHQDWLKGKQFTCKVNNKALPSPIERTISKARGQAHQPS<br>VYVLPPSREELSKNTVSLTCLIKDFFPPDIDVEWQSNGQQEPESKYRTTPPQLDEDGSYFLYSKLSVD<br>KSRWQRGDTFICAVMHEALHNHYTQKSLSHSPGK<br><br>SEQ ID NO: 22<br>DOGC constant region<br>ECECKCNCNNCPCPGCGLLGGPSVFIFPPKPKDILVTARTPTVTCVVVDLDPENPEVQISWFVDSKQ<br>VQTANTQPREEQSNGTYRVVSVLPIGHQDWLSGKQFKCKVNNKALPSPIEEIISKTPGQAHQPNVYV<br>LPPSRDEMSKNTVTLTCLVKDFFPPEIDVEWQSNGQQEPESKYRMTPPQLDEDGSYFLYSKLSVDKS<br>RWQRGDTFICAVMHEALHNHYTQKSLSHSPGK<br><br>SEQ ID NO: 23<br>DOGD constant region<br>ESTCKCISPCPVPESLGGPSVFIFPPKPKDILRITRTPEVTCVVLDLGREDPEVQISWFVDGKEVHTAK<br>TQPREQQFNSTYRVVSVLPIEHQDWLTGKEFKCRVNHIGLPSPIERTISKARGQAHQPGVYVLPPSPK<br>ELSSSDTVTLTCLIKDFFPPEIDVEWQSNGQPEPESKYHTTAPQLDEDGSYFLYSKLSVDKSRWQQG<br>DPFTCAVMHEALQNHYTDLSLSHSPGK<br><br>SEQ ID NO: 24<br>CAT_IGG1V1 constant region<br>TDHPPGPKPCDCPKCPPPEMLGGPSIFIFPPKPKDTLSISRTPEVTCLVVDLGPDDSDVQITWFVDNT<br>QVYTAKTSPREEQFNSTYRVVSVLPILHQDWLKGKEFKCKVNSKSLPSPIERTISKAKGQPHEPQVYV<br>LPPAQEELSRNKVSVTCLIKSFHPPDIAVEWEITGQPEPENNYRTTPPQLDSDGTYFVYSKLSVDRSH<br>WQRGNTYTCSVSHEALHSHHTQKSLTQSPGK<br><br>SEQ ID NO: 25<br>CAT_IGG1V2 constant region<br>TDHPPGPKPCDCPKCPPPEMLGGPSIFIFPPKPKDTLSISRTPEVTCLVVDLGPDDSDVQITWFVDNT<br>QVYTAKTSPREEQFNSTYRVVSVLPILHQDWLKGKEFKCKVNSKSLPSPIERTISKAKGQPHEPQVYV<br>LPPAQEELSRNKVSVTCLIKSFHPPDIAVEWEITGQPEPENNYRTTPPQLDSDGTYFVYSKLSVDRSH<br>WQRGNTYTCSVSHEALHSHHTQKSLTQSPGK<br><br>SEQ ID NO: 26<br>CAT_IGG2 constant region<br>KTASTIESKTGEGPKCPVPEIPGAPSVFIFPPKPKDTLSISRTPEVTCLVVDLGPDDSNVQITWFVDNT<br>EMHTAKTRPREEQFNSTYRVVSVLPILHQDWLKGKEFKCKVNSKSLPSAMERTISKAKGQPHEPQVY<br>VLPPTQEELSENKVSVTCLIKGFHPPDIAVEWEITGQPEPENNYQTTPPQLDSDGTYFLYSRLSVDRS<br>HWQRGNTYTCSVSHEALHSHHTQKSLTQSPGK<br><br>SEQ ID NO: 27<br>HORSE_IGHG1 constant region<br>VIKECNGGCPAECLQVGPSVFIFPPKPKDVLMISRTPTVTCWVDVGHDFPDVQFNWYVDGVETHTA<br>TTEPKQEQFNSTYRVVSVLPIQHKDWLSGKEFKCKVNNKALPAPVERTISKPTGQPREPQVYVLAPH<br>RDELSKNKVSVTCLVKDFYPTDIDIEWKSNGQPEPETKYSTTPAQLDSDGSYFLYSKLTVETNRWQQ<br>GTTFTCAVMHEALHNHYTEKSVSKSPGK |

| Sequences |
| --- |

SEQ ID NO: 28
HORSE_IGHG2 constant region
CVLSAEGVIPIPSVPKPQCPPYTHSKFLGGPSVFIFPPNPKDALMISRTPWTCVVVNLSDQYPDVQFS
WYVDNTEVHSAITKQREAQFNSTYRVVSVLPIQHQDWLSGKEFKCSVTNVGVPQPISRAISRGKGPS
RVPQVYVLPPHPDELAKSKVSVTCLVKDFYPPDISVEWQSNRWPELEGKYSTTPAQLDGDGSYFLYS
KLSLETSRWQQVESFTCAVMHEALHNHFTKTDISESLGK SEQ ID NO: 29
HORSE_IGHG3
TTPPCPCECPKCPAPELLGGPSVFIFPPKPKDVLMITRTPEVTCLVVDVSHDSSDVLFTWYVDGTEVK
TAKTMPNEEQNNSTYRVVSVLRIQHQDWLNGKKFKCKVNNQALPAPVERTISKATGQTRVPQVYVLA
PHPDELSKNKVSVTCLVKDFLPTDITVEWQSNEHPEPEGKYRTTEAQKDSDGSYFLYSKLTVETDRW
QQGTTFTCWMHEALHNHVMQKNVSHSPGK SEQ ID NO: 30
HORSE_IGHG4 constant region
VIKECNGGCPAECLQVGPSVFIFPPKPKDVLMISRTPTVTCWVDVGHDFPDVQFNWYVDGVETHTA
TTEPKQEQFNSTYRVVSVLPIQHKDWLSGKEFKCKVNNKALPAPVERTISKPTGQPREPQVYVLAPH
RDELSKNKVSVTCLVKDFYPTDIDIEWKSNGQPEPETKYSTTPAQLDSDGSYFLYSKLTVETNRWQQ
GTTFTCAVMHEALHNHYTEKSVSKSPGK SEQ ID NO: 31
HORSE_IGHG5 constant region
WKGSPCPKCPAPELPGGPSVFIFPPKPKDVLKISRKPEVTCVWDLGHDDPDVQFTWFVDGVETHT
ATTEPKEEQFNSTYRVVSVLPIQHQDWLSGKEFKCSVTNKALPAPVERTTSKAKGQLRVPQVYVLAP
HPDELAKNTVSVTCLVKDFYPPEIDVEWQSNEHPEPEGKYSTTPAQLNSDGSYFLYSKLSVETSRWK
QGESFTCGVMHEAVENHYTQKNVSHSPGK SEQ ID NO: 32
>HORSE_IGHG6 constant region
KEPCCCPKCPGRPSVFIFPPNPKDTLMISRTPEVTCVVVDVSQENPDVKFNWYVDGVEAHTATTKAK
EKQDNSTYRVVSVLPIQHQDWRRGKEFKCKVNNRALPAPVERTITKAKGELQDPKVYILAPHREEVT
KNTVSVTCLVKDFYPPDINVEWQSNEEPEPEVKYSTTPAQLDGDGSYFLYSKLTVETDRWEQGESFT
CVVMHEAIRHTYRQKSITNFPGK SEQ ID NO: 33
HORSE_IGHG7 constant region
VIKECGGCPTCPECLSVGPSVFIFPPKPKDVLMISRTPTVTCWVDVGHDFPDVQFNWYVDGVETHT
ATTEPKQEQNNSTYRVVSILAIQHKDWLSGKEFKCKVNNQALPAPVQKTISKPTGQPREPQVYVLAP
HRDELSKNKVSVTCLVKDFYPTDIDIEWKSNGQPEPETKYSTTPAQLDSDGSYFLYSKLTVETNRWQ
QGTTFTCAVMHEALHNHYTEKSVSKSPGK SEQ ID NO: 34 portion of canine ECD as used in the fusion constructs
(without stalk and without alpha and gamma secretase cleavage 3' of
the stalk region)
KEACPTGLYTHSGECCKACNLGEGVAQPCGANQTVCEPCLDSVTFSDVVSATEPCKPCTECVGLQS
MSAPCVEADDAVCRCAYGYYQDETTGRCEACRVCEAGSGLVFSCQDRQNTVCEECPDGTYSDEA
NHVDPCLPCTVCEDTERQLRECTRWADAECEEIPKEACPTGLYTHSGECCKACNLGEGVAQPCGAN
QTVCEPCLDSVTFSDVVSATEPCKPCTECVGLQSMSAPCVEADDAVCRCAYGYYQDETTGRCEAC
RVCEAGSGLVFSCQDRQNTVCEECPDGTYSDEANHVDPCLPCTVCEDTERQLRECTRWADAECEE
IP SEQ ID NO: 35 canine p75NTR ECD nucleic acid sequence as used in
the fusion constructs (without stalk and without alpha and gamma
secretase cleavage 3' of the stalk region)
AAGGAGGCATGTCCCACTGGCCTGTACACCCACAGCGGCGAGTGCTGCAAAGCCTGCAATCTG
GGTGAGGGGGTGGCCCAGCCTTGCGGAGCCAACCAGACCGTGTGGAGCCCTGCCTGGACAG
CGTGACCTTCTCGGACGTGGTGAGCGCCACCGAGCCGTGCAAGCCGTGCACCGAGTGCGTGG
GGCTGCAGAGCATGTCGGCGCCGTGCGTGGAGGCGGACGACGCCGTGTGCCGCTGCGCCTAC
GGCTACTACCAGGACGAGACGACGGGCCGCTGCGAGGCGTGCCGCGTGTGCGAGGCGGGCTC
GGGGCTCGTGTTCTCGTGCCAGGACAGGCAGAACACCGTGTGCGAGGAGTGTCCCGACGGCAC
GTACTCCGACGAGGCCAACCACGTGGACCCGTGCCTGCCCTGCACCGTGTGCGAGGACACCGA
GCGCCAGCTGCGCGAGTGCACGCGCTGGGCCGACGCCGAGTGCGAGGAGATCCCTGGCCGT SEQ ID NO: 36 bovine p75 NTR protein
<u>KEACLTGLYTHSGECCKACNLGEGVAQPCGANQTVCEPCLDSVTFSDVVSATEPCKPCTECVGLQS
MSAPCVEADDAVCRCAYGYYQDETTGRCEACRVCEAGSGLVFSCQDKQNTVCEECPDGTYSDEAN
HVDPCLPCTVCEDTERQLRECTRWADAECEEIPGRWITRATPPEGSDSTDPSTQEPEVPPEQDLVT
STVSDVVTTVMGSSQPVVTRGTADNL</u>IPVYCSILAAVVVGLVAYIAFKRWNSCKQNKQGANSRPVNQ
TPPPEGEKLHSDSGISVDSQSLHDQQPHTQTAAGQALKGDGGLYSSLPLAKREEVEKLLNGSAGDT
WRHLAGELGYQPEHIDSFTHEACPARALLASWAAQDSATLDTLLAALRRIQRADLVESLCSESTATSP
V
ECD is underlined SEQ ID NO: 37 bovine p75 NTR nucleic acid
ATGGGGTCAGGTGCCGCCGGCCGCGCCATGGACGGGCCGCGCCTGCTGCTGCTGCTGCTGCT
GCTCCTGGGGGTGTCCCTTGGAGGTGCCAAGGAAGCATGCCTCACGGGCCTGTACACCCACAG -continued

| Sequences |
|---|
| CGGAGAGTGCTGCAAAGCCTGCAACCTGGGCGAGGGTGTGGCCCAGCCTTGTGGAGCCAACCA |
| GACCGTGTGTGAACCCTGCCTGGACAGCGTGACCTTCTCGGACGTGGTGAGCGCCACGGAGCC |
| GTGTAAGCCGTGCACGGAGTGCGTGGGACTGCAGAGCATGTCGGCGCCCTGCGTGGAGGCCG |
| ACGACGCCGTGTGCCGCTGCGCCTACGGCTATTACCAGGACGAGACGACCGGCCGCTGCGAG |
| GCGTGCCGCGTGTGCGAGGCGGGCTCGGGGCTCGTGTTCTCGTGCCAGGACAAGCAGAACAC |
| CGTCTGCGAGGAGTGCCCCGACGGCACGTACTCCGACGAGGCCAACCACGTGGACCCCTGCCT |
| GCCCTGCACGGTGTGCGAGGACACGGAGCGCCAGCTGCGCGAGTGCACGCGCTGGGCCGACG |
| CCGAGTGCGAGGAGATCCCTGGACGTTGGATTACACGGGCCACGCCCCTGAGGGCTCCGACA |
| GCACAGACCCCAGCACCCAGGAGCCCGAGGTACCTCCAGAGCAAGATCTGGTAACCAGCACTG |
| TGTCAGATGTGGTGACCACGGTGATGGGCAGCTCCCAGCCTGTGGTGACCCGAGGTACCGCCG |
| ACAACCTCATCCCTGTCTATTGCTCCATCCTGGCTGCTGTGGTTGTGGGCCTTGTGGCCTACATC |
| GCCTTCAAGAGGTGGAACAGCTGCAAGCAGAACAAGCAAGGAGCCAACAGCCGACCTGTGAAC |
| CAGACACCCCACCAGAGGGGGAAAAGCTACACAGCGATAGCGGCATCTCTGTGGACAGCCAG |
| AGCCTGCATGACCAGCAGCCCCACACGCAGACTGCCGCAGGCCAGGCCCTCAAGGGTGATGGA |
| GGCCTCTACAGCAGCCTGCCGCTGGCCAAGCGGGAGGAGGTGGAGAAGCTGCTCAACGGCTCT |
| GCGGGGACACCTGGCGGCATCTGGCAGGCGAGTTGGGTTACCAGCCTGAGCACATAGACTCC |
| TTCACCCACGAGGCCTGCCCAGCCCGCGCCCTGCTGGCCAGCTGGGCTGCCCAGGACAGCGC |
| CACGCTCGACACCCTCCTTGCGGCCCTGCGCCGCATCCAGCGCGCCGACATCGTGGAGAGCCT |
| GTGCAGCGAGTCCACGGCCACGTCCCCGTGTGA |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A fusion protein comprising an extracellular domain of a companion animal p75 neurotrophin receptor protein and a half-life extending moiety; wherein, the fusion protein comprises SEQ ID NO: 11 or 13.

2. A fusion protein according to claim 1 wherein the half-life extending moiety is an Fc domain, a serum albumin binder or PEG.

3. A fusion protein according to claim 2 wherein the half-life extending moiety is a wild type or mutant Fc domain.

4. A fusion protein according to claim 1 wherein the half-life extending moiety is an Fc domain and the p75NTR extracellular domain or portion thereof and the Fc domain are linked with a linker.

5. A fusion protein according to claim 4 wherein the linker is a peptide linker optionally where the peptide linker is $(G_4S)_n$ (SEQ ID NO: 38) wherein n is 1 to 4.

6. A fusion protein according to claim 1 wherein the companion animal is a cat, dog, cow or horse.

7. A pharmaceutical composition comprising the fusion protein according to claim 1.

8. A method for treating a nerve growth factor NGF-related disorder in a companion animal comprising administering an effective amount of the fusion protein according to claim 1.

9. The method of claim 8 wherein the NGF-related disorder is cardiovascular disease, atherosclerosis, obesity, type 2 diabetes, metabolic syndrome, pain and inflammation.

10. The method of claim 9 wherein the NGF-related disorder is a pain related disorder.

11. The method of claim 10 wherein the pain is selected from osteoarthritis pain, rheumatoid arthritis pain, surgical and postsurgical pain, incisional pain, general inflammatory pain, cancer pain, pain from trauma, neuropathic pain, neuralgia, diabetic neuropathy pain, pain associated with rheumatic diseases, pain associated with musculoskeletal diseases, visceral pain, and gastrointestinal pain.

12. The method according to claim 9 comprising administration of a second compound that treats pain.

\* \* \* \* \*

SEQUENCE LISTING

<160> NUMBER OF SEQ ID NOS: 38

<210> SEQ ID NO 1
<211> LENGTH: 399
<212> TYPE: PRT
<213> ORGANISM: Canis familiaris

<400> SEQUENCE: 1

```
Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Arg Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Ser Glu Asp
                165                 170                 175

Ser Asp Ser Thr Ala Pro Ser Thr Glu Glu Pro Glu Leu Pro Pro Asp
            180                 185                 190

Gln Glu Ile Ile Ala Ser Thr Met Ala Asp Val Val Thr Val Met
        195                 200                 205
```

```
Gly Ser Ser Gln Pro Val Val Thr Arg Gly Thr Ala Asp Asn Leu Ile
    210                 215                 220
Pro Val Tyr Cys Ser Ile Leu Ala Ala Val Val Gly Leu Val Ala
225                 230                 235                 240
Tyr Ile Ala Phe Lys Arg Trp Asn Ser Cys Lys Gln Asn Lys Gln Gly
                245                 250                 255
Ala Asn Ser Arg Pro Val Asn Gln Thr Pro Pro Glu Gly Glu Lys
            260                 265                 270
Leu His Ser Asp Ser Gly Ile Ser Val Asp Ser Gln Ser Leu His Asp
            275                 280                 285
Gln Gln Pro His Thr Gln Thr Ala Ala Gly Gln Ala Leu Lys Gly Asp
    290                 295                 300
Gly Gly Leu Tyr Ser Ser Leu Pro Pro Ala Lys Arg Glu Glu Val Glu
305                 310                 315                 320
Lys Leu Leu Asn Gly Ser Ala Gly Asp Thr Trp Arg His Leu Ala Gly
                325                 330                 335
Glu Leu Gly Tyr Gln Pro Glu His Ile Asp Ser Phe Thr His Glu Ala
            340                 345                 350
Cys Pro Ala Arg Ala Leu Leu Ala Ser Trp Ala Ala Gln Asp Ser Ala
            355                 360                 365
Thr Leu Asp Ala Leu Leu Ala Ala Leu Arg Arg Ile Gln Arg Ala Asp
    370                 375                 380
Ile Val Glu Ser Leu Cys Ser Glu Ser Thr Ala Thr Ser Pro Val
385                 390                 395
```

<210> SEQ ID NO 2
<211> LENGTH: 1263
<212> TYPE: DNA
<213> ORGANISM: Canis familiaris

<400> SEQUENCE: 2

```
atggacgggc cgcgcctgct gctgctgctg ctgctgctcc tggggggtgtc ccttggaggt      60
gccaaggagg catgtcccac tggcctgtac acccacagcg gcgagtgctg caaagcctgc     120
aatctgggtg aggggtggc ccagccttgc ggagccaacc agaccgtgtg tgagccctgc     180
ctggacagcg tgaccttctc ggacgtggtg agcgccaccg agccgtgcaa gccgtgcacc     240
gagtgcgtgg ggctgcagag catgtcggcg ccgtgcgtgg aggcggacga cgccgtgtgc     300
cgctgcgcct acggctacta ccaggacgag acgacgggcc gctgcgaggc gtgccgcgtg     360
tgcgaggcgg gctcggggct cgtgttctcg tgccaggaca gcagaacac cgtgtgcgag     420
gagtgtcccg acggcacgta ctccgacgag gccaaccacg tggaccccgtg cctgccctgc     480
accgtgtgcg aggacaccga cgccagctg cgcgagtgca cgcgctgggc cgacgccgag     540
tgcgaggaga tccctggccg ttggattacc cggtccacac cctcagagga ctcggacagc     600
accgccccca gcacagagga gccagagcta cctccagatc aagaaatcat agccagcacc     660
atggcagatg tggtgaccac agtgatgggc agctctcagc ctgtagtgac ccgaggaacc     720
gctgacaacc tcatccctgt ctactgctcc atcctggccg ccgtggttgt gggcttagtg     780
gcctacattg ccttcaagag gtggaacagc tgcaagcaga acaagcaagg agccaacagc     840
cggcccgtga accagacgcc tccgccggag ggagaaaagc tccacagtga cagtggcatc     900
tctgtggaca ccagagcct gcatgaccag cagcccaca cacagacggc cgcaggccag     960
gccctcaagg gggatggagg tctctacagc agcctgccac cagccaagcg ggaggaggtg    1020
```

-continued

```
gagaagctgc tcaatggctc tgcgggggac acctggcggc acctggcagg tgagctgggc      1080
taccagcctg agcacataga ctccttcacc cacgaggcct gcccagcccg agccctgctt      1140
gccagctggg ccgcccagga cagcgcgacg ctcgacgccc tcctggctgc tctgcgccgc      1200
atccagcgag ccgacatcgt ggagagcctg tgtagcgagt ccacggccac gtctccagtg      1260
tga                                                                    1263

<210> SEQ ID NO 3
<211> LENGTH: 399
<212> TYPE: PRT
<213> ORGANISM: Felis catus

<400> SEQUENCE: 3

Lys Glu Ala Cys Pro Thr Gly Leu Phe Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Gly Arg Cys Glu Ala
                85                  90                  95

Cys Arg Val Cys Glu Ala Gly Ser Gly Leu Val Phe Ser Cys Gln Asp
            100                 105                 110

Arg Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Ser Glu Gly
                165                 170                 175

Ser Asp Ser Thr Ala Pro Ser Thr Glu Glu Pro Glu Val Pro Pro Glu
            180                 185                 190

Gln Asp Leu Ile Ala Ser Thr Val Ala Asp Val Val Thr Thr Val Met
        195                 200                 205

Gly Ser Ser Gln Pro Val Val Thr Arg Gly Thr Ala Asp Asn Leu Ile
    210                 215                 220

Pro Val Tyr Cys Ser Ile Leu Ala Ala Val Val Gly Leu Val Ala
225                 230                 235                 240

Tyr Ile Ala Phe Lys Arg Trp Asn Ser Cys Lys Gln Asp Lys Gln Gly
                245                 250                 255

Ala Asn Ser Arg Pro Val Asn Gln Thr Pro Pro Glu Gly Glu Lys
            260                 265                 270

Leu His Ser Asp Ser Gly Ile Ser Val Asp Ser Gln Ser Leu His Asp
        275                 280                 285

Gln Gln Ser His Thr Gln Thr Ala Ala Gly Gln Ala Leu Lys Gly Asp
    290                 295                 300

Gly Gly Leu Tyr Ser Ser Leu Pro Ser Ala Lys Arg Glu Glu Val Glu
305                 310                 315                 320

Lys Leu Leu Asn Gly Ser Ala Gly Asp Thr Trp Arg His Leu Ala Gly
```

```
                    325                 330                 335
Glu Leu Gly Tyr Gln Pro Glu His Ile Asp Ser Phe Thr Arg Glu Ala
            340                 345                 350

Cys Pro Ala Arg Ala Leu Leu Ala Ser Trp Ala Ala Gln Asp Ser Ala
        355                 360                 365

Thr Leu Asp Ala Leu Leu Ala Ala Leu Arg Arg Ile Gln Arg Ala Asp
    370                 375                 380

Ile Val Glu Ser Leu Cys Ser Glu Ser Thr Ala Thr Ser Pro Val
385                 390                 395
```

<210> SEQ ID NO 4
<211> LENGTH: 1266
<212> TYPE: DNA
<213> ORGANISM: Felis catus

<400> SEQUENCE: 4

```
atggacgggc cgcgcccgct gctgctgctg ttgccgctgc tcctgggggt gtcccttgga      60
ggtgccaagg aggcatgtcc cacgggcctg ttcacccaca gcggcgagtg ctgtaaagcc     120
tgcaacctgg gagagggcgt agcccagcct tgcggagcca accagaccgt gtgtgagccc     180
tgcctggaca gcgtgacctt ctcggacgtg gtgagcgcca cggagccgtg caagccgtgc     240
accgagtgcg tgggcctgca gagcatgtcg gcgccgtgcg tggaggccga cgacgccgtg     300
tgtcgctgcg cctacggcta ctaccaggac gagacgacgg gccgctgcga ggcgtgccgc     360
gtgtgcgagg cgggctccgg cctggtgttc tcgtgccagg accggcagaa taccgtgtgc     420
gaggagtgtc ccgacggcac gtactcggac gaggccaacc acgtggaccc gtgcctgccc     480
tgcaccgtgt gcgaggacac cgagcgccag ctgcgcgagt gcacgcgctg gccgacgcc      540
gagtgcgagg agatccctgg ccgttggatt actcggtcta caccttcgga gggctcggac     600
agcaccgccc ccagcacgga ggagccagag gtacctccag agcaagacct catagccagc     660
acggtggcag atgtggtgac cacagtgatg ggcagctctc agcccgtagt gacccgaggc     720
accgccgaca acctcatccc tgtctattgt tccatcctgg ccgctgtggt tgtgggcctg     780
gtggcctaca ttgccttcaa gaggtggaac agctgcaaac aggacaagca aggcgccaac     840
agccggcccg tgaaccagac gccccgccc gagggagaaa agctccacag tgacagtggc     900
atctctgtgg acagccagag cctgcatgac agcagtccc acacgcagac ggccgccggc     960
caggccctca gggggacgg aggtctctac agcagcctgc cgtcagccaa gcgggaggag    1020
gtagagaaac tgctcaacgg ctctgcgggg gacacgtggc ggcacctggc gggcgagctg    1080
ggctaccagc ctgagcacat agactccttc acccgcgagg cctgcccagc ccgggccctg    1140
ctcgccagct gggccgccca ggacagcgcg acgctcgacg ccctcctggc cgccctgcgc    1200
cgcatccagc gggccgacat cgtcgagagc ctgtgcagcg agtccacggc cacgtccccg    1260
gtgtga                                                               1266
```

<210> SEQ ID NO 5
<211> LENGTH: 405
<212> TYPE: PRT
<213> ORGANISM: Equus caballus

<400> SEQUENCE: 5

```
Lys Glu Val Cys Pro Thr Asp Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30
```

```
Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
 50                  55                  60

Gln Ser Met Ser Ala Pro Cys Val Glu Ala Asp Asp Ala Val Cys Arg
 65                  70                  75                  80

Cys Ala Tyr Gly Tyr Tyr Gln Asp Glu Thr Thr Gly Arg Cys Glu Ala
                85                  90                  95

Cys Gln Val Cys Glu Ala Gly Ser Gly Leu Val Phe Ser Cys Gln Asp
                100                 105                 110

Lys Gln Asn Thr Val Cys Glu Cys Pro Asp Gly Thr Tyr Ser Asp
            115                 120                 125

Glu Ala Asn His Val Asp Pro Cys Leu Pro Cys Thr Val Cys Glu Asp
        130                 135                 140

Thr Glu Arg Gln Leu Arg Glu Cys Thr Arg Trp Ala Asp Ala Glu Cys
145                 150                 155                 160

Glu Glu Ile Pro Ser Arg Trp Ile Thr Arg Ala Thr Pro Pro Glu Gly
                165                 170                 175

Ser Asp Ser Thr Ala Pro Ser Thr Gln Glu Pro Glu Gly Pro Pro Glu
            180                 185                 190

Lys Asp Leu Val Ala Ser Thr Val Ala Asp Val Val Thr Thr Val Met
            195                 200                 205

Gly Ser Ser Gln Pro Val Val Thr Arg Gly Thr Thr Asp Asn Leu Ile
210                 215                 220

Pro Val Tyr Cys Ser Ile Leu Ala Ala Val Val Val Gly Leu Val Ala
225                 230                 235                 240

Tyr Ile Ala Phe Lys Arg Trp Asn Ser Cys Lys Gln Asn Lys Gln Gly
                245                 250                 255

Ala Asn Ser Arg Pro Val Asn Gln Thr Pro Pro Glu Gly Glu Lys
            260                 265                 270

Leu His Ser Asp Ser Gly Ile Ser Val Asp Ser Gln Ser Leu His Asp
            275                 280                 285

Gln Gln Pro His Thr Gln Thr Ala Ala Gly Gln Ala Leu Lys Gly Asp
        290                 295                 300

Gly Gly Leu Tyr Ser Ser Leu Pro Leu Ala Lys Arg Glu Glu Val Glu
305                 310                 315                 320

Lys Leu Leu Asn Gly Ser Ala Gly Asp Thr Trp Arg His Leu Ala Gly
                325                 330                 335

Leu Val Gly Gln Gly Leu Leu Arg Leu Glu Leu Val Ser Val Phe Gln
            340                 345                 350

Gly Pro Ala His Gly Met Leu Pro Pro Ala Thr Pro Ser Leu Gln
        355                 360                 365

Ala Pro Val Trp Leu Gly Pro Glu Gly Cys Ser Glu Lys Trp Asp Gln
    370                 375                 380

Arg Gly Asn Ala Ala Arg Arg Ala Gly Leu Arg Val Trp Pro Met Glu
385                 390                 395                 400

Gly Leu Ser Gln Val
            405

<210> SEQ ID NO 6
<211> LENGTH: 1290
<212> TYPE: DNA
<213> ORGANISM: Equus caballus
```

<400> SEQUENCE: 6

```
atgagggcag gtgccgccga ctgcgccatg gacggaccgc gccttctgct gctgcttctg    60
ctcttggggg tgtgcctgct gggaggtgcc aaggaggtgt gccccacaga cctgtacacc   120
cacagcggcg agtgctgcaa agcctgcaac ctgggcgagg tgtggcccca gccttgcgga   180
gccaaccaga ctgtgtgtga accctgcctg acagcgtga cgttctcgga cgtggtgagc   240
gccacagagc catgtaagcc gtgcaccgag tgcgtgggcc tgcagagcat gtcggcgcca   300
tgcgtggagg ccgacgacgc ggtgtgccgc tgcgcctatg gctactacca ggacgagacg   360
acgggccgct gcgaggcgtg ccaggtgtgc gaggcgggct cgggcctcgt gttctcgtgc   420
caggacaagc agaacaccgt gtgcgaggaa tgccccgacg gcacgtactc cgacgaggcc   480
aaccacgtgg acccgtgcct gccctgcacc gtgtgcgagg acaccgagcg ccagctgcga   540
gagtgcacgc gctgggccga cgccgagtgc gaggagatcc ccagccgttg gattacacgg   600
gccacgccgc cggagggctc agacagcact gcccccagca cccaggagcc cgagggacct   660
ccagagaaag accttgtagc cagcacggtg gcggatgtgg tgaccacagt gatgggcagc   720
tctcagcccg tggtgacccg aggcaccacg gacaacctca tccccgtcta ttgctccatc   780
ctggccgctg tggttgtggg ccttgtggcc tacatcgcct tcaagaggtg gaacagctgc   840
aagcagaaca gcaaggagc caacagccga cccgtgaacc agacaccacc acccgaggga   900
gaaaaactcc acagcgacag cggcatctct gtggacagcc agagcctgca tgaccagcag   960
cctcacacac agacagccgc aggccaggcc ctcaagggag atggaggcct ctacagcagc  1020
ctgccactgg ccaagaggga agaggtggag aagctactca atggctccgc aggggacacc  1080
tggcggcacc tggcgggtga gctgggctac cagcccgagc acatagactc cttcacccac  1140
gaggcctgcc ccgtccgcgc cctgcttgcc agctgggccg cccaggacag tgcgacattc  1200
gatgccctcc tgaccgccct gcgccgcatc cagcgagccg acattgtcga gagcctgtgc  1260
agcgagtcca ccgccacatc cccggtgtga                                    1290
```

<210> SEQ ID NO 7
<211> LENGTH: 222
<212> TYPE: PRT
<213> ORGANISM: Canis familiaris

<400> SEQUENCE: 7

```
Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Arg Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
```

```
                130                 135                 140
Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Ser Glu Asp
                165                 170                 175

Ser Asp Ser Thr Ala Pro Ser Thr Glu Glu Pro Glu Leu Pro Pro Asp
                180                 185                 190

Gln Glu Ile Ile Ala Ser Thr Met Ala Asp Val Val Thr Thr Val Met
                195                 200                 205

Gly Ser Ser Gln Pro Val Val Thr Arg Gly Thr Ala Asp Asn
    210                 215                 220
```

<210> SEQ ID NO 8
<211> LENGTH: 666
<212> TYPE: DNA
<213> ORGANISM: Canis familiaris

<400> SEQUENCE: 8

```
aaggaggcat gtcccactgg cctgtacacc cacagcggcg agtgctgcaa agcctgcaat      60
ctgggtgagg gggtggccca gccttgcgga gccaaccaga ccgtgtgtga gccctgcctg     120
gacagcgtga ccttctcgga cgtggtgagc gccaccgagc cgtgcaagcc gtgcaccgag     180
tgcgtggggc tgcagagcat gtcggcgccg tgcgtggagg cggacgacgc cgtgtgccgc     240
tgcgcctacg gctactacca ggacgagacg acgggccgct gcgaggcgtg ccgcgtgtgc     300
gaggcgggct cggggctcgt gttctcgtgc caggacaggc agaacaccgt gtgcgaggag     360
tgtcccgacg gcacgtactc cgacgaggcc aaccacgtgg accgtgcct gccctgcacc      420
gtgtgcgagg acaccgagcg ccagctgcgc gagtgcacgc gctgggccga cgccgagtgc     480
gaggagatcc ctggccgttg gattacccgg tccacaccct cagaggactc ggacagcacc     540
gcccccagca cagaggagcc agagctacct ccagatcaag aaatcatagc cagcaccatg     600
gcagatgtgg tgaccacagt gatgggcagc tctcagcctg tagtgacccg aggaaccgct     660
gacaac                                                                666
```

<210> SEQ ID NO 9
<211> LENGTH: 42
<212> TYPE: PRT
<213> ORGANISM: Canis familiaris

<400> SEQUENCE: 9

```
Trp Ile Thr Arg Ser Thr Pro Ser Glu Asp Ser Asp Ser Thr Ala Pro
1               5                  10                  15

Ser Thr Glu Glu Pro Glu Leu Pro Pro Asp Gln Glu Ile Ile Ala Ser
                20                  25                  30

Thr Met Ala Asp Val Val Thr Thr Val Met
                35                  40
```

<210> SEQ ID NO 10
<211> LENGTH: 126
<212> TYPE: DNA
<213> ORGANISM: Canis familiaris

<400> SEQUENCE: 10

```
tggattaccc ggtccacacc ctcagaggac tcggacagca ccgcccccag cacagaggag      60
ccagagctac tccagatca agaaatcata gccagcacca tggcagatgt ggtgaccaca     120
gtgatg                                                                126
```

<210> SEQ ID NO 11
<211> LENGTH: 422
<212> TYPE: PRT
<213> ORGANISM: Canis familiaris

<400> SEQUENCE: 11

```
Met Glu Trp Ser Trp Val Phe Leu Phe Phe Leu Ser Val Thr Thr Gly
1               5                   10                  15

Val His Ser Lys Glu Ala Cys Pro Thr Gly Leu Tyr Thr His Ser Gly
            20                  25                  30

Glu Cys Cys Lys Ala Cys Asn Leu Gly Glu Gly Val Ala Gln Pro Cys
        35                  40                  45

Gly Ala Asn Gln Thr Val Cys Glu Pro Cys Leu Asp Ser Val Thr Phe
    50                  55                  60

Ser Asp Val Val Ser Ala Thr Glu Pro Cys Lys Pro Cys Thr Glu Cys
65                  70                  75                  80

Val Gly Leu Gln Ser Met Ser Ala Pro Cys Val Glu Ala Asp Asp Ala
                85                  90                  95

Val Cys Arg Cys Ala Tyr Gly Tyr Tyr Gln Asp Glu Thr Thr Gly Arg
            100                 105                 110

Cys Glu Ala Cys Arg Val Cys Glu Ala Gly Ser Gly Leu Val Phe Ser
        115                 120                 125

Cys Gln Asp Arg Gln Asn Thr Val Cys Glu Glu Cys Pro Asp Gly Thr
    130                 135                 140

Tyr Ser Asp Glu Ala Asn His Val Asp Pro Cys Leu Pro Cys Thr Val
145                 150                 155                 160

Cys Glu Asp Thr Glu Arg Gln Leu Arg Glu Cys Thr Arg Trp Ala Asp
                165                 170                 175

Ala Glu Cys Glu Glu Ile Pro Gly Gly Gly Arg Glu Asn Gly Arg
            180                 185                 190

Val Pro Arg Pro Pro Asp Cys Pro Lys Cys Pro Ala Pro Glu Met Leu
        195                 200                 205

Gly Gly Pro Ser Val Phe Ile Phe Pro Pro Lys Pro Lys Asp Thr Leu
    210                 215                 220

Leu Ile Ala Arg Thr Pro Glu Val Thr Cys Val Val Val Asp Leu Asp
225                 230                 235                 240

Pro Glu Asp Pro Glu Val Gln Ile Ser Trp Phe Val Asp Gly Lys Gln
                245                 250                 255

Met Gln Thr Ala Lys Thr Gln Pro Arg Glu Glu Gln Phe Asn Gly Thr
            260                 265                 270

Tyr Arg Val Val Ser Val Leu Pro Ile Gly His Gln Asp Trp Leu Lys
        275                 280                 285

Gly Lys Gln Phe Thr Cys Lys Val Asn Asn Lys Ala Leu Pro Ser Pro
    290                 295                 300

Ile Glu Arg Thr Ile Ser Lys Ala Arg Gly Gln Ala His Gln Pro Ser
305                 310                 315                 320

Val Tyr Val Leu Pro Pro Ser Arg Glu Glu Leu Ser Lys Asn Thr Val
                325                 330                 335

Ser Leu Thr Cys Leu Ile Lys Asp Phe Phe Pro Pro Asp Ile Asp Val
            340                 345                 350

Glu Trp Gln Ser Asn Gly Gln Gln Glu Pro Glu Ser Lys Tyr Arg Thr
        355                 360                 365

Thr Pro Pro Gln Leu Asp Glu Asp Gly Ser Tyr Phe Leu Tyr Ser Lys
```

```
Leu Ser Val Asp Lys Ser Arg Trp Gln Arg Gly Asp Thr Phe Ile Cys
385                 390                 395                 400

Ala Val Met His Glu Ala Leu His Asn His Tyr Thr Gln Lys Ser Leu
                405                 410                 415

Ser His Ser Pro Gly Lys
            420
```

<210> SEQ ID NO 12
<211> LENGTH: 1269
<212> TYPE: DNA
<213> ORGANISM: Canis familiaris

<400> SEQUENCE: 12

```
atggaatggt cctgggtgtt cctgttcttc ctgtccgtga ccaccggcgt gcactccaaa      60
gaggcttgtc ctaccggcct gtacacccac tctggcgagt gttgcaaggc tgtaatctc     120
ggcgaaggcg tggcacaacc ttgtggcgct aatcagacag tgtgcgagcc ttgcctggac    180
tccgtgacct tctctgatgt ggtgtctgcc accgagccat gcaagccttg taccgagtgt    240
gtgggcctgc agtccatgtc tgccccttgt gtggaagccg acgacgccgt gtgtagatgt    300
gcctacggct actaccagga cgagacaacc ggaagatgcg aggcctgcag agtgtgtgaa    360
gctggctctg actggtgtt ctcctgccaa gacagacaga acaccgtgtg cgaggaatgc    420
cctgacggca cctactctga tgaggccaat cacgtggacc cctgcctgcc ttgtactgtg    480
tgcgaagata ccgagcggca gctgcgcgag tgtaccagat gggctgatgc cgagtgcgaa    540
gagatccctg aggtggcgg acgcgagaat ggcagagtgc ctagacctcc tgactgccct    600
aagtgccctg ctcctgaaat gctcggcgga ccctccgtgt tcatcttccc acctaagcct    660
aaggacaccc tgctgatcgc tcggacccct gaagtgacat gcgtggtggt ggatctggac    720
cccgaggatc ctgaggtgca gatcagttgg ttcgtggacg gcaagcagat gcagaccgct    780
aagacccagc ctagagagga acagttcaac ggcacctaca gagtggtgtc tgtgctgcct    840
atcggccacc aggattggct gaagggcaag cagtttacct gcaaagtgaa caacaaggcc    900
ctgccttctc aatcgagcg gaccatctct aaggccagag ccaggctca tcagccttcc    960
gtgtatgtcc tgccacctag ccgcgaggaa ctgtccaaga caccgtgtc tctgacctgc   1020
ctgatcaagg acttcttccc tcctgacatc gacgtggaat ggcagtccaa cggccagcaa   1080
gagcccgagt ctaagtaccg gacaaccct ccacagctgg acgaggacgg ctcctacttc   1140
ctgtactcca gctgtccgt ggacaagtct cggtggcaga gaggcgacac cttcatctgt   1200
gctgtgatgc acgaggccct gcacaaccac tacacccaga gtccctgtc tcactcccct   1260
ggcaagtga                                                         1269
```

<210> SEQ ID NO 13
<211> LENGTH: 422
<212> TYPE: PRT
<213> ORGANISM: Canis familiaris

<400> SEQUENCE: 13

```
Met Glu Trp Ser Trp Val Phe Leu Phe Phe Leu Ser Val Thr Thr Gly
1               5                   10                  15

Val His Ser Lys Glu Ala Cys Pro Thr Gly Leu Tyr Thr His Ser Gly
            20                  25                  30

Glu Cys Cys Lys Ala Cys Asn Leu Gly Glu Gly Val Ala Gln Pro Cys
        35                  40                  45
```

Gly Ala Asn Gln Thr Val Cys Glu Pro Cys Leu Asp Ser Val Thr Phe
 50                  55                  60

Ser Asp Val Val Ser Ala Thr Glu Pro Cys Lys Pro Cys Thr Glu Cys
 65                  70                  75                  80

Val Gly Leu Gln Ser Met Ser Ala Pro Cys Val Glu Ala Asp Asp Ala
                     85                  90                  95

Val Cys Arg Cys Ala Tyr Gly Tyr Gln Asp Glu Thr Thr Gly Arg
                100                 105                 110

Cys Glu Ala Cys Arg Val Cys Glu Ala Gly Ser Gly Leu Val Phe Ser
            115                 120                 125

Cys Gln Asp Arg Gln Asn Thr Val Cys Glu Glu Cys Pro Asp Gly Thr
        130                 135                 140

Tyr Ser Asp Glu Ala Asn His Val Asp Pro Cys Leu Pro Cys Thr Val
145                 150                 155                 160

Cys Glu Asp Thr Glu Arg Gln Leu Arg Glu Cys Thr Arg Trp Ala Asp
                165                 170                 175

Ala Glu Cys Glu Glu Ile Pro Gly Gly Gly Arg Glu Asn Gly Arg
                180                 185                 190

Val Pro Arg Pro Pro Asp Cys Pro Lys Cys Pro Ala Pro Glu Met Leu
        195                 200                 205

Gly Gly Pro Ser Val Phe Ile Phe Pro Pro Lys Pro Lys Asp Thr Leu
    210                 215                 220

Tyr Ile Thr Arg Glu Pro Glu Val Thr Cys Val Val Asp Leu Asp
225                 230                 235                 240

Pro Glu Asp Pro Glu Val Gln Ile Ser Trp Phe Val Asp Gly Lys Gln
                245                 250                 255

Met Gln Thr Ala Lys Thr Gln Pro Arg Glu Glu Gln Phe Asn Gly Thr
            260                 265                 270

Tyr Arg Val Val Ser Val Leu Pro Ile Gly His Gln Asp Trp Leu Lys
        275                 280                 285

Gly Lys Gln Phe Thr Cys Lys Val Asn Asn Lys Ala Leu Pro Ser Pro
    290                 295                 300

Ile Glu Arg Thr Ile Ser Lys Ala Arg Gly Gln Ala His Gln Pro Ser
305                 310                 315                 320

Val Tyr Val Leu Pro Pro Ser Arg Glu Glu Leu Ser Lys Asn Thr Val
                325                 330                 335

Ser Leu Thr Cys Leu Ile Lys Asp Phe Phe Pro Pro Asp Ile Asp Val
            340                 345                 350

Glu Trp Gln Ser Asn Gly Gln Gln Glu Pro Glu Ser Lys Tyr Arg Thr
        355                 360                 365

Thr Pro Pro Gln Leu Asp Glu Asp Gly Ser Tyr Phe Leu Tyr Ser Lys
    370                 375                 380

Leu Ser Val Asp Lys Ser Arg Trp Gln Arg Gly Asp Thr Phe Ile Cys
385                 390                 395                 400

Ala Val Met His Glu Ala Leu His Asn His Tyr Thr Gln Lys Ser Leu
                405                 410                 415

Ser His Ser Pro Gly Lys
            420

<210> SEQ ID NO 14
<211> LENGTH: 1269
<212> TYPE: DNA
<213> ORGANISM: Canis familiaris

<400> SEQUENCE: 14

```
atggaatggt cctgggtgtt cctgttcttc ctgtccgtga ccaccggcgt gcactccaaa    60
gaggcttgtc ctaccggcct gtacacccac tctggcgagt gttgcaaggc ctgtaatctc   120
ggcgaaggcg tggcacaacc ttgtggcgct aatcagacag tgtgcgagcc ttgcctggac   180
tccgtgacct tctctgatgt ggtgtctgcc accgagccat gcaagccttg taccgagtgt   240
gtgggcctgc agtccatgtc tgccccttgt gtggaagccg acgacgccgt gtgtagatgt   300
gcctacggct actaccagga cgagacaacc ggaagatgcg aggcctgcag agtgtgtgaa   360
gctggctctg gactggtgtt ctcctgccaa gacagacaga caccgtgtg cgaggaatgc   420
cctgacggca cctactctga tgaggccaat cacgtggacc cctgcctgcc ttgtactgtg   480
tgcgaagata ccgagcggca gctgcgcgag tgtaccagat gggctgatgc cgagtgcgaa   540
gagatccctg aggtggcgg acgcgagaat ggcagagtgc ctagacctcc tgactgccct   600
aagtgccctg ctcctgaaat gctcggcgga ccctccgtgt tcatcttccc acctaagcct   660
aaggacaccc tgtatatcac tcgggaacct gaagtgacat gcgtggtggt ggatctggac   720
cccgaggatc ctgaggtgca gatcagttgg ttcgtggacg gcaagcagat gcagaccgct   780
aagacccagc ctagagagga acagttcaac ggcacctaca gagtggtgtc tgtgctgcct   840
atcggccacc aggattggct gaagggcaag cagtttacct gcaaagtgaa caacaaggcc   900
ctgccttctc caatcgagcg gaccatctct aaggccagag ccaggctca tcagccttcc   960
gtgtatgtcc tgccacctag ccgcgaggaa ctgtccaaga acaccgtgtc tctgacctgc  1020
ctgatcaagg acttcttccc tcctgacatc gacgtggaat ggcagtccaa cggccagcaa  1080
gagcccgagt ctaagtaccg acaaccccct ccacagctgg acgaggacgg ctcctacttc  1140
ctgtactcca gctgtccgt ggacaagtct cggtggcaga gaggcgacac cttcatctgt  1200
gctgtgatgc acgaggccct gcacaaccac tacacccaga gtccctgtc tcactcccct  1260
ggcaagtga                                                          1269
```

<210> SEQ ID NO 15
<211> LENGTH: 471
<212> TYPE: PRT
<213> ORGANISM: Canis familiaris

<400> SEQUENCE: 15

```
Met Glu Phe Val Leu Gly Trp Val Phe Leu Val Ala Ile Leu Gln Gly
1               5                   10                  15

Val Gln Gly Glu Val Gln Leu Val Glu Ser Gly Gly Asp Leu Val Lys
            20                  25                  30

Pro Ala Gly Ser Leu Arg Leu Ser Cys Val Ala Ser Gly Phe Thr Phe
        35                  40                  45

Ser Asn Asn Ala Met Asn Trp Val Arg Gln Ala Pro Gly Lys Gly Leu
    50                  55                  60

Gln Trp Val Ala Gly Ile Asn Ser Gly Gly Ser Thr Ala Ser Ala Asp
65                  70                  75                  80

Ala Val Lys Gly Arg Phe Thr Ile Ser Arg Asp Asn Ala Lys Asn Thr
                85                  90                  95

Val Tyr Leu Gln Met Asn Ser Leu Thr Ala Glu Asp Thr Ala Val Tyr
            100                 105                 110

Tyr Cys Ala Lys Val Ile Gly Asn Trp Ile Ala Thr Ser Asp Leu Asp
        115                 120                 125

Tyr Trp Gly Gln Gly Thr Leu Val Ile Val Ser Ser Ala Ser Thr Thr
```

```
            130                 135                 140
Ala Pro Ser Val Phe Pro Leu Ala Pro Ser Cys Gly Ser Thr Ser Gly
145                 150                 155                 160

Ser Thr Val Ala Leu Ala Cys Leu Val Ser Gly Tyr Phe Pro Glu Pro
                165                 170                 175

Val Thr Val Ser Trp Asn Ser Gly Leu Thr Ser Gly Val His Thr
            180                 185                 190

Phe Pro Ser Val Leu Gln Ser Ser Gly Leu Tyr Ser Leu Ser Ser Met
                195                 200                 205

Val Thr Val Pro Ser Ser Arg Trp Pro Ser Glu Thr Phe Thr Cys Asn
            210                 215                 220

Val Val His Pro Ala Ser Asn Thr Lys Val Asp Lys Pro Val Phe Asn
225                 230                 235                 240

Glu Cys Arg Cys Thr Asp Thr Pro Pro Cys Pro Val Pro Glu Pro Leu
                245                 250                 255

Gly Gly Pro Ser Val Leu Ile Phe Pro Pro Lys Pro Lys Asp Ile Leu
                260                 265                 270

Arg Ile Thr Arg Thr Pro Glu Val Thr Cys Val Val Leu Asp Leu Gly
            275                 280                 285

Arg Glu Asp Pro Glu Val Gln Ile Ser Trp Phe Val Asp Gly Lys Glu
290                 295                 300

Val His Thr Ala Lys Thr Gln Ser Arg Glu Gln Gln Phe Asn Gly Thr
305                 310                 315                 320

Tyr Arg Val Val Ser Val Leu Pro Ile Glu His Gln Asp Trp Leu Thr
                325                 330                 335

Gly Lys Glu Phe Lys Cys Arg Val Asn His Ile Asp Leu Pro Ser Pro
                340                 345                 350

Ile Glu Arg Thr Ile Ser Lys Ala Arg Gly Arg Ala His Lys Pro Ser
            355                 360                 365

Val Tyr Val Leu Pro Pro Ser Pro Lys Glu Leu Ser Ser Ser Asp Thr
            370                 375                 380

Val Ser Ile Thr Cys Leu Ile Lys Asp Phe Tyr Pro Pro Asp Ile Asp
385                 390                 395                 400

Val Glu Trp Gln Ser Asn Gly Gln Gln Glu Pro Glu Arg Lys His Arg
                405                 410                 415

Met Thr Pro Pro Gln Leu Asp Glu Asp Gly Ser Tyr Phe Leu Tyr Ser
                420                 425                 430

Lys Leu Ser Val Asp Lys Ser Arg Trp Gln Gln Gly Asp Pro Phe Thr
            435                 440                 445

Cys Ala Val Met His Glu Thr Leu Gln Asn His Tyr Thr Asp Leu Ser
450                 455                 460

Leu Ser His Ser Pro Gly Lys
465                 470

<210> SEQ ID NO 16
<211> LENGTH: 475
<212> TYPE: PRT
<213> ORGANISM: Canis familiaris

<400> SEQUENCE: 16

Met Glu Phe Val Leu Gly Trp Val Phe Leu Val Ala Ile Leu Gln Gly
1               5                   10                  15

Val Gln Gly Glu Val Gln Leu Val Glu Ser Gly Gly Asp Leu Val Lys
            20                  25                  30
```

-continued

```
Pro Ala Gly Ser Leu Arg Leu Ser Cys Val Ala Ser Gly Phe Thr Phe
            35                  40                  45
Ser Asn Asn Ala Met Asn Trp Val Arg Gln Ala Pro Gly Lys Gly Leu
 50                  55                  60
Gln Trp Val Ala Gly Ile Asn Ser Gly Gly Ser Thr Ala Ser Ala Asp
 65                  70                  75                  80
Ala Val Lys Gly Arg Phe Thr Ile Ser Arg Asp Asn Ala Lys Asn Thr
                 85                  90                  95
Val Tyr Leu Gln Met Asn Ser Leu Thr Ala Glu Asp Thr Ala Val Tyr
                100                 105                 110
Tyr Cys Ala Lys Val Ile Gly Asn Trp Ile Ala Thr Ser Asp Leu Asp
            115                 120                 125
Tyr Trp Gly Gln Gly Thr Leu Val Ile Val Ser Ser Ala Ser Thr Thr
130                 135                 140
Ala Pro Ser Val Phe Pro Leu Ala Pro Ser Cys Gly Ser Thr Ser Gly
145                 150                 155                 160
Ser Thr Val Ala Leu Ala Cys Leu Val Ser Gly Tyr Phe Pro Glu Pro
                165                 170                 175
Val Thr Val Ser Trp Asn Ser Gly Ser Leu Thr Ser Gly Val His Thr
            180                 185                 190
Phe Pro Ser Val Leu Gln Ser Ser Gly Leu Tyr Ser Leu Ser Ser Met
        195                 200                 205
Val Thr Val Pro Ser Ser Arg Trp Pro Ser Glu Thr Phe Thr Cys Asn
            210                 215                 220
Val Ala His Pro Ala Ser Lys Thr Lys Val Asp Lys Pro Val Pro Lys
225                 230                 235                 240
Arg Glu Asn Gly Arg Val Pro Arg Pro Pro Asp Cys Pro Lys Cys Pro
                245                 250                 255
Ala Pro Glu Met Leu Gly Gly Pro Ser Val Phe Ile Phe Pro Pro Lys
            260                 265                 270
Pro Lys Asp Thr Leu Leu Ile Ala Arg Thr Pro Glu Val Thr Cys Val
        275                 280                 285
Val Val Asp Leu Asp Pro Glu Asp Pro Glu Val Gln Ile Ser Trp Phe
290                 295                 300
Val Asp Gly Lys Gln Met Gln Thr Ala Lys Thr Gln Pro Arg Glu Glu
305                 310                 315                 320
Gln Phe Asn Gly Thr Tyr Arg Val Val Ser Val Leu Pro Ile Gly His
                325                 330                 335
Gln Asp Trp Leu Lys Gly Lys Gln Phe Thr Cys Lys Val Asn Asn Lys
            340                 345                 350
Ala Leu Pro Ser Pro Ile Glu Arg Thr Ile Ser Lys Ala Arg Gly Gln
        355                 360                 365
Ala His Gln Pro Ser Val Tyr Val Leu Pro Pro Ser Arg Glu Glu Leu
370                 375                 380
Ser Lys Asn Thr Val Ser Leu Thr Cys Leu Ile Lys Asp Phe Phe Pro
385                 390                 395                 400
Pro Asp Ile Asp Val Glu Trp Gln Ser Asn Gly Gln Gln Glu Pro Glu
                405                 410                 415
Ser Lys Tyr Arg Thr Thr Pro Gln Leu Asp Glu Asp Gly Ser Tyr
            420                 425                 430
Phe Leu Tyr Ser Lys Leu Ser Val Asp Lys Ser Arg Trp Gln Arg Gly
        435                 440                 445
Asp Thr Phe Ile Cys Ala Val Met His Glu Ala Leu His Asn His Tyr
```

```
                450             455             460
Thr Gln Lys Ser Leu Ser His Ser Pro Gly Lys
465                 470                 475

<210> SEQ ID NO 17
<211> LENGTH: 473
<212> TYPE: PRT
<213> ORGANISM: Canis familiaris

<400> SEQUENCE: 17

Met Glu Phe Val Leu Gly Trp Val Phe Leu Val Ala Ile Leu Gln Gly
1               5                   10                  15

Val Gln Gly Glu Val Gln Leu Val Glu Ser Gly Gly Asp Leu Val Lys
            20                  25                  30

Pro Ala Gly Ser Leu Arg Leu Ser Cys Val Ala Ser Gly Phe Thr Phe
        35                  40                  45

Ser Asn Asn Ala Met Asn Trp Val Arg Gln Ala Pro Gly Lys Gly Leu
    50                  55                  60

Gln Trp Val Ala Gly Ile Asn Ser Gly Gly Ser Thr Ala Ser Ala Asp
65                  70                  75                  80

Ala Val Lys Gly Arg Phe Thr Ile Ser Arg Asp Asn Ala Lys Asn Thr
                85                  90                  95

Val Tyr Leu Gln Met Asn Ser Leu Thr Ala Glu Asp Thr Ala Val Tyr
            100                 105                 110

Tyr Cys Ala Lys Val Ile Gly Asn Trp Ile Ala Thr Ser Asp Leu Asp
        115                 120                 125

Tyr Trp Gly Gln Gly Thr Leu Val Ile Val Ser Ser Ala Ser Thr Thr
    130                 135                 140

Ala Pro Ser Val Phe Pro Leu Ala Pro Ser Cys Gly Ser Gln Ser Gly
145                 150                 155                 160

Ser Thr Val Ala Leu Ala Cys Leu Val Ser Gly Tyr Ile Pro Glu Pro
                165                 170                 175

Val Thr Val Ser Trp Asn Ser Gly Ser Leu Thr Ser Gly Val His Thr
            180                 185                 190

Phe Pro Ser Ile Leu Gln Ser Ser Gly Leu Tyr Ser Leu Ser Ser Met
        195                 200                 205

Val Thr Val Pro Ser Ser Arg Trp Pro Ser Glu Thr Phe Thr Cys Asn
    210                 215                 220

Val Ala His Pro Ala Thr Asn Thr Lys Val Asp Lys Pro Val Val Lys
225                 230                 235                 240

Glu Cys Glu Cys Lys Cys Asn Cys Asn Asn Cys Pro Cys Pro Gly Cys
                245                 250                 255

Gly Leu Leu Gly Gly Pro Ser Val Phe Ile Phe Pro Pro Lys Pro Lys
            260                 265                 270

Asp Ile Leu Val Thr Ala Arg Thr Pro Thr Val Thr Cys Val Val Val
        275                 280                 285

Asp Leu Asp Pro Glu Asn Pro Glu Val Gln Ile Ser Trp Phe Val Asp
    290                 295                 300

Ser Lys Gln Val Gln Thr Ala Asn Thr Gln Pro Arg Glu Glu Gln Ser
305                 310                 315                 320

Asn Gly Thr Tyr Arg Val Val Ser Val Leu Pro Ile Gly His Gln Asp
                325                 330                 335

Trp Leu Ser Gly Lys Gln Phe Lys Cys Lys Val Asn Asn Lys Ala Leu
            340                 345                 350
```

Pro Ser Pro Ile Glu Glu Ile Ile Ser Lys Thr Pro Gly Gln Ala His
           355                 360                 365

Gln Pro Asn Val Tyr Val Leu Pro Pro Ser Arg Asp Glu Met Ser Lys
    370                 375                 380

Asn Thr Val Thr Leu Thr Cys Leu Val Lys Asp Phe Phe Pro Pro Glu
385                 390                 395                 400

Ile Asp Val Glu Trp Gln Ser Asn Gly Gln Gln Pro Glu Ser Lys
                405                 410                 415

Tyr Arg Met Thr Pro Pro Gln Leu Asp Glu Asp Gly Ser Tyr Phe Leu
            420                 425                 430

Tyr Ser Lys Leu Ser Val Asp Lys Ser Arg Trp Gln Arg Gly Asp Thr
            435                 440                 445

Phe Ile Cys Ala Val Met His Glu Ala Leu His Asn His Tyr Thr Gln
450                 455                 460

Lys Ser Leu Ser His Ser Pro Gly Lys
465                 470

<210> SEQ ID NO 18
<211> LENGTH: 471
<212> TYPE: PRT
<213> ORGANISM: Canis familiaris

<400> SEQUENCE: 18

Met Glu Phe Val Leu Gly Trp Val Phe Leu Val Ala Ile Leu Gln Gly
1               5                   10                  15

Val Gln Gly Glu Val Gln Leu Val Glu Ser Gly Gly Asp Leu Val Lys
            20                  25                  30

Pro Ala Gly Ser Leu Arg Leu Ser Cys Val Ala Ser Gly Phe Thr Phe
        35                  40                  45

Ser Asn Asn Ala Met Asn Trp Val Arg Gln Ala Pro Lys Gly Leu
    50                  55                  60

Gln Trp Val Ala Gly Ile Asn Ser Gly Gly Ser Thr Ala Ser Ala Asp
65                  70                  75                  80

Ala Val Lys Gly Arg Phe Thr Ile Ser Arg Asp Asn Ala Lys Asn Thr
                85                  90                  95

Val Tyr Leu Gln Met Asn Ser Leu Thr Ala Glu Asp Thr Ala Val Tyr
            100                 105                 110

Tyr Cys Ala Lys Val Ile Gly Asn Trp Ile Ala Thr Ser Asp Leu Asp
        115                 120                 125

Tyr Trp Gly Gln Gly Thr Leu Val Ile Val Ser Ser Ala Ser Ser Thr
    130                 135                 140

Ala Pro Ser Val Phe Pro Leu Ala Pro Ser Cys Gly Ser Thr Ser Gly
145                 150                 155                 160

Ser Thr Val Ala Leu Ala Cys Leu Val Ser Gly Tyr Phe Pro Glu Pro
                165                 170                 175

Val Thr Val Ser Trp Asn Ser Gly Ser Leu Thr Ser Gly Val His Thr
            180                 185                 190

Phe Pro Ser Val Leu Lys Ser Ser Gly Leu Tyr Ser Leu Ser Ser Met
        195                 200                 205

Val Thr Val Pro Ser Ser Arg Leu Pro Ser Glu Thr Phe Thr Cys Asn
    210                 215                 220

Val Val His Pro Ala Thr Asn Thr Lys Val Asp Lys Pro Val Pro Lys
225                 230                 235                 240

Glu Ser Thr Cys Lys Cys Ile Ser Pro Cys Pro Val Pro Glu Ser Leu
                245                 250                 255

```
Gly Gly Pro Ser Val Phe Ile Phe Pro Pro Lys Pro Lys Asp Ile Leu
            260                 265                 270

Arg Ile Thr Arg Thr Pro Glu Val Thr Cys Val Val Leu Asp Leu Gly
            275                 280                 285

Arg Glu Asp Pro Glu Val Gln Ile Ser Trp Phe Val Asp Gly Lys Glu
290                 295                 300

Val His Thr Ala Lys Thr Gln Pro Arg Glu Gln Gln Phe Asn Ser Thr
305                 310                 315                 320

Tyr Arg Val Val Ser Val Leu Pro Ile Glu His Gln Asp Trp Leu Thr
                325                 330                 335

Gly Lys Glu Phe Lys Cys Arg Val Asn His Ile Gly Leu Pro Ser Pro
            340                 345                 350

Ile Glu Arg Thr Ile Ser Lys Ala Arg Gly Gln Ala His Gln Pro Gly
            355                 360                 365

Val Tyr Val Leu Pro Pro Ser Pro Lys Glu Leu Ser Ser Ser Asp Thr
            370                 375                 380

Val Thr Leu Thr Cys Leu Ile Lys Asp Phe Phe Pro Pro Glu Ile Asp
385                 390                 395                 400

Val Glu Trp Gln Ser Asn Gly Gln Pro Glu Pro Glu Ser Lys Tyr His
                405                 410                 415

Thr Thr Ala Pro Gln Leu Asp Glu Asp Gly Ser Tyr Phe Leu Tyr Ser
            420                 425                 430

Lys Leu Ser Val Asp Lys Ser Arg Trp Gln Gln Gly Asp Pro Phe Thr
            435                 440                 445

Cys Ala Val Met His Glu Ala Leu Gln Asn His Tyr Thr Asp Leu Ser
            450                 455                 460

Leu Ser His Ser Pro Gly Lys
465                 470

<210> SEQ ID NO 19
<211> LENGTH: 233
<212> TYPE: PRT
<213> ORGANISM: Canis familiaris

<400> SEQUENCE: 19

Phe Asn Glu Cys Arg Cys Thr Asp Thr Pro Pro Cys Pro Val Pro Glu
1               5                   10                  15

Pro Leu Gly Gly Pro Ser Val Leu Ile Phe Pro Pro Lys Pro Lys Asp
                20                  25                  30

Ile Leu Arg Ile Thr Arg Thr Pro Glu Val Thr Cys Val Val Leu Asp
            35                  40                  45

Leu Gly Arg Glu Asp Pro Glu Val Gln Ile Ser Trp Phe Val Asp Gly
        50                  55                  60

Lys Glu Val His Thr Ala Lys Thr Gln Ser Arg Glu Gln Gln Phe Asn
65                  70                  75                  80

Gly Thr Tyr Arg Val Val Ser Val Leu Pro Ile Glu His Gln Asp Trp
                85                  90                  95

Leu Thr Gly Lys Glu Phe Lys Cys Arg Val Asn His Ile Asp Leu Pro
            100                 105                 110

Ser Pro Ile Glu Arg Thr Ile Ser Lys Ala Arg Gly Arg Ala His Lys
            115                 120                 125

Pro Ser Val Tyr Val Leu Pro Pro Ser Pro Lys Glu Leu Ser Ser Ser
        130                 135                 140

Asp Thr Val Ser Ile Thr Cys Leu Ile Lys Asp Phe Tyr Pro Pro Asp
```

```
                145                 150                 155                 160
Ile Asp Val Glu Trp Gln Ser Asn Gly Gln Gln Glu Pro Arg Lys
                165                 170                 175

His Arg Met Thr Pro Pro Gln Leu Asp Glu Asp Gly Ser Tyr Phe Leu
                180                 185                 190

Tyr Ser Lys Leu Ser Val Asp Lys Ser Arg Trp Gln Gln Gly Asp Pro
                195                 200                 205

Phe Thr Cys Ala Val Met His Glu Thr Leu Gln Asn His Tyr Thr Asp
                210                 215                 220

Leu Ser Leu Ser His Ser Pro Gly Lys
225                 230
```

<210> SEQ ID NO 20
<211> LENGTH: 235
<212> TYPE: PRT
<213> ORGANISM: Canis familiaris

<400> SEQUENCE: 20

```
Arg Glu Asn Gly Arg Val Pro Arg Pro Pro Asp Cys Pro Lys Cys Pro
1               5                   10                  15

Ala Pro Glu Met Leu Gly Gly Pro Ser Val Phe Ile Phe Pro Pro Lys
                20                  25                  30

Pro Lys Asp Thr Leu Leu Ile Ala Arg Thr Pro Glu Val Thr Cys Val
                35                  40                  45

Val Val Asp Leu Asp Pro Glu Asp Pro Glu Val Gln Ile Ser Trp Phe
        50                  55                  60

Val Asp Gly Lys Gln Met Gln Thr Ala Lys Thr Gln Pro Arg Glu Glu
65                  70                  75                  80

Gln Phe Asn Gly Thr Tyr Arg Val Val Ser Val Leu Pro Ile Gly His
                85                  90                  95

Gln Asp Trp Leu Lys Gly Lys Gln Phe Thr Cys Lys Val Asn Asn Lys
                100                 105                 110

Ala Leu Pro Ser Pro Ile Glu Arg Thr Ile Ser Lys Ala Arg Gly Gln
                115                 120                 125

Ala His Gln Pro Ser Val Tyr Val Leu Pro Pro Ser Arg Glu Glu Leu
        130                 135                 140

Ser Lys Asn Thr Val Ser Leu Thr Cys Leu Ile Lys Asp Phe Phe Pro
145                 150                 155                 160

Pro Asp Ile Asp Val Glu Trp Gln Ser Asn Gly Gln Gln Glu Pro Glu
                165                 170                 175

Ser Lys Tyr Arg Thr Thr Pro Pro Gln Leu Asp Glu Asp Gly Ser Tyr
                180                 185                 190

Phe Leu Tyr Ser Lys Leu Ser Val Asp Lys Ser Arg Trp Gln Arg Gly
                195                 200                 205

Asp Thr Phe Ile Cys Ala Val Met His Glu Ala Leu His Asn His Tyr
        210                 215                 220

Thr Gln Lys Ser Leu Ser His Ser Pro Gly Lys
225                 230                 235
```

<210> SEQ ID NO 21
<211> LENGTH: 235
<212> TYPE: PRT
<213> ORGANISM: Canis familiaris

<400> SEQUENCE: 21

Arg Glu Asn Gly Arg Val Pro Arg Pro Pro Asp Cys Pro Lys Cys Pro

```
            1               5                  10                 15
         Ala Pro Glu Met Leu Gly Gly Pro Ser Val Phe Ile Phe Pro Pro Lys
                        20                 25                 30

Pro Lys Asp Thr Leu Tyr Ile Thr Arg Glu Pro Glu Val Thr Cys Val
                        35                 40                 45

Val Val Asp Leu Asp Pro Glu Asp Pro Glu Val Gln Ile Ser Trp Phe
                        50                 55                 60

Val Asp Gly Lys Gln Met Gln Thr Ala Lys Thr Gln Pro Arg Glu Glu
         65                 70                 75                 80

Gln Phe Asn Gly Thr Tyr Arg Val Val Ser Val Leu Pro Ile Gly His
                        85                 90                 95

Gln Asp Trp Leu Lys Gly Lys Gln Phe Thr Cys Lys Val Asn Asn Lys
                        100                105                110

Ala Leu Pro Ser Pro Ile Glu Arg Thr Ile Ser Lys Ala Arg Gly Gln
                        115                120                125

Ala His Gln Pro Ser Val Tyr Val Leu Pro Pro Ser Arg Glu Glu Leu
                        130                135                140

Ser Lys Asn Thr Val Ser Leu Thr Cys Leu Ile Lys Asp Phe Phe Pro
         145                150                155                160

Pro Asp Ile Asp Val Glu Trp Gln Ser Asn Gly Gln Gln Glu Pro Glu
                        165                170                175

Ser Lys Tyr Arg Thr Thr Pro Pro Gln Leu Asp Glu Asp Gly Ser Tyr
                        180                185                190

Phe Leu Tyr Ser Lys Leu Ser Val Asp Lys Ser Arg Trp Gln Arg Gly
                        195                200                205

Asp Thr Phe Ile Cys Ala Val Met His Glu Ala Leu His Asn His Tyr
                        210                215                220

Thr Gln Lys Ser Leu Ser His Ser Pro Gly Lys
         225                230                235

<210> SEQ ID NO 22
<211> LENGTH: 233
<212> TYPE: PRT
<213> ORGANISM: Canis familiaris

<400> SEQUENCE: 22

Glu Cys Glu Cys Lys Cys Asn Cys Asn Asn Cys Pro Cys Pro Gly Cys
         1                  5                  10                 15

Gly Leu Leu Gly Gly Pro Ser Val Phe Ile Phe Pro Pro Lys Pro Lys
                        20                 25                 30

Asp Ile Leu Val Thr Ala Arg Thr Pro Thr Val Thr Cys Val Val Val
                        35                 40                 45

Asp Leu Asp Pro Glu Asn Pro Glu Val Gln Ile Ser Trp Phe Val Asp
                        50                 55                 60

Ser Lys Gln Val Gln Thr Ala Asn Thr Gln Pro Arg Glu Glu Gln Ser
         65                 70                 75                 80

Asn Gly Thr Tyr Arg Val Val Ser Val Leu Pro Ile Gly His Gln Asp
                        85                 90                 95

Trp Leu Ser Gly Lys Gln Phe Lys Cys Lys Val Asn Asn Lys Ala Leu
                        100                105                110

Pro Ser Pro Ile Glu Glu Ile Ile Ser Lys Thr Pro Gly Gln Ala His
                        115                120                125

Gln Pro Asn Val Tyr Val Leu Pro Pro Ser Arg Asp Glu Met Ser Lys
                        130                135                140
```

Asn Thr Val Thr Leu Thr Cys Leu Val Lys Asp Phe Phe Pro Pro Glu
145                 150                 155                 160

Ile Asp Val Glu Trp Gln Ser Asn Gly Gln Gln Glu Pro Glu Ser Lys
                165                 170                 175

Tyr Arg Met Thr Pro Pro Gln Leu Asp Glu Asp Gly Ser Tyr Phe Leu
            180                 185                 190

Tyr Ser Lys Leu Ser Val Asp Lys Ser Arg Trp Gln Arg Gly Asp Thr
        195                 200                 205

Phe Ile Cys Ala Val Met His Glu Ala Leu His Asn His Tyr Thr Gln
    210                 215                 220

Lys Ser Leu Ser His Ser Pro Gly Lys
225                 230

<210> SEQ ID NO 23
<211> LENGTH: 231
<212> TYPE: PRT
<213> ORGANISM: Canis familiaris

<400> SEQUENCE: 23

Glu Ser Thr Cys Lys Cys Ile Ser Pro Cys Pro Val Pro Glu Ser Leu
1               5                   10                  15

Gly Gly Pro Ser Val Phe Ile Phe Pro Pro Lys Pro Lys Asp Ile Leu
            20                  25                  30

Arg Ile Thr Arg Thr Pro Glu Val Thr Cys Val Val Leu Asp Leu Gly
        35                  40                  45

Arg Glu Asp Pro Glu Val Gln Ile Ser Trp Phe Val Asp Gly Lys Glu
    50                  55                  60

Val His Thr Ala Lys Thr Gln Pro Arg Glu Gln Gln Phe Asn Ser Thr
65                  70                  75                  80

Tyr Arg Val Val Ser Val Leu Pro Ile Glu His Gln Asp Trp Leu Thr
                85                  90                  95

Gly Lys Glu Phe Lys Cys Arg Val Asn His Ile Gly Leu Pro Ser Pro
            100                 105                 110

Ile Glu Arg Thr Ile Ser Lys Ala Arg Gly Gln Ala His Gln Pro Gly
        115                 120                 125

Val Tyr Val Leu Pro Pro Ser Pro Lys Glu Leu Ser Ser Ser Asp Thr
    130                 135                 140

Val Thr Leu Thr Cys Leu Ile Lys Asp Phe Phe Pro Pro Glu Ile Asp
145                 150                 155                 160

Val Glu Trp Gln Ser Asn Gly Gln Pro Glu Pro Glu Ser Lys Tyr His
                165                 170                 175

Thr Thr Ala Pro Gln Leu Asp Glu Asp Gly Ser Tyr Phe Leu Tyr Ser
            180                 185                 190

Lys Leu Ser Val Asp Lys Ser Arg Trp Gln Gln Gly Asp Pro Phe Thr
        195                 200                 205

Cys Ala Val Met His Glu Ala Leu Gln Asn His Tyr Thr Asp Leu Ser
    210                 215                 220

Leu Ser His Ser Pro Gly Lys
225                 230

<210> SEQ ID NO 24
<211> LENGTH: 235
<212> TYPE: PRT
<213> ORGANISM: Felis catus

<400> SEQUENCE: 24

Thr Asp His Pro Pro Gly Pro Lys Pro Cys Asp Cys Pro Lys Cys Pro
1               5                   10                  15

Pro Pro Glu Met Leu Gly Gly Pro Ser Ile Phe Ile Phe Pro Pro Lys
            20                  25                  30

Pro Lys Asp Thr Leu Ser Ile Ser Arg Thr Pro Glu Val Thr Cys Leu
        35                  40                  45

Val Val Asp Leu Gly Pro Asp Asp Ser Asp Val Gln Ile Thr Trp Phe
    50                  55                  60

Val Asp Asn Thr Gln Val Tyr Thr Ala Lys Thr Ser Pro Arg Glu Glu
65                  70                  75                  80

Gln Phe Asn Ser Thr Tyr Arg Val Val Ser Val Leu Pro Ile Leu His
                85                  90                  95

Gln Asp Trp Leu Lys Gly Lys Glu Phe Lys Cys Lys Val Asn Ser Lys
            100                 105                 110

Ser Leu Pro Ser Pro Ile Glu Arg Thr Ile Ser Lys Ala Lys Gly Gln
        115                 120                 125

Pro His Glu Pro Gln Val Tyr Val Leu Pro Pro Ala Gln Glu Glu Leu
    130                 135                 140

Ser Arg Asn Lys Val Ser Val Thr Cys Leu Ile Lys Ser Phe His Pro
145                 150                 155                 160

Pro Asp Ile Ala Val Glu Trp Glu Ile Thr Gly Gln Pro Glu Pro Glu
            165                 170                 175

Asn Asn Tyr Arg Thr Thr Pro Pro Gln Leu Asp Ser Asp Gly Thr Tyr
        180                 185                 190

Phe Val Tyr Ser Lys Leu Ser Val Asp Arg Ser His Trp Gln Arg Gly
    195                 200                 205

Asn Thr Tyr Thr Cys Ser Val Ser His Glu Ala Leu His Ser His His
    210                 215                 220

Thr Gln Lys Ser Leu Thr Gln Ser Pro Gly Lys
225                 230                 235

<210> SEQ ID NO 25
<211> LENGTH: 235
<212> TYPE: PRT
<213> ORGANISM: Felis catus

<400> SEQUENCE: 25

Thr Asp His Pro Pro Gly Pro Lys Pro Cys Asp Cys Pro Lys Cys Pro
1               5                   10                  15

Pro Pro Glu Met Leu Gly Gly Pro Ser Ile Phe Ile Phe Pro Pro Lys
            20                  25                  30

Pro Lys Asp Thr Leu Ser Ile Ser Arg Thr Pro Glu Val Thr Cys Leu
        35                  40                  45

Val Val Asp Leu Gly Pro Asp Asp Ser Asp Val Gln Ile Thr Trp Phe
    50                  55                  60

Val Asp Asn Thr Gln Val Tyr Thr Ala Lys Thr Ser Pro Arg Glu Glu
65                  70                  75                  80

Gln Phe Asn Ser Thr Tyr Arg Val Val Ser Val Leu Pro Ile Leu His
                85                  90                  95

Gln Asp Trp Leu Lys Gly Lys Glu Phe Lys Cys Lys Val Asn Ser Lys
            100                 105                 110

Ser Leu Pro Ser Pro Ile Glu Arg Thr Ile Ser Lys Ala Lys Gly Gln
        115                 120                 125

Pro His Glu Pro Gln Val Tyr Val Leu Pro Pro Ala Gln Glu Glu Leu
    130                 135                 140

```
Ser Arg Asn Lys Val Ser Val Thr Cys Leu Ile Lys Ser Phe His Pro
145                 150                 155                 160

Pro Asp Ile Ala Val Glu Trp Glu Ile Thr Gly Gln Pro Glu Pro Glu
                165                 170                 175

Asn Asn Tyr Arg Thr Thr Pro Pro Gln Leu Asp Ser Asp Gly Thr Tyr
            180                 185                 190

Phe Val Tyr Ser Lys Leu Ser Val Asp Arg Ser His Trp Gln Arg Gly
                195                 200                 205

Asn Thr Tyr Thr Cys Ser Val Ser His Glu Ala Leu His Ser His His
            210                 215                 220

Thr Gln Lys Ser Leu Thr Gln Ser Pro Gly Lys
225                 230                 235

<210> SEQ ID NO 26
<211> LENGTH: 236
<212> TYPE: PRT
<213> ORGANISM: Felis catus

<400> SEQUENCE: 26

Lys Thr Ala Ser Thr Ile Glu Ser Lys Thr Gly Glu Gly Pro Lys Cys
1               5                   10                  15

Pro Val Pro Glu Ile Pro Gly Ala Pro Ser Val Phe Ile Phe Pro Pro
                20                  25                  30

Lys Pro Lys Asp Thr Leu Ser Ile Ser Arg Thr Pro Glu Val Thr Cys
            35                  40                  45

Leu Val Val Asp Leu Gly Pro Asp Asp Ser Asn Val Gln Ile Thr Trp
        50                  55                  60

Phe Val Asp Asn Thr Glu Met His Thr Ala Lys Thr Arg Pro Arg Glu
65                  70                  75                  80

Glu Gln Phe Asn Ser Thr Tyr Arg Val Val Ser Val Leu Pro Ile Leu
                85                  90                  95

His Gln Asp Trp Leu Lys Gly Lys Glu Phe Lys Cys Lys Val Asn Ser
                100                 105                 110

Lys Ser Leu Pro Ser Ala Met Glu Arg Thr Ile Ser Lys Ala Lys Gly
            115                 120                 125

Gln Pro His Glu Pro Gln Val Tyr Val Leu Pro Pro Thr Gln Glu Glu
        130                 135                 140

Leu Ser Glu Asn Lys Val Ser Val Thr Cys Leu Ile Lys Gly Phe His
145                 150                 155                 160

Pro Pro Asp Ile Ala Val Glu Trp Glu Ile Thr Gly Gln Pro Glu Pro
                165                 170                 175

Glu Asn Asn Tyr Gln Thr Thr Pro Pro Gln Leu Asp Ser Asp Gly Thr
            180                 185                 190

Tyr Phe Leu Tyr Ser Arg Leu Ser Val Asp Arg Ser His Trp Gln Arg
        195                 200                 205

Gly Asn Thr Tyr Thr Cys Ser Val Ser His Glu Ala Leu His Ser His
            210                 215                 220

His Thr Gln Lys Ser Leu Thr Gln Ser Pro Gly Lys
225                 230                 235

<210> SEQ ID NO 27
<211> LENGTH: 229
<212> TYPE: PRT
<213> ORGANISM: Equus caballus

<400> SEQUENCE: 27
```

```
Val Ile Lys Glu Cys Asn Gly Gly Cys Pro Ala Glu Cys Leu Gln Val
1               5                   10                  15

Gly Pro Ser Val Phe Ile Phe Pro Pro Lys Pro Lys Asp Val Leu Met
            20                  25                  30

Ile Ser Arg Thr Pro Thr Val Thr Cys Val Val Val Asp Val Gly His
            35                  40                  45

Asp Phe Pro Asp Val Gln Phe Asn Trp Tyr Val Asp Gly Val Glu Thr
50                      55                  60

His Thr Ala Thr Thr Glu Pro Lys Gln Glu Gln Phe Asn Ser Thr Tyr
65                  70                  75                  80

Arg Val Val Ser Val Leu Pro Ile Gln His Lys Asp Trp Leu Ser Gly
                85                  90                  95

Lys Glu Phe Lys Cys Lys Val Asn Asn Lys Ala Leu Pro Ala Pro Val
            100                 105                 110

Glu Arg Thr Ile Ser Lys Pro Thr Gly Gln Pro Arg Glu Pro Gln Val
            115                 120                 125

Tyr Val Leu Ala Pro His Arg Asp Glu Leu Ser Lys Asn Lys Val Ser
130                 135                 140

Val Thr Cys Leu Val Lys Asp Phe Tyr Pro Thr Asp Ile Asp Ile Glu
145                 150                 155                 160

Trp Lys Ser Asn Gly Gln Pro Glu Pro Glu Thr Lys Tyr Ser Thr Thr
                165                 170                 175

Pro Ala Gln Leu Asp Ser Asp Gly Ser Tyr Phe Leu Tyr Ser Lys Leu
            180                 185                 190

Thr Val Glu Thr Asn Arg Trp Gln Gln Gly Thr Thr Phe Thr Cys Ala
            195                 200                 205

Val Met His Glu Ala Leu His Asn His Tyr Thr Glu Lys Ser Val Ser
210                 215                 220

Lys Ser Pro Gly Lys
225

<210> SEQ ID NO 28
<211> LENGTH: 242
<212> TYPE: PRT
<213> ORGANISM: Equus caballus

<400> SEQUENCE: 28

Cys Val Leu Ser Ala Glu Gly Val Ile Pro Ile Ser Val Pro Lys
1               5                   10                  15

Pro Gln Cys Pro Pro Tyr Thr His Ser Lys Phe Leu Gly Gly Pro Ser
            20                  25                  30

Val Phe Ile Phe Pro Pro Asn Pro Lys Asp Ala Leu Met Ile Ser Arg
            35                  40                  45

Thr Pro Val Val Thr Cys Val Val Asn Leu Ser Asp Gln Tyr Pro
50                  55                  60

Asp Val Gln Phe Ser Trp Tyr Val Asp Asn Thr Glu Val His Ser Ala
65                  70                  75                  80

Ile Thr Lys Gln Arg Glu Ala Gln Phe Asn Ser Thr Tyr Arg Val Val
                85                  90                  95

Ser Val Leu Pro Ile Gln His Gln Asp Trp Leu Ser Gly Lys Glu Phe
            100                 105                 110

Lys Cys Ser Val Thr Asn Val Gly Val Pro Gln Pro Ile Ser Arg Ala
            115                 120                 125

Ile Ser Arg Gly Lys Gly Pro Ser Arg Val Pro Gln Val Tyr Val Leu
```

```
                130                 135                 140
Pro Pro His Pro Asp Glu Leu Ala Lys Ser Lys Val Ser Val Thr Cys
145                 150                 155                 160

Leu Val Lys Asp Phe Tyr Pro Pro Asp Ile Ser Val Glu Trp Gln Ser
                165                 170                 175

Asn Arg Trp Pro Glu Leu Glu Gly Lys Tyr Ser Thr Thr Pro Ala Gln
                180                 185                 190

Leu Asp Gly Asp Gly Ser Tyr Phe Leu Tyr Ser Lys Leu Ser Leu Glu
                195                 200                 205

Thr Ser Arg Trp Gln Gln Val Glu Ser Phe Thr Cys Ala Val Met His
            210                 215                 220

Glu Ala Leu His Asn His Phe Thr Lys Thr Asp Ile Ser Glu Ser Leu
225                 230                 235                 240

Gly Lys

<210> SEQ ID NO 29
<211> LENGTH: 232
<212> TYPE: PRT
<213> ORGANISM: Equus caballus

<400> SEQUENCE: 29

Thr Thr Pro Pro Cys Pro Cys Glu Cys Pro Lys Cys Pro Ala Pro Glu
1               5                   10                  15

Leu Leu Gly Gly Pro Ser Val Phe Ile Phe Pro Pro Lys Pro Lys Asp
                20                  25                  30

Val Leu Met Ile Thr Arg Thr Pro Glu Val Thr Cys Leu Val Val Asp
            35                  40                  45

Val Ser His Asp Ser Ser Asp Val Leu Phe Thr Trp Tyr Val Asp Gly
50                  55                  60

Thr Glu Val Lys Thr Ala Lys Thr Met Pro Asn Glu Glu Gln Asn Asn
65                  70                  75                  80

Ser Thr Tyr Arg Val Val Ser Val Leu Arg Ile Gln His Gln Asp Trp
                85                  90                  95

Leu Asn Gly Lys Lys Phe Lys Cys Lys Val Asn Asn Gln Ala Leu Pro
                100                 105                 110

Ala Pro Val Glu Arg Thr Ile Ser Lys Ala Thr Gly Gln Thr Arg Val
            115                 120                 125

Pro Gln Val Tyr Val Leu Ala Pro His Pro Asp Glu Leu Ser Lys Asn
130                 135                 140

Lys Val Ser Val Thr Cys Leu Val Lys Asp Phe Leu Pro Thr Asp Ile
145                 150                 155                 160

Thr Val Glu Trp Gln Ser Asn Glu His Pro Glu Pro Glu Gly Lys Tyr
                165                 170                 175

Arg Thr Thr Glu Ala Gln Lys Asp Ser Asp Gly Ser Tyr Phe Leu Tyr
                180                 185                 190

Ser Lys Leu Thr Val Glu Thr Asp Arg Trp Gln Gln Gly Thr Thr Phe
            195                 200                 205

Thr Cys Val Val Met His Glu Ala Leu His Asn His Val Met Gln Lys
210                 215                 220

Asn Val Ser His Ser Pro Gly Lys
225                 230

<210> SEQ ID NO 30
<211> LENGTH: 229
<212> TYPE: PRT
```

<213> ORGANISM: Equus caballus

<400> SEQUENCE: 30

```
Val Ile Lys Glu Cys Asn Gly Gly Cys Pro Ala Glu Cys Leu Gln Val
1               5                   10                  15
Gly Pro Ser Val Phe Ile Phe Pro Pro Lys Pro Lys Asp Val Leu Met
            20                  25                  30
Ile Ser Arg Thr Pro Thr Val Thr Cys Val Val Asp Val Gly His
        35                  40                  45
Asp Phe Pro Asp Val Gln Phe Asn Trp Tyr Val Asp Gly Val Glu Thr
    50                  55                  60
His Thr Ala Thr Thr Glu Pro Lys Gln Glu Gln Phe Asn Ser Thr Tyr
65                  70                  75                  80
Arg Val Val Ser Val Leu Pro Ile Gln His Lys Asp Trp Leu Ser Gly
                85                  90                  95
Lys Glu Phe Lys Cys Lys Val Asn Asn Lys Ala Leu Pro Ala Pro Val
            100                 105                 110
Glu Arg Thr Ile Ser Lys Pro Thr Gly Gln Pro Arg Glu Pro Gln Val
            115                 120                 125
Tyr Val Leu Ala Pro His Arg Asp Glu Leu Ser Lys Asn Lys Val Ser
130                 135                 140
Val Thr Cys Leu Val Lys Asp Phe Tyr Pro Thr Asp Ile Asp Ile Glu
145                 150                 155                 160
Trp Lys Ser Asn Gly Gln Pro Glu Pro Glu Thr Lys Tyr Ser Thr Thr
                165                 170                 175
Pro Ala Gln Leu Asp Ser Asp Gly Ser Tyr Phe Leu Tyr Ser Lys Leu
            180                 185                 190
Thr Val Glu Thr Asn Arg Trp Gln Gln Gly Thr Thr Phe Thr Cys Ala
            195                 200                 205
Val Met His Glu Ala Leu His Asn His Tyr Thr Glu Lys Ser Val Ser
    210                 215                 220
Lys Ser Pro Gly Lys
225
```

<210> SEQ ID NO 31
<211> LENGTH: 230
<212> TYPE: PRT
<213> ORGANISM: Equus caballus

<400> SEQUENCE: 31

```
Val Val Lys Gly Ser Pro Cys Pro Lys Cys Pro Ala Pro Glu Leu Pro
1               5                   10                  15
Gly Gly Pro Ser Val Phe Ile Phe Pro Pro Lys Pro Lys Asp Val Leu
            20                  25                  30
Lys Ile Ser Arg Lys Pro Glu Val Thr Cys Val Val Asp Leu Gly
        35                  40                  45
His Asp Asp Pro Asp Val Gln Phe Thr Trp Phe Val Asp Gly Val Glu
    50                  55                  60
Thr His Thr Ala Thr Thr Glu Pro Lys Glu Gln Phe Asn Ser Thr
65                  70                  75                  80
Tyr Arg Val Val Ser Val Leu Pro Ile Gln His Gln Asp Trp Leu Ser
                85                  90                  95
Gly Lys Glu Phe Lys Cys Ser Val Thr Asn Lys Ala Leu Pro Ala Pro
            100                 105                 110
Val Glu Arg Thr Thr Ser Lys Ala Lys Gly Gln Leu Arg Val Pro Gln
```

```
              115                 120                 125
Val Tyr Val Leu Ala Pro His Pro Asp Glu Leu Ala Lys Asn Thr Val
        130                 135                 140

Ser Val Thr Cys Leu Val Lys Asp Phe Tyr Pro Pro Glu Ile Asp Val
145                 150                 155                 160

Glu Trp Gln Ser Asn Glu His Pro Glu Pro Glu Gly Lys Tyr Ser Thr
                165                 170                 175

Thr Pro Ala Gln Leu Asn Ser Asp Gly Ser Tyr Phe Leu Tyr Ser Lys
            180                 185                 190

Leu Ser Val Glu Thr Ser Arg Trp Lys Gln Gly Glu Ser Phe Thr Cys
                195                 200                 205

Gly Val Met His Glu Ala Val Glu Asn His Tyr Thr Gln Lys Asn Val
            210                 215                 220

Ser His Ser Pro Gly Lys
225                 230

<210> SEQ ID NO 32
<211> LENGTH: 224
<212> TYPE: PRT
<213> ORGANISM: Equus caballus

<400> SEQUENCE: 32

Lys Glu Pro Cys Cys Cys Pro Lys Cys Pro Gly Arg Pro Ser Val Phe
1               5                   10                  15

Ile Phe Pro Pro Asn Pro Lys Asp Thr Leu Met Ile Ser Arg Thr Pro
            20                  25                  30

Glu Val Thr Cys Val Val Val Asp Val Ser Gln Glu Asn Pro Asp Val
        35                  40                  45

Lys Phe Asn Trp Tyr Val Asp Gly Val Glu Ala His Thr Ala Thr Thr
    50                  55                  60

Lys Ala Lys Glu Lys Gln Asp Asn Ser Thr Tyr Arg Val Val Ser Val
65                  70                  75                  80

Leu Pro Ile Gln His Gln Asp Trp Arg Arg Gly Lys Glu Phe Lys Cys
                85                  90                  95

Lys Val Asn Asn Arg Ala Leu Pro Ala Pro Val Glu Arg Thr Ile Thr
            100                 105                 110

Lys Ala Lys Gly Glu Leu Gln Asp Pro Lys Val Tyr Ile Leu Ala Pro
        115                 120                 125

His Arg Glu Glu Val Thr Lys Asn Thr Val Ser Val Thr Cys Leu Val
130                 135                 140

Lys Asp Phe Tyr Pro Pro Asp Ile Asn Val Glu Trp Gln Ser Asn Glu
145                 150                 155                 160

Glu Pro Glu Pro Glu Val Lys Tyr Ser Thr Thr Pro Ala Gln Leu Asp
                165                 170                 175

Gly Asp Gly Ser Tyr Phe Leu Tyr Ser Lys Leu Thr Val Glu Thr Asp
            180                 185                 190

Arg Trp Glu Gln Gly Glu Ser Phe Thr Cys Val Val Met His Glu Ala
        195                 200                 205

Ile Arg His Thr Tyr Arg Gln Lys Ser Ile Thr Asn Phe Pro Gly Lys
    210                 215                 220

<210> SEQ ID NO 33
<211> LENGTH: 230
<212> TYPE: PRT
<213> ORGANISM: Equus caballus
```

<400> SEQUENCE: 33

```
Val Ile Lys Glu Cys Gly Gly Cys Pro Thr Cys Pro Glu Cys Leu Ser
1               5                   10                  15
Val Gly Pro Ser Val Phe Ile Phe Pro Pro Lys Pro Lys Asp Val Leu
            20                  25                  30
Met Ile Ser Arg Thr Pro Thr Val Thr Cys Val Val Val Asp Val Gly
        35                  40                  45
His Asp Phe Pro Asp Val Gln Phe Asn Trp Tyr Val Asp Gly Val Glu
    50                  55                  60
Thr His Thr Ala Thr Thr Glu Pro Lys Gln Glu Gln Asn Asn Ser Thr
65                  70                  75                  80
Tyr Arg Val Val Ser Ile Leu Ala Ile Gln His Lys Asp Trp Leu Ser
                85                  90                  95
Gly Lys Glu Phe Lys Cys Lys Val Asn Asn Gln Ala Leu Pro Ala Pro
            100                 105                 110
Val Gln Lys Thr Ile Ser Lys Pro Thr Gly Gln Pro Arg Glu Pro Gln
        115                 120                 125
Val Tyr Val Leu Ala Pro His Arg Asp Glu Leu Ser Lys Asn Lys Val
    130                 135                 140
Ser Val Thr Cys Leu Val Lys Asp Phe Tyr Pro Thr Asp Ile Asp Ile
145                 150                 155                 160
Glu Trp Lys Ser Asn Gly Gln Pro Glu Pro Glu Thr Lys Tyr Ser Thr
                165                 170                 175
Thr Pro Ala Gln Leu Asp Ser Asp Gly Ser Tyr Phe Leu Tyr Ser Lys
            180                 185                 190
Leu Thr Val Glu Thr Asn Arg Trp Gln Gln Gly Thr Thr Phe Thr Cys
        195                 200                 205
Ala Val Met His Glu Ala Leu His Asn His Tyr Thr Glu Lys Ser Val
    210                 215                 220
Ser Lys Ser Pro Gly Lys
225                 230
```

<210> SEQ ID NO 34
<211> LENGTH: 328
<212> TYPE: PRT
<213> ORGANISM: Canis familiaris

<400> SEQUENCE: 34

```
Lys Glu Ala Cys Pro Thr Gly Leu Tyr Thr His Ser Gly Glu Cys Cys
1               5                   10                  15
Lys Ala Cys Asn Leu Gly Glu Gly Val Ala Gln Pro Cys Gly Ala Asn
            20                  25                  30
Gln Thr Val Cys Glu Pro Cys Leu Asp Ser Val Thr Phe Ser Asp Val
        35                  40                  45
Val Ser Ala Thr Glu Pro Cys Lys Pro Cys Thr Glu Cys Val Gly Leu
    50                  55                  60
Gln Ser Met Ser Ala Pro Cys Val Glu Ala Asp Asp Ala Val Cys Arg
65                  70                  75                  80
Cys Ala Tyr Gly Tyr Tyr Gln Asp Glu Thr Thr Gly Arg Cys Glu Ala
                85                  90                  95
Cys Arg Val Cys Glu Ala Gly Ser Gly Leu Val Phe Ser Cys Gln Asp
            100                 105                 110
Arg Gln Asn Thr Val Cys Glu Glu Cys Pro Asp Gly Thr Tyr Ser Asp
        115                 120                 125
```

```
Glu Ala Asn His Val Asp Pro Cys Leu Pro Cys Thr Val Cys Glu Asp
130                 135                 140

Thr Glu Arg Gln Leu Arg Glu Cys Thr Arg Trp Ala Asp Ala Glu Cys
145                 150                 155                 160

Glu Glu Ile Pro Lys Glu Ala Cys Pro Thr Gly Leu Tyr Thr His Ser
                165                 170                 175

Gly Glu Cys Cys Lys Ala Cys Asn Leu Gly Glu Gly Val Ala Gln Pro
            180                 185                 190

Cys Gly Ala Asn Gln Thr Val Cys Glu Pro Cys Leu Asp Ser Val Thr
        195                 200                 205

Phe Ser Asp Val Val Ser Ala Thr Glu Pro Cys Lys Pro Cys Thr Glu
210                 215                 220

Cys Val Gly Leu Gln Ser Met Ser Ala Pro Cys Val Glu Ala Asp Asp
225                 230                 235                 240

Ala Val Cys Arg Cys Ala Tyr Gly Tyr Tyr Gln Asp Glu Thr Thr Gly
                245                 250                 255

Arg Cys Glu Ala Cys Arg Val Cys Glu Ala Gly Ser Gly Leu Val Phe
            260                 265                 270

Ser Cys Gln Asp Arg Gln Asn Thr Val Cys Glu Glu Cys Pro Asp Gly
        275                 280                 285

Thr Tyr Ser Asp Glu Ala Asn His Val Asp Pro Cys Leu Pro Cys Thr
    290                 295                 300

Val Cys Glu Asp Thr Glu Arg Gln Leu Arg Glu Cys Thr Arg Trp Ala
305                 310                 315                 320

Asp Ala Glu Cys Glu Glu Ile Pro
                325

<210> SEQ ID NO 35
<211> LENGTH: 498
<212> TYPE: DNA
<213> ORGANISM: Canis familiaris

<400> SEQUENCE: 35
aaggaggcat gtcccactgg cctgtacacc cacagcggcg agtgctgcaa agcctgcaat      60
ctgggtgagg gggtggccca gccttgcgga gccaaccaga ccgtgtgtga gccctgcctg     120
gacagcgtga ccttctcgga cgtggtgagc gccaccgagc cgtgcaagcc gtgcaccgag     180
tgcgtggggc tgcagagcat gtcggcgccg tgcgtggagg cggacgacgc cgtgtgccgc     240
tgcgcctacg gctactacca ggacgagacg acgggccgct gcgaggcgtg ccgcgtgtgc     300
gaggcgggct cggggctcgt gttctcgtgc caggacaggc agaacaccgt gtgcgaggag     360
tgtcccgacg gcacgtactc cgacgaggcc aaccacgtgg acccgtgcct gccctgcacc     420
gtgtgcgagg acaccgagcg ccagctgcgc gagtgcacgc gctgggccga cgccgagtgc     480
gaggagatcc ctggccgt                                                    498

<210> SEQ ID NO 36
<211> LENGTH: 399
<212> TYPE: PRT
<213> ORGANISM: Bos taurus

<400> SEQUENCE: 36

Lys Glu Ala Cys Leu Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30
```

```
Gln Thr Val Cys Glu Pro Cys Leu Asp Ser Val Thr Phe Ser Asp Val
            35                  40                  45

Val Ser Ala Thr Glu Pro Cys Lys Pro Cys Thr Glu Cys Val Gly Leu
 50                  55                  60

Gln Ser Met Ser Ala Pro Cys Val Glu Ala Asp Asp Ala Val Cys Arg
 65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
            115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ala Thr Pro Glu Gly
                165                 170                 175

Ser Asp Ser Thr Asp Pro Ser Thr Gln Glu Pro Glu Val Pro Pro Glu
                180                 185                 190

Gln Asp Leu Val Thr Ser Thr Val Ser Asp Val Val Thr Thr Val Met
        195                 200                 205

Gly Ser Ser Gln Pro Val Val Thr Arg Gly Thr Ala Asp Asn Leu Ile
    210                 215                 220

Pro Val Tyr Cys Ser Ile Leu Ala Ala Val Val Gly Leu Val Ala
225                 230                 235                 240

Tyr Ile Ala Phe Lys Arg Trp Asn Ser Cys Lys Gln Asn Lys Gln Gly
                245                 250                 255

Ala Asn Ser Arg Pro Val Asn Gln Thr Pro Pro Glu Gly Glu Lys
            260                 265                 270

Leu His Ser Asp Ser Gly Ile Ser Val Asp Ser Gln Ser Leu His Asp
            275                 280                 285

Gln Gln Pro His Thr Gln Thr Ala Ala Gly Gln Ala Leu Lys Gly Asp
    290                 295                 300

Gly Gly Leu Tyr Ser Ser Leu Pro Leu Ala Lys Arg Glu Glu Val Glu
305                 310                 315                 320

Lys Leu Leu Asn Gly Ser Ala Gly Asp Thr Trp Arg His Leu Ala Gly
                325                 330                 335

Glu Leu Gly Tyr Gln Pro Glu His Ile Asp Ser Phe Thr His Glu Ala
                340                 345                 350

Cys Pro Ala Arg Ala Leu Leu Ala Ser Trp Ala Ala Gln Asp Ser Ala
            355                 360                 365

Thr Leu Asp Thr Leu Leu Ala Ala Leu Arg Arg Ile Gln Arg Ala Asp
    370                 375                 380

Leu Val Glu Ser Leu Cys Ser Glu Ser Thr Ala Thr Ser Pro Val
385                 390                 395

<210> SEQ ID NO 37
<211> LENGTH: 1290
<212> TYPE: DNA
<213> ORGANISM: Bos taurus

<400> SEQUENCE: 37
atggggtcag gtgccgccgg ccgcgccatg gacgggccgc gcctgctgct gctgctgctg      60
```

```
ctgctcctgg gggtgtccct tggaggtgcc aaggaagcat gcctcacggg cctgtacacc    120
cacagcggag agtgctgcaa agcctgcaac ctgggcgagg gtgtggccca gccttgtgga    180
gccaaccaga ccgtgtgtga accctgcctg gacagcgtga ccttctcgga cgtggtgagc    240
gccacggagc cgtgtaagcc gtgcacggag tgcgtgggac tgcagagcat gtcggcgccc    300
tgcgtggagg ccgacgacgc cgtgtgccgc tgcgcctacg gctattacca ggacgagacg    360
accggccgct gcgaggcgtg ccgcgtgtgc gaggcgggct cggggctcgt gttctcgtgc    420
caggacaagc agaacaccgt ctgcgaggag tgccccgacg gcacgtactc cgacgaggcc    480
aaccacgtgg acccctgcct gccctgcacg gtgtgcgagg acacggagcg ccagctgcgc    540
gagtgcacgc gctgggccga cgccgagtgc gaggagatcc ctggacgttg gattacacgg    600
gccacgcccc ctgagggctc cgacagcaca gaccccagca cccaggagcc cgaggtacct    660
ccagagcaag atctggtaac cagcactgtg tcagatgtgg tgaccacggt gatgggcagc    720
tcccagcctg tggtgacccg aggtaccgcc gacaacctca tccctgtcta ttgctccatc    780
ctggctgctg tggttgtggg ccttgtggcc tacatcgcct tcaagaggtg gaacagctgc    840
aagcagaaca gcaaggagc caacagccga cctgtgaacc agacaccccc accagagggg    900
gaaaagctac acagcgatag cggcatctct gtggacagcc agagcctgca tgaccagcag    960
ccccacacgc agactgccgc aggccaggcc ctcaagggtg atggaggcct ctacagcagc    1020
ctgccgctgg ccaagcggga ggaggtggag aagctgctca acggctctgc gggggacacc    1080
tggcggcatc tggcaggcga gttgggttac cagcctgagc acatagactc cttcacccac    1140
gaggcctgcc cagcccgcgc cctgctggcc agctgggctg cccaggacag cgccacgctc    1200
gacaccctcc ttgcggccct gcgccgcatc cagcgcgccg acatcgtgga gagcctgtgc    1260
agcgagtcca cggccacgtc ccccgtgtga                                    1290
```

```
<210> SEQ ID NO 38
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 38

Gly Gly Gly Gly Ser
1               5
```